(12) United States Patent
Sunagawa et al.

(10) Patent No.: US 7,468,364 B2
(45) Date of Patent: Dec. 23, 2008

(54) CARBAPENEM COMPOUNDS

(75) Inventors: Makoto Sunagawa, Osaka (JP); Akira Sasaki, Osaka (JP); Seiji Hori, Osaka (JP)

(73) Assignee: Dainippon Sumitomo Pharma Co., Ltd., Osaka-Fu (JP)

( * ) Notice: Subject to any disclaimer, the term of this patent is extended or adjusted under 35 U.S.C. 154(b) by 267 days.

(21) Appl. No.: 10/550,395

(22) PCT Filed: Apr. 6, 2004

(86) PCT No.: PCT/JP2004/004978

§ 371 (c)(1),
(2), (4) Date: Sep. 22, 2005

(87) PCT Pub. No.: WO2004/089954

PCT Pub. Date: Oct. 21, 2004

(65) Prior Publication Data

US 2006/0183730 A1 Aug. 17, 2006

(30) Foreign Application Priority Data

Apr. 8, 2003 (JP) ............... 2003-104539
Apr. 30, 2003 (JP) ............... 2003-125016
Apr. 30, 2003 (JP) ............... 2003-125738

(51) Int. Cl.
*C07D 477/14* (2006.01)
*A61K 31/407* (2006.01)
*A61P 31/04* (2006.01)
*A61K 31/4178* (2006.01)
*A61K 31/5377* (2006.01)
*A61K 31/4439* (2006.01)
*C07F 7/18* (2006.01)

(52) U.S. Cl. .................. 514/210.09; 540/302; 540/200
(58) Field of Classification Search ................ 540/302; 514/210.09
See application file for complete search history.

(56) References Cited

U.S. PATENT DOCUMENTS

| | | | |
|---|---|---|---|
| 4,203,902 A | | 5/1980 | Shih |
| 4,223,038 A | * | 9/1980 | Smale ............... 514/210.1 |
| 4,235,776 A | | 11/1980 | Kornfeld et al. |
| 4,260,627 A | | 4/1981 | Christensen et al. |
| 4,264,622 A | | 4/1981 | Kornfeld et al. |
| 4,350,703 A | * | 9/1982 | Dickinson et al. ...... 514/210.09 |
| 4,429,128 A | * | 1/1984 | Rosati ................ 540/302 |
| 4,464,299 A | | 8/1984 | Uyeo ................. 540/302 |
| 4,536,335 A | * | 8/1985 | Kim et al. ............ 540/350 |
| 4,543,257 A | | 9/1985 | Cama et al. |
| 4,775,669 A | | 10/1988 | Cama et al. |
| 5,011,832 A | | 4/1991 | Dininno et al. |
| 5,025,006 A | | 6/1991 | Dininno et al. |
| 5,034,385 A | * | 7/1991 | DiNinno et al. ........ 514/80 |
| 5,055,463 A | * | 10/1991 | Greenlee et al. ....... 514/210.09 |
| 5,055,573 A | | 10/1991 | Cama et al. |
| 5,064,447 A | | 11/1991 | Lee |

(Continued)

FOREIGN PATENT DOCUMENTS

EP 0 430 037 6/1991

(Continued)

OTHER PUBLICATIONS

William J. Weiss, et al., "In Vivo Activities of Peptide Prodrugs of Novel Aminomethyl Tetrahydrofuranyl-1β-Methylcarbapenems", Antimicrobial Agents and Chemotherapy, vol. 43, No. 3, pp. 460-464, Mar. 1999.

(Continued)

*Primary Examiner*—Mark L Berch
(74) *Attorney, Agent, or Firm*—Wenderoth, Lind & Ponack, L.L.P.

(57) ABSTRACT

Carbapenem compounds represented by the general formula [1] or pharmaceutically acceptable salts thereof:

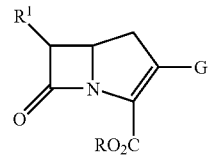

[1]

wherein $R^1$ is $C_1$-$C_3$ alkyl or hydroxylated $C_1$-$C_3$ alkyl, R is hydrogen atom or a group which is hydrolyzed in vivo into a carboxy group, and G is a group represented by one of the formulae [G1], [G2], and [G3].

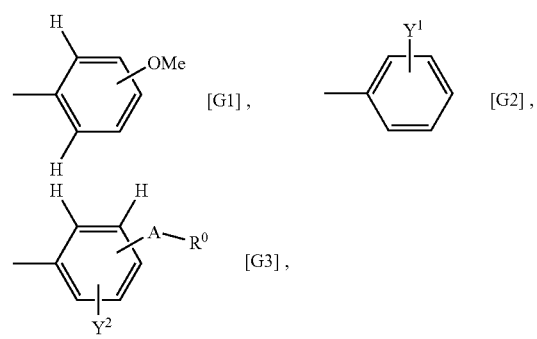

15 Claims, No Drawings

U.S. PATENT DOCUMENTS

| | | | |
|---|---|---|---|
| 5,104,867 A | 4/1992 | Kawamoto et al. | |
| 5,153,187 A | 10/1992 | Iwasaki et al. | |
| 5,208,348 A | 5/1993 | Iwasaki et al. | |
| 5,220,011 A | 6/1993 | DiNinno et al. | |
| 5,242,914 A | 9/1993 | Kawamoto et al. | |
| 5,256,777 A | 10/1993 | DiNinno et al. | |
| 5,258,509 A | 11/1993 | Nakagawa et al. | |
| 5,292,879 A | 3/1994 | DiNinno et al. | |
| 5,334,590 A | 8/1994 | DiNinno et al. | |
| 5,338,875 A | 8/1994 | DeCamp et al. | |
| 5,350,836 A | 9/1994 | Kopchick et al. | |
| 5,534,510 A | 7/1996 | Abe et al. | |
| 5,583,218 A | 12/1996 | Takemura et al. | |
| 5,587,374 A | 12/1996 | Perboni et al. | |
| 5,679,790 A | 10/1997 | Abe et al. | |
| 5,783,703 A | 7/1998 | Hayashi et al. | |
| 5,821,362 A | 10/1998 | Kaneko et al. | |
| 5,869,477 A * | 2/1999 | Lee et al. | 514/210.09 |
| 6,342,494 B1 | 1/2002 | Matsui et al. | |
| 6,410,525 B1 | 6/2002 | Matsui | |
| 7,115,595 B2 * | 10/2006 | Sunagawa et al. | 514/210.09 |
| 7,205,291 B2 * | 4/2007 | Sunagawa et al. | 514/210.09 |
| 2004/0063683 A1 | 4/2004 | Sunagawa et al. | |
| 2004/0242874 A1 | 12/2004 | Winkley et al. | |
| 2005/0020566 A1 | 1/2005 | Sunagawa et al. | |

FOREIGN PATENT DOCUMENTS

| | | |
|---|---|---|
| EP | 0 538 001 | 4/1993 |
| JP | 53-87390 | 8/1978 |
| JP | 55-69586 | 5/1980 |
| JP | 4-211687 | 8/1992 |
| JP | 4-279587 | 10/1992 |
| JP | 5-222043 | 8/1993 |
| JP | 5-255331 | 10/1993 |
| JP | 7-70126 | 3/1995 |
| JP | 8-512280 | 12/1996 |
| WO | 03/40146 | 5/2003 |
| WO | 03/089431 | 10/2003 |

OTHER PUBLICATIONS

L.D. Cama et al., "Total Synthesis of Thienamycin Analogs—III, Synthesis of 2-Aryl and 2-Heteroaryl Analogs of Thienamycin", Tetrahedron, vol. 39, No. 15, pp. 2531-2549, 1983.

Ravindra Nath Guthikonda et al., "Structure-Activity Relationships in the 2-Arylcarbapenem Series: Synthesis of 1-Methyl-2-arylcarbapenems", Journal of Medicinal Chemistry, vol. 30, No. 5, pp. 871-880, 1987.

Jeremy D. Hinks, et al., "Preparation and reactivity of carbapenem-2-stannane", Tetrahedron Letters, vol. 41, No. 16, pp. 2995-2998, 2000.

Supplementary European Search Report issued on Jun. 3, 2008 in EP Application No. 04 72 6028 corresponding to the present US application.

Nobuyoshi Yasuda et al., "Preparation of 2-Aryl-and 2-Alkenyl-Substituted Carbapenems Under Mild Suzuki Cross-Coupling Conditions", Tetrahedron Letters, vol. 34, No. 20, Jan. 1, 1993, pp. 3211-3214, XP002922151, ISSN: 0040-4039.

* cited by examiner

CARBAPENEM COMPOUNDS

TECHNICAL FIELD

The present invention relates to a new carbapenem compound. In more detail, the present invention relates to a carbapenem compound, which contains 7-oxo-1-azabicyclo[3.2.0]hept-2-ene, wherein a substituted phenyl is directly substituted at position 3. Furthermore, the present invention relates to an antibacterial agent containing such a compound as an active ingredient.

BACKGROUND ART

The carbapenem compounds which have been developed and commercialized are poor in absorbability from the digestive tract and therefore, they are clinically used only in the form of injections, mainly intravenous injections. However, in the clinical field, it is desirable to select several administration routes from the viewpoint of circumstances or wishes of a patient, a therapeutic object, etc. Especially, oral administration of an antibacterial agent is easy and convenient for administration to a patient in comparison with injection. In view of the care of a patient at home, oral administration of the antibacterial agent is more convenient and the clinical usability is extremely high. It has been strongly desired in the clinical field to develop a carbapenem compound which is rich in safety, is orally administrable and has a potent antibacterial activity, especially against penicillin resistant *Streptococcus pneumoniae* (PRSP) or *Haemophilus influenzae* (which widely gain resistance to known β-lactam agents by mutation of a penicillin binding protein (PBP), such as β-lactamase non-producing ampicillin resistant *Haemophilus influenzae* (BLNAR) which have been recently increasingly isolated and provide a clinical trouble.). However none of such agents has been put on the market. Tricyclic carbapenem compounds which have been studied and developed until now are disclosed for example, in WO92/03437. These compounds have a characteristic structure in a side chain having a ring which is fused via C—C bond and they are modified to a prodrug thereof for increase of oral absorbability, but their safety in the clinical test is not reported. Besides, there are several known 1β methylcarbapenem compounds (see WO 92/03437, Japanese patent publication A 2-49783, Japanese patent publication A 8-53453, WO 98/34936, WO 99/57121, Japanese patent publication A 4-279588, Japanese patent publication A 2-223587, and Antimicrobial Agents and Chemotherapy, March 1999, p 460-464). All of them have a structural property having 1β-methyl group and a side chain via sulfide bond which are said to contribute to an increase of chemical stability and in vivo (biological) stability, and are modified to a prodrug of them for increase of oral absorbability. Especially, the clinical trial was carried out on compounds disclosed in Japanese patent publication A 2-49783 and Japanese patent publication A 8-53453, but the safety of them and so on have been not clear.

On the other hand, carbapenem compounds having an aryl ring via C—C bond as a side chain structure were known since 1980s (see U.S. Pat. Nos. 4,543,257, 4,775,669, 5,258, 509, WO 02/053566, Tetrahedron, 1983, Vol. 39, p 2531-2549, Journal of Medicinal Chemistry, 1987, Vol. 30, p 871-880, EP 538001, and EP 538016). For example, in U.S. Pat. No. 4,543,257, carbapenam compounds directly substituted by para-methoxyphenyl group at position 3 of 7-oxo-1-azabicyclo[3.2.0]hept-2-ene which is a core structure of the carbapenem, and various compounds are described, and in the Journal of Medicinal Chemistry, Vol. 30, p 871-880 (1987), carbapenam compounds directly substituted by para-methoxyphenyl group at position 3 of 7-oxo-1-azabicyclo[3.2.0]hept-2-ene which is a basic nucleus of the carbapenem and so on are described. Although there are many other reports on these compounds, these reports are concerned only to studies and developments on injections thereof, but not to studies for oral application thereof.

Recently, carbapenem derivatives having a benzene ring and so on directly bound by substituted carbamoyl group at position 3 of 7-oxo-1-azabicyclo[3.2.0]hept-2-ene which is a core structure of the carbapenem (for example, WO 02/053566), carbapenem derivatives having a benzene ring bound via spacer with substituted carbamoyl group at position 3 of 7-oxo-1-azabicyclo[3.2.0]hept-2-ene which is a core structure of the carbapenem (for example, WO 03/040146), and carbapenem derivatives having a substituted pyridine ring, etc. at position 3 of 7-oxo-1-azabicyclo[3.2.0]hept-2-ene which is a core structure of the carbapenem (for example, WO 03/089431) are suggested to be used for oral agents, but the carbapenem derivatives having such a substituent pattern as the compound of the present invention are not known and that such compounds are not known as oral antibacterial agents.

DISCLOSURE OF INVENTION

The object of the present invention is to provide a carbapenem compound which has a potent antibacterial activity against Gram positive bacteria and Gram negative bacteria, especially penicillin resistant *Streptococcus pneumoniae* (PRSP) or *Haemophilus influenzae* (which obtain resistance to known β-lactam agents by mutation of a penicillin binding protein (PBP) such as β-lactamase non-producing ampicillin resistant *Haemophilus influenzae* (BLNAR), which have been recently increasingly isolated and provide a clinical problem) and has excellent oral absorbability.

The present inventors have intensively studied to find that the carbapenem compound, wherein a substituted phenyl is directly substituted at position 3 of 7-oxo-1-azabicyclo[3.2.0] hept-2-ene which is a core structure of the carbapenem compound, has a potent antibacterial activity against Gram positive bacteria and Gram negative bacteria, especially penicillin resistant *Streptococcus pneumoniae* (PRSP) or *Haemophilus influenzae* which obtain resistance to known β-lactam agents by mutation of a penicillin binding protein (PBP) such as β-lactamase non-producing ampicillin resistant *Haemophilus influenzae* (BLNAR) which have been recently increasingly isolated and provide a clinical problem. Further, they have also found that a compound having a group substituted onto the 2-carboxyl group, the said group being capable of regenerating a carboxyl group by hydrolyzing in the living body, shows a good absorbability from the digestive tract by oral administration, and shows a potent antibacterial activity after converted into a 2-de-esterified compound in the living body, and further shows an excellent resistance to renal dehydropeptidase. Thus the present invention finally has been accomplished.

Namely the summary of the present invention are as follows.

(1) A carbapenem compound or a pharmaceutically acceptable salt thereof represented by the following formula [1]

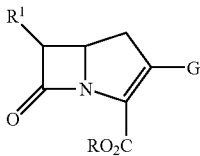

wherein $R^1$ is $C_1$-$C_3$ alkyl group or $C_1$-$C_3$ alkyl group substituted by hydroxy group, R is hydrogen atom or a group which reproduces carboxyl group by hydrolysis in vivo, and G is a group represented by the formula G1:

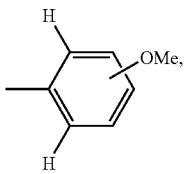

the formula G2:

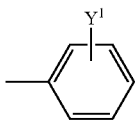

wherein $Y^1$ is $C_1$-$C_4$ alkyl, $C_2$-$C_4$ alkoxy, —$(CH_2)_{ma}$—O—$CH_3$ (in which ma is an integer of 1~3), —O—$(CH_2)_{ma}$—O—$(CH_2)_{mb}$—$CH_3$ (in which ma is the same as defined above, mb is an integer of 0~3), trifluoromethoxy, halogen atom, cyano or —$SO_2NR^2R^3$ (in which $R^2$ and $R^3$ are independently hydrogen atom, optionally substituted lower alkyl, optionally substituted aryl, optionally substituted heteroaryl, optionally substituted aralkyl, or optionally substituted heteroarylalkyl, or $R^2$ and $R^3$ may be taken together with the nitrogen atom to form a 3 to 7 membered hetero ring which may be substituted.), or the formula G3:

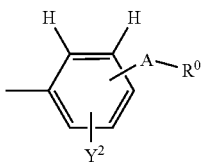

wherein A is —$(CH_2)_r$—(in which r is an integer of 1~3), —$(CH_2)_s$—O—$(CH_2)_t$—(in which s and t are independently is an integer of 0~3), —O—$(CH_2)_r$—O—$(CH_2)_s$—(in which r and s are the same as defined above), —$(CH_2)_s$—$NR^a$—$(CH_2)_t$—(in which, s and t are the same as defined above, $R^a$ is hydrogen atom, protective group of amino group or optionally substituted $C_1$-$C_6$ alkyl), $R^0$ is hydrogen atom, the formula [2]:

wherein $R^{2a}$ and $R^{3a}$ are independently (i) hydrogen atom, (ii) optionally substituted $C_1$-$C_6$ alkyl, (iii) optionally substituted $C_3$-$C_7$ cycloalkyl, (iv) optionally substituted aryl, (v) optionally substituted heteroaryl, (vi) optionally substituted aralkyl, (vii) optionally substituted heteroarylalkyl, or (viii) an optionally substituted 3 to 7 membered hetero ring, or $R^{2a}$ and $R^{3a}$ are taken together with the nitrogen atom to form a 3 to 7 membered hetero ring which may be substituted, or the formula [3]:

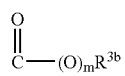

wherein m is an integer of 0 or 1, $R^{3b}$ is hydrogen atom, optionally substituted $C_1$-$C_6$ alkyl, optionally substituted $C_3$-$C_7$ cycloalkyl, optionally substituted aryl, optionally substituted heteroaryl, optionally substituted aralkyl, optionally substituted heteroarylalkyl, or an optionally substituted 3 to 7 membered hetero ring, and when m is 1, $R^{3b}$ may further mean a group which reproduces carboxyl group by hydrolysis in vivo, provided that when t is 0 and m is 1, $R^{3b}$ is other group than hydrogen atom, and $Y^2$ is $C_1$-$C_4$ alkyl, $C_1$-$C_4$ alkoxy, halogen atom, cyano or —$NR^4R^5$ (in which $R^4$ and $R^5$ are independently (i) hydrogen atom, (ii) a protective group of amino group, (iii) optionally substituted $C_1$-$C_6$ alkyl, (iv) optionally substituted $C_3$-$C_7$ cycloalkyl, (v) formyl, (vi) $C_2$-$C_7$ alkylcarbonyl, (vii) optionally substituted aryl, (viii) optionally substituted heteroaryl, (ix) optionally substituted aralkyl, (x) optionally substituted heteroarylalkyl, or (xi) an optionally substituted 3 to 7 membered hetero ring, or $R^4$ and $R^5$ are taken together with the nitrogen atom to form pyrrolidine, piperidine or azepam).

(2) A carbapenem compound or a pharmaceutically acceptable salt thereof represented by the following formula [1-a] wherein G is G1 in the above formula [1]:

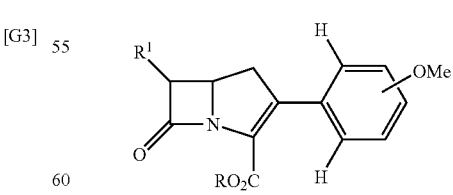

wherein $R^1$ and R are the same as defined above.

(3) A carbapenem compound or a pharmaceutically acceptable salt thereof represented by the following formula [1-b] wherein G1 is 4-methoxyphenyl in the compound described in above (2):

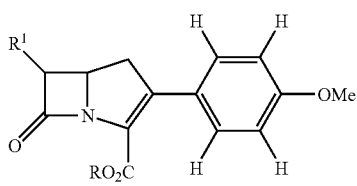

wherein $R^1$ and R are the same as defined above.

(4) A carbapenem compound or a pharmaceutically acceptable salt thereof represented by the following formula [1-c] wherein G is G2 in the above formula [1]:

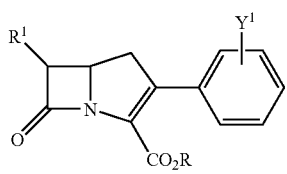

wherein $R^1$, R and $Y^1$ are the same as defined above.

(5) A carbapenem compound or a pharmaceutically acceptable salt thereof represented by the following formula [1-d] wherein G is G3 in the above formula [1]:

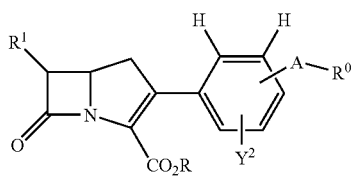

wherein $R^1$, R, A, $R^0$ and $Y^2$ are the same as defined above.

(6) A carbapenem compound described in above (1) to (5) or a pharmaceutically acceptable salt thereof wherein a group which reproduces carboxyl group by hydrolysis in vivo is a group of the formula [4]:

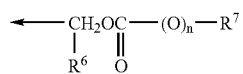

wherein $R^6$ is hydrogen atom or $C_1$-$C_6$ alkyl, $R^7$ is optionally substituted $C_1$-$C_{10}$ alkyl, or optionally substituted $C_3$-$C_{10}$ cycloalky, and n is an integer of 0 or 1.

(7) A carbapenem compound described in above (1) to (5) or a pharmaceutically acceptable salt thereof wherein R is a group of a formula [4] in above (6).

(8) A carbapenem compound described in above (1) to (7) or a pharmaceutically acceptable salt thereof wherein $R^1$ is 1-hydroxyethyl.

(9) A carbapenem compound described in above (1) to (5) or a pharmaceutically acceptable salt thereof wherein R is pivaloyloxymethyl, acetyloxymethyl, acetyloxy-1-ethyl, isopropyloxycarbonyloxy-1-ethyl or cyclohexyloxycarbonyloxy-1-ethyl.

(10) A carbapenem compound described in above (1) to (5) or a pharmaceutically acceptable salt thereof wherein R is pivaloyloxymethyl.

(11) A carbapenem compound described in above (1) to (5) or a pharmaceutically acceptable salt thereof wherein R is phthalidyl or (5-methyl-2-oxo-1,3-dioxol-4-yl)methyl.

(12) A carbapenem compound described in above (1) to (5) or a pharmaceutically acceptable salt thereof wherein R is hydrogen atom.

(13) A carbapenem compound described in above (4) or a pharmaceutically acceptable salt thereof wherein $Y^1$ is $C_2$-$C_4$ alkoxy, —$(CH_2)_{ma}$—O—$CH_3$ (in which ma is an integer of 1~3) or —O—$(CH_2)_{ma}$—O—$(CH_2)_{mb-CH3}$ (in which ma and mb are the same as defined above).

(14) A carbapenem compound described in above (4) or a pharmaceutically acceptable salt thereof wherein $Y^1$ is $C_1$-$C_4$ alkyl, trifluoromethoxy, halogen atom or cyano.

(15) A carbapenem compound described in above (4) or a pharmaceutically acceptable salt thereof wherein $Y^1$ is —$SO_2NR^2R^3$ (in which $R^2$ and $R^3$ are the same as defined above).

(16) A carbapenem compound described in above (4) or a pharmaceutically acceptable salt thereof wherein $Y^1$ is ethoxy, —$CH_2$—O—$CH_3$, —$(CH_2)_2$—O—$CH_3$ or —O—$(CH_2)_2$—O—$CH_3$.

(17) A carbapenem compound described in above (4) or (13) to (16) or a pharmaceutically acceptable salt thereof wherein $Y^1$ on benzene ring is metha or para to the binding position of 7-oxo-1-azabicyclo[3.2.0]hept-2-ene.

(18) A carbapenem compound described in above (4) or (13) to (16) or a pharmaceutically acceptable salt thereof wherein $Y^1$ on benzene ring is para to the binding position of 7-oxo-1-azabicyclo[3.2.0]hept-2-ene.

(19) A carbapenem compound described in above (5) or a pharmaceutically acceptable salt thereof wherein $R^0$ is a formula [2]:

wherein $R^{2a}$ and $R^{3a}$ are the same as defined above.

(20) A carbapenem compound described in above (5) or a pharmaceutically acceptable salt thereof, wherein $R^0$ is a formula [3]:

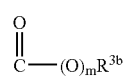

wherein m and $R^{3b}$ are the same as defined above.

(21) A carbapenem compound described in above (5) or a pharmaceutically acceptable salt thereof wherein $Y^2$ is $C_1$-$C_4$ alkyl.

(22) A carbapenem compound described in above (5) or a pharmaceutically acceptable salt thereof wherein $Y^2$ is $C_1$-$C_4$ alkoxy.

(23) A carbapenem compound described in above (5) or a pharmaceutically acceptable salt thereof wherein $Y^2$ is halogen atom or cyano.

(24) A carbapenem compound described in above (5) or a pharmaceutically acceptable salt thereof wherein $Y^2$ is —$NR^4R^5$ (in which $R^4$ and $R^5$ are the same as defined above).

(25) A medicament containing a carbapenem compound described in above (1) to (24) or a pharmaceutically acceptable salt thereof as an active ingredient.

(26) An antibacterial agent containing a carbapenem compound described in above (1) to (24) or a pharmaceutically acceptable salt thereof as an active ingredient.

(27) An oral medicament containing a carbapenem compound described in above (1) to (24) or a pharmaceutically acceptable salt thereof as an active ingredient.

(28) An oral antibacterial agent containing a carbapenem compound described in above (1) to (24) or a pharmaceutically acceptable salt thereof as an active ingredient.

BEST MODE FOR CARRYING OUT THE INVENTION

"$C_1$-$C_3$ alkyl" in $R^1$ includes, for example, straight or branched $C_1$-$C_3$ alkyl, such as methyl, ethyl, n-propyl, isopropyl, preferably ethyl or isopropyl.

"$C_1$-$C_3$ alkyl substituted by hydroxy" in $R^1$ includes, for example hydroxy $C_1$-$C_3$ alkyl, such as hydroxymethyl, 1-hydroxyethyl, 2-hydroxyethyl, 1-hydroxyl-methylethyl, 1-hydroxypropyl, preferably 1-hydroxyethyl, 2-hydroxyethyl or 1-hydroxy-1-methylethyl, and especially preferably 1-hydroxyethyl.

"$C_1$-$C_4$ alkyl" in $Y^1$ includes, such as methyl, ethyl, n-propyl, isopropyl, n-butyl, isobutyl, tert-butyl, preferably methyl, ethyl, n-propyl or isopropyl, and especially preferably methyl or ethyl.

"$C_2$-$C_4$ alkoxy" in $Y^1$ includes, for example, ethoxy, n-propoxy, isopropoxy, n-butoxy, isobutoxy, sec-butoxy, tert-butoxy, preferably ethoxy, n-propoxy or isopropoxy and especially preferably ethoxy.

"Halogen atom" in $Y^1$ includes fluorine atom, chlorine atom, bromine atom or iodine atom, preferably fluorine atom, chlorine atom and especially preferably fluorine atom.

"Lower alkyl" wherein $Y^1$ is —$SO_2NR^2R^3$ (in which $R^2$ and $R^3$ are independently hydrogen atom, optionally substituted lower alkyl, optionally substituted aryl, optionally substituted heteroaryl, optionally substituted aralkyl, or optionally substituted heteroarylalkyl, or $R^2$ and $R^3$ may be taken together with the nitrogen atom to form a 3 to 7 membered hetero ring which may be substituted.), includes methyl, ethyl, n-propyl, isopropyl, n-butyl, isobutyl, tert-butyl, preferably methyl, ethyl, n-propyl or isopropyl, and especially preferably methyl or ethyl.

"Aryl" moiety in "optionally substituted aryl" includes for example, phenyl or naphthyl and especially preferably phenyl.

"Heteroaryl" moiety in "optionally substituted heteroaryl" includes, for example, a 5 to 10 membered monocyclic or fused polycyclic aromatic ring containing 1 to 3 hetero atoms selected from nitrogen atom, oxygen atom and sulfur atom, such as pyridyl, pyrimidinyl, pyridazinyl, pyrazinyl, thienyl, furyl, pyrrolyl, imidazolyl, oxazolyl, isoxazolyl, thiazolyl, isothiazolyl, triazolyl, indolyl, benzothiazolyl, quinazolinyl or isoquinazolinyl, preferably pyridyl, pyrimidinyl, pyridazinyl, thienyl, furyl, pyrrolyl, imidazolyl, oxazolyl, isoxazolyl, thiazolyl, isothiazolyl or triazolyl and especially preferably pyridyl, thienyl, furyl, pyrrolyl, imidazolyl, oxazolyl, isoxazolyl or thiazolyl.

"Aralkyl" moiety in "optionally substituted aralkyl" includes such as benzyl, phenylethyl or naphthylmethyl, and preferably benzyl or phenylethyl.

"Heteroarylalkyl" moiety in "optionally substituted heteroarylalkyl" includes, for example, a group consisting a combination of a $C_1$-$C_3$ alkylene chain and a 5 to 10 membered monocyclic or fused polycyclic aromatic ring containing 1 to 3 hetero atoms selected from nitrogen atom, oxygen atom and sulfur atom, such as pyridylmethyl, pyrimidinylmethyl, pyridazinylmethyl, pyrazinylmethyl, thienylmethyl, furylmethyl, pyrrolylmethyl, imidazolylmethyl, oxazolylmethyl, isoxazolylmethyl, thiazolylmethyl, isothiazolylmethyl, triazolylmethyl, indolylmethyl, benzothiazolylmethyl, qunazolinylmethyl, isoquinazolinylmethyl, pyridylethyl, pyrimidinylethyl, pyridazinylethyl, pyrazinylethyl or pyridylpropyl. Preferable ones are pyridylmethyl, pyrimidinylmethyl, pyridazinylmethyl, thienylmethyl, furylmethyl, pyrrolylmethyl, imidazolylmethyl, oxazolylmethyl, isoxazolylmethyl, thiazolylmethyl, isothiazolylmethyl or triazolylmethyl and especially preferable ones are pyridylmethyl, thienylmethyl, furylmethyl, pyrrolylmethyl, imidazolylmethyl, oxazolylmethyl, isoxazolylmethyl or thiazolylmethyl.

"A 3 to 7 membered hetero ring" which $R^2$ and $R^3$ are taken together with the nitrogen atom to form, includes for example, a saturated or unsaturated 3 to 7 heteroring containing 1 to 2 nitrogen atoms, 0 or 1 sulfur atom or 0 or 1 oxygen atom, such as aziridine, azetidine, pyrrolidine, dihydropyrrole, piperidine, tetrahydropyridine, piperazine, thiazoline, thiazolidine, morpholine, thiomorpholine, azepane, tetrahydroazepine, tetrahydrodiazepine or hexahydrodiazepine. The preferable ones are azetidine, pyrrolidine, tetrahydropyridine, piperazine, thiazoline, thiazolidine, morpholine or thiomorpholine. The especially preferable ones are azetidine, pyrrolidine, tetrahydropyridine, thiazoline, thiazolidine or morpholine.

Substitution group in $R^2$ and $R^3$ includes, such as hydroxy group, $C_1$-$C_6$ alkyloxy, $C_1$-$C_6$ alkylthio, $C_2$-$C_7$ alkylcarbonyl, $C_2$-$C_7$ alkylcarbonyloxy, $C_2$-$C_7$ alkyloxycarbonyl, $C_3$-$C_7$ cycloalkyl, carboxyl, halogen atom, cyano, primary amino, secondary amino or tertiary amino. These substitution groups may be protected by a suitable protective group. The substitution position(s) are not limited as far as they are chemically possible. The position(s) can be single or plural.

"$C_1$-$C_6$ alkyloxy" includes, for example straight or branched $C_1$-$C_6$ alkoxy such as methoxy, ethoxy, n-propoxy, isopropoxy, n-butoxy, isobutoxy, tert-butoxy, n-pentyloxy or n-hexyloxy, preferably straight or branched $C_1$-$C_3$ alkoxy such as methoxy, ethoxy, n-propoxy or isopropoxy and especially preferable methoxy or ethoxy.

"$C_1$-$C_6$ alkylthio" includes for example, straight or branched $C_1$-$C_6$ alkylthio such as methylthio, ethylthio, n-propylthio, isopropylthio, n-butylthio, isobutylthio, tert-butylthio, n-pentylthio or n-hexylthio, preferably straight or branched $C_1$-$C_3$ alkylthio such as methylthio, ethylthio, n-propylthio or isopropylthio, and especially preferably methylthio or ethylthio.

"$C_2$-$C_7$ alkylcarbonyl" includes for example straight or branched $C_2$-$C_7$ alkylcarbonyl such as acetyl, propionyl, n-propylcarbonyl, isopropylcarbonyl, n-butylcarbonyl, isobutylcarbonyl, tert-butylcarbonyl, n-pentylcarbonyl or n-hexylcarbonyl, preferably straight or branched $C_2$-$C_4$ alkylcarbonyl such as acetyl, propionyl, n-propylcarbonyl or isopropylcarbonyl, and especially preferably acetyl or propionyl.

"$C_2$-$C_7$ alkylcarbonyloxy" includes for example, straight or branched $C_2$-$C_7$ alkylcarbonyloxy, such as acetyloxy, propionyloxy, n-propylcarbonyloxy, isopropylcarbonyloxy, n-butylcarbonyloxy, isobutylcarbonyloxy, tert-butylcarbonyloxy, n-pentylcarbonyloxy or n-hexylcarbonyloxy, preferably straight or branched $C_2$-$C_4$ alkylcarbonyloxy such as acetyloxy, propionyloxy, n-propylcarbonyloxy or isopropylcarbonyloxy and especially preferably acetyloxy or propionyloxy.

"$C_2$-$C_7$ alkyloxycarbonyl" includes for example, straight or branched $C_2$-$C_7$ alkyloxycarbonyl such as methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl or n-hexyloxycarbonyl, preferably straight or branched $C_2$-$C_4$ alkyloxycarbonyl such as methoxycarbonyl, ethoxycarbonyl, n-propoxycarbonyl or isopropoxycarbonyl and especially preferably methoxycarbonyl or ethoxycarbonyl.

"$C_3$-$C_7$ cycloalkyl" includes $C_3$-$C_7$ cycloalkyl such as cyclopropyl, cyclobutyl, cyclopentyl, cyclohexyl or cycloheptyl.

"Halogen atom" includes fluorine atom, chlorine atom, bromine atom or iodine atom, preferably fluorine atom or chlorine atom.

$R^2$ and $R^3$ include preferably hydrogen atom, optionally substituted $C_1$-$C_6$ alkyl, optionally substituted aryl which may contain hetero atom in its ring or optionally substituted aralkyl which may contain hetero atom in its ring, preferably hydrogen atom, optionally substituted methyl, optionally substituted ethyl, aryl which may contain hetero atom in its ring, or aralkyl which may contain hetero atom in its ring.

The signal "ma" in $Y^1$ is an integer of 1~3, preferably 1 or 2. The signal "mb" in $Y^1$ is an integer of 0~3, preferably 0 or 1.

"$C_1$-$C_4$ alkyl" in $Y^2$ includes such as methyl, ethyl, n-propyl, isopropyl, n-butyl, isobutyl or tert-butyl, preferably methyl, ethyl, n-propyl or isopropyl, and especially preferably methyl or ethyl.

"$C_1$-$C_4$ alkoxy" in $Y^2$ includes such as methoxy, ethoxy, n-propoxy, isopropoxy, n-butoxy, isobutoxy, sec-butoxy or tert-butoxy, preferably methoxy, ethoxy, n-propoxy or isopropoxy, and especially preferably methoxy or ethoxy.

"Halogen atom" in $Y^2$ includes fluorine atom, chlorine atom, bromine atom or iodine atom, preferably fluorine atom or chlorine atom. When $Y^2$ is —$NR^4R^5$, the definitions of $R^4$ and $R^5$ are as follows. As a protective group of amino group are used various protective groups usually used, preferably $C_2$-$C_7$ alkoxycarbonyl, such as tert-butoxycarbonyl, $C_1$-$C_5$ halogenoalkoxycarbonyl, such as 2-iodoethoxycarbonyl or 2,2,2-trichloroethoxycarbonyl, substituted or unsubstituted $C_2$-$C_7$ alkenyloxycarbonyl such as allyloxycarbonyl, aralkyloxycarbonyl such as benzyloxycarbonyl, p-methoxybenzyloxycarbonyl, o-nitrobenzyloxycarbonyl or p-nitrobenzyloxycarbonyl, or trialkylsilyl such as trimethylsilyl, triethylsilyl, tert-butyldimethylsilyl. Furthermore, various protective groups which reproduce amino group by hydrolysis in vivo can be used. The preferable one is for example, (5-methyl-1,3-dioxolene-2-one-4-yl)methoxycarbonyl.

"$C_1$-$C_6$ alkyl" moiety of "optionally substituted $C_1$-$C_6$ alkyl" includes for example, straight or branched $C_1$-$C_6$ alkyl such as methyl, ethyl, n-propyl, isopropyl, n-butyl, isobutyl, tert-butyl or n-pentyl, n-hexyl, preferably straight or branched $C_1$-$C_3$ alkyl such as methyl, ethyl, n-propyl or isopropyl, and especially preferably methyl or ethyl.

"$C_3$-$C_7$ cycloalkyl" moiety of "optionally substituted $C_3$-$C_7$ cycloalkyl" includes for example, $C_3$-$C_7$ cycloalkyl such as cyclopropyl, cyclobutyl, cyclopentyl, cyclohexyl or cycloheptyl.

"$C_2$-$C_7$ alkylcarbonyl" includes straight or branched $C_2$-$C_7$ alkylcarbonyl such as acetyl, propionyl, n-propylcarbonyl, isopropylcarbonyl, n-butylcarbonyl, isobutylcarbonyl, tert-butylcarbonyl, n-pentylcarbonyl or n-hexylcarbonyl, preferably acetyl or propionyl.

"Aryl" moiety of "optionally substituted aryl" includes such as phenyl or naphthyl, and especially preferably phenyl.

"Heteroaryl" moiety of "optionally substituted heteroaryl" includes, a 5 to 10 membered monocyclic or fused polycyclic aromatic ring containing 1 to 3 hetero atoms selected from nitrogen atom, oxygen atom and sulfur atom such as pyridyl, pyrimidinyl, pyridazinyl, thienyl, furyl, pyrrolyl, imidazolyl, oxazolyl, isoxazolyl, thiazolyl, isothiazolyl, triazolyl, indolyl, benzothiazolyl, quinazolinyl or isoquinazolinyl, preferably pyridyl, pyrimidinyl, pyridazinyl, pyrazinyl, thienyl, furyl, pyrrolyl, imidazolyl, oxazolyl, isoxazolyl, thiazolyl, isothiazolyl or triazolyl, and especially preferably pyridyl, pyrazinyl, thienyl, furyl, pyrrolyl, imidazolyl, oxazolyl, isoxazolyl or thiazolyl.

"Aralkyl" moiety of "optionally substituted aralkyl" includes for example, benzyl, phenylethyl or naphthylmethyl, preferably benzyl or phenylethyl.

"Heteroarylaliyl" moiety of "optionally substituted heteroarylalkyl" includes for example, a group consisting a combination of a $C_1$-$C_3$ alkylene chain and a 5 to 10 membered monocyclic or fused polycyclic aromatic ring containing 1 to 3 hetero atoms selected from nitrogen atom, oxygen atom and sulfur atom such as pyridylmethyl, pyrimidinylmethyl, pyridazinylmethyl, thienylmethyl, furylmethyl, pyrrolylmethyl, imidazolylmethyl, oxazolylmethyl, isoxazolylmethyl, thiazolylmethyl, isothiazolylmethyl, triazolylmethyl, indolylmethyl, benzothiazolylmethyl, quinazolinylmethyl, isoquinazolinylmethyl, pyridylethyl, pyrimidinylethyl, pyridazinylethyl, pyrazinylethyl or pyridylpropyl. The preferable ones are pyridylmethyl, pyrimidinylmethyl, pyridazinylmethyl, pyrazinylmethyl, thienylmethyl, furylmethyl, pyrrolylmethyl, imidazolylmethyl, oxazolylmethyl, isoxazolylmethyl, thiazolylmethyl, isothiazolylmethyl, triazolylmethyl, and especially preferably pyridylmethyl, pyrazinylmethyl, thienylmethyl, furylmethyl, pyrrolylmethyl, imidazolylmethyl, oxazolylmethyl, isoxazolylmethyl or thiazolylmethyl.

"A 3 to 7 membered hetero ring" formed with $R^4$ and $R^5$ includes for example, a saturated or unsaturated 3 to 7 heteroring containing 1 to 2 nitrogen atoms, 0 or 1 sulfur atom or 0 or 1 oxygen atom, such as aziridine, azetidine, pyrrolidine, dihydropyrrole, piperidine, tetrahydropyridine, piperazine, thiazoline, thiazolidine, morpholine, thiomorpholine, azepam, tetrahydroazepine, tetrahydrodiazepine or hexahydrodiazepine. The preferable one is azetidine, pyrrolidine, tetrahydropyridine, piperazine, thiazoline, thiazolidine, morpholine or thiomorpholine and especially preferably azetidine, pyrrolidine, tetrahydropyridine, thiazoline, thiazolidine or morpholine.

The substitution group of "optionally substituted $C_1$-$C_6$ alkyl", "optionally substituted $C_3$-$C_7$ cycloalkyl", "optionally substituted aryl", "optionally substituted heteroaryl", "optionally substituted aralkyl", "optionally substituted heteroarylalkyl" and "an optionally substituted 3 to 7 membered hetero ring" formed with $R^4$ and $R^5$, respectively includes hydroxy group, straight or branched $C_1$-$C_6$ alkoxy, such as methoxy, ethoxy, n-propoxy, isopropoxy, n-butoxy, isobutoxy, tert-butoxy, n-pentyloxy or n-hexyloxy, straight or branched $C_1$-$C_6$ alkylthio such as methylthio, ethylthio, n-propylthio, isopropylthio, n-butylthio, isobutylthio, tert-butylthio, n-pentylthio or n-hexylthio, straight or branched $C_2$-$C_7$ alkylcarbonyl, such as acetyl, propionyl, n-propylcarbonyl, isopropylcarbonyl, n-butylcarbonyl, isobutylcarbonyl, tert-butylcarbonyl, n-pentylcarbonyl or n-hexylcarbonyl, straight or branched $C_2$-$C_7$ alkylcarbonyloxy, such as acetyloxy, propionyloxy, n-propylcarbonyloxy, isopropylcarbonyloxy, n-butylcarbonyloxy, isobutylcarbonyloxy, tert-butylcarbonyloxy, n-pentylcarbonyloxy or n-hexylcarbonyloxy, straight or branched $C_2$-$C_7$ alkoxycarbonyl such as methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl or n-hexyloxycarbonyl, $C_3$-$C_7$ cycloalkyl such as cyclopropyl, cyclobutyl, cyclopentyl, cyclohexyl, cycloheptyl, optionally protected carboxyl, halogen atom such as fluorine atom, chlorine atom, bromine atom or iodide atom, cyano, —$NR^bR^c$, —$CONR^bR^c$, —$OCONR^bR^c$, —$CONR^bSO_2R^c$, —$SO_2NR^bR^c$, —$NR^bSO_2NR^bR^c$, or —$NR^bCONR^bR^c$ (in which $R^b$ and $R^c$ are independently (i) hydrogen atom, (ii) a protective group of amino group, (ii) $C_1$-$C_6$ alkyl, (iv) $C_3$-$C_7$ cycloalkyl, (v) aryl, (vi) heteroaryl, (vii) aralkyl, (viii) heteroarylalkyl, or (ix) a 3 to 7 membered hetero ring, or $R^b$ and $R^c$ are taken together with the nitrogen atom to form pyrrolidine, piperidine or azepane, and the definitions of "$C_1$-$C_6$ alkyl", "$C_3$-$C_7$ cycloalkyl", "aryl", "heteroaryl", "aralkyl", "heteroarylalkyl", and "a 3 to 7 membered hetero ring" in $R^b$ and $R^c$ are the same as the definitions of $R^4$ and $R^5$).

These substitution groups may be protected with a suitable protective group. The substitution position(s) are not limited as far as these are chemically possible, and are single or plural.

When $R^0$ is the formula [2], the definitions of $R^{2a}$ and $R^{3a}$ are as follows.

"$C_1$-$C_6$ alkyl" moiety of "optionally substituted $C_1$-$C_6$ alkyl" includes for example, straight or branched $C_1$-$C_6$ alkyl such as methyl, ethyl, n-propyl, isopropyl, n-butyl, isobutyl, tert-butyl, n-pentyl or n-hexyl, preferably straight or branched $C_1$-$C_3$ alkyl such as methyl, ethyl, n-propyl or isopropyl, and especially preferably methyl or ethyl.

"$C_3$-$C_7$ cycloalkyl" moiety of "optionally substituted $C_3$-$C_7$ cycloalkyl" includes for example, $C_3$-$C_7$ cycloalkyl such as cyclopropyl, cyclobutyl, cyclopentyl, cyclohexyl or cycloheptyl.

"Aryl" of "optionally substituted aryl" includes such as phenyl or naphthyl, and especially preferably phenyl.

"Heteroaryl" of "optionally substituted heteroaryl" includes for example, a 5 to 10 membered monocyclic or fused polycyclic aromatic ring containing 1 to 3 hetero atoms selected from nitrogen atom, oxygen atom and sulfur atom such as pyridyl, pyrimidinyl, pyridazinyl, pyrazinyl, thienyl, furyl, pyrrolyl, imidazolyl, oxazolyl, isoxazolyl, thiazolyl, isothiazolyl, triazolyl, indolyl, benzothiazolyl, quinazolinyl or isoquinazolinyl, preferably pyridyl, pyrimidinyl, pyridazinyl, pyrazinyl, thienyl, furyl, pyrrolyl, imidazolyl, oxazolyl, isoxazolyl, thiazolyl, isothiazolyl or triazolyl, and especially preferably pyridyl, pyrazinyl, thienyl, furyl, pyrrolyl, imidazolyl, oxazolyl, isoxazolyl or thiazolyl.

"Aralkyl" moiety of "optionally substituted aralkyl" includes such as benzyl, phenylethyl or naphthylmethyl, preferably benzyl or phenylethyl.

"Heteroarylalkyl" moiety of "optionally substituted heteroarylalkyl" includes for example, a group consisting a combination of a $C_1$-$C_3$ alkylene chain and a 5 to 10 membered monocyclic or fused polycyclic aromatic ring containing 1 to 3 hetero atoms selected from nitrogen atom, oxygen atom and sulfur atom such as pyridylmethyl, pyrimidinylmethyl, pyridazinylmethyl, pyrazinylmethyl, thienylmethyl, furylmethyl, pyrrolylmethyl, imidazolylmethyl, oxazolylmethyl, isoxazolylmethyl, thiazolylmethyl, isothiazolylmethyl, triazolylmethyl, indolylmethyl, benzothiazolylmethyl, quinazolinylmethyl, isoquinazolinylmethyl, pyridylethyl, pyrimidinylethyl, pyridazinylethyl, pyrazinylethyl or pyridylpropyl. The preferable ones are pyridylmethyl, pyrimidinylmethyl, pyridazinylmethyl, pyrazinylmethyl, thienylmethyl, furylmethyl, pyrrolylmethyl, imidazolylmethyl, oxazolylmethyl, isoxazolylmethyl, thiazolylmethyl, isothiazolylmethyl or triazolylmethyl, and especially preferably pyridylmethyl, pyrazinylmethyl, thienylmethyl, furylmethyl, pyrrolylmethyl, imidazolylmethyl, oxazolylmethyl, isoxazolylmethyl or thiazolylmethyl.

"A 3 to 7 membered hetero ring" and "an optionally substituted 3 to 7 membered hetero ring" formed with $R^{2a}$ and $R^{3a}$ includes, for example, a saturated or unsaturated 3 to 7 hetero ring containing 1 to 2 nitrogen atoms, 0 or 1 sulfur atom or 0 or 1 oxygen atom, such as aziridine, azetidine, pyrrolidine, dihydropyrrole, piperidine, tetrahydropyridine, piperazine, thiazoline, thiazolidine, morpholine, thiomorpholine, azepane, tetrahydroazepine, tetrahydrodiazepine or hexahydrodiazepine. The preferred one is azetidine, pyrrolidine, tetrahydropyridine, piperazine, thiazoline, thiazolidine, morpholine or thiomorpholine, and especially preferably azetidine, pyrrolidine, tetrahydropyridine, thiazoline, thiazolidine or morpholine.

The substitution group of "optionally substituted $C_1$-$C_6$ alkyl", "optionally substituted $C_3$-$C_7$ cycloalkyl", "optionally substituted aryl", "optionally substituted heteroaryl", "an optionally substituted aralkyl", "optionally substituted heteroarylalkyl" and "optionally substituted 3 to 7 membered hetero ring" formed with $R^{2a}$ and $R^{3a}$, respectively includes hydroxy group, straight or branched $C_1$-$C_6$ alkoxy, such as methoxy, ethoxy, n-propoxy, isopropoxy, n-butoxy, isobutoxy, tert-butoxy, n-pentyloxy or n-hexyloxy, straight or branched $C_1$-$C_6$ alkylthio such as methylthio, ethylthio, n-propylthio, isopropylthio, n-butylthio, isobutylthio, tert-butylthio, n-pentylthio or n-hexylthio, straight or branched $C_2$-$C_7$ alkylcarbonyl, such as acetyl, propionyl, n-propylcarbonyl, isopropylcarbonyl, n-butylcarbonyl, isobutylcarbonyl, tert-butylcarbonyl, n-pentylcarbonyl or n-hexylcarbonyl, straight or branched $C_2$-$C_7$ alkylcarbonyloxy, such as acetyloxy, propionyloxy, n-propylcarbonyloxy, isopropylcarbonyloxy, n-butylcarbonyloxy, isobutylcarbonyloxy, tert-butylcarbonyloxy, n-pentylcarbonyloxy or n-hexylcarbonyloxy, straight or branched $C_2$-$C_7$ alkoxycarbonyl such as methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl or n-hexyloxycarbonyl, $C_3$-$C_7$ cycloalkyl such as cyclopropyl, cyclobutyl, cyclopentyl, cyclohexyl or cycloheptyl, optionally protected carboxyl, halogen atom such as fluorine atom, chlorine atom, bromine atom or iodide atom, cyano, —$NR^dR^e$, —$CONR^dR^e$, —$OCONR^dR^e$, —$CONR^dSO_2R^e$, —$SO_2NR^dR^e$, —$NR^dSO_2NR^dR^e$, or —$NR^dCONR^dR^e$ (in which $R^d$ and $R^e$ are independently (i) hydrogen atom, (ii) a protective group of amino group, (iii) $C_1$-$C_6$ alkyl, (iV) $C_3$-$C_7$ cycloalkyl, (v) aryl, (vi) heteroaryl, (vii) aralkyl, (viii) heteroarylalkyl, or (ix) a 3 to 7 membered hetero ring, or $R^b$ and $R^c$ are taken together with the nitrogen atom to form pyrrolidine, piperidine or azepane, and the definitions of "$C_1$-$C_6$ alkyl", "$C_3$-$C_7$ cycloalkyl", "aryl", "heteroaryl", "aralkyl", "heteroarylalkyl", and "a 3 to 7 membered hetero ring" in $R^d$ and $R^e$ are the same as the definitions of $R^{2a}$ and $R^{3a}$.). These substituents may be protected with a suitable protective group. The substitution position(s) are not limited as far as these are chemically possible, and are single or plural.

When $R^0$ is the formula [3], the definition of $R^{3a}$ is as follows.

"$C_1$-$C_6$ alkyl" moiety of "optionally substituted $C_1$-$C_6$ alkyl" includes for example, straight or branched $C_1$-$C_6$ alkyl such as methyl, ethyl, n-propyl, isopropyl, n-butyl, isobutyl, tert-butyl, n-pentyl or n-hexyl, preferably straight or branched $C_1$-$C_3$ alkyl such as methyl, ethyl, n-propyl or isopropyl and especially preferably methyl or ethyl.

"$C_3$-$C_7$ cycloalkyl" moiety of "optionally substituted $C_3$-$C_7$ cycloalkyl" includes for example, $C_3$-$C_7$ cycloalkyl such as cyclopropyl, cyclobutyl, cyclopentyl, cyclohexyl or cycloheptyl.

"Aryl" of "optionally substituted aryl" includes such as phenyl or naphthyl, and especially preferably phenyl.

"Heteroaryl" of "optionally substituted heteroaryl" includes for example, a 5 to 10 membered monocyclic or fused polycyclic aromatic ring containing 1 to 3 hetero atoms selected from nitrogen atom, oxygen atom and sulfur atom such as pyridyl, pyrimidinyl, pyridazinyl, pyrazinyl, thienyl, furyl, pyrrolyl, imidazolyl, oxazolyl, isoxazolyl, thiazolyl, isothiazolyl, triazolyl, indolyl, benzothiazolyl, quinazolinyl or isoquinazolinyl, preferably pyridyl, pyrimidinyl, pyridazinyl, pyrazinyl, thienyl, furyl, pyrrolyl, imidazolyl, oxazolyl, isoxazolyl, thiazolyl, isothiazolyl or triazolyl, and especially preferably pyridyl, pyrazinyl, thienyl, furyl, pyrrolyl, imidazolyl, oxazolyl, isoxazolyl or thiazolyl.

"Aralkyl" moiety of "optionally substituted aralkyl" includes such as benzyl, phenylethyl or naphthylmethyl, preferably benzyl or phenylethyl.

"Heteroarylalkyl" moiety of "optionally substituted heteroarylalkyl" includes for example, a group consisting a combination of a $C_1$-$C_3$ alkylene chain and a 5 to 10 membered monocyclic or fused polycyclic aromatic ring containing 1 to 3 hetero atoms selected from nitrogen atom, oxygen atom and sulfur atom such as pyridylmethyl, pyrimidinylmethyl, pyridazinylmethyl, pyrazinylmethyl, thienylmethyl, furylmethyl, pyrrolylmethyl, imidazolylmethyl, oxazolylmethyl, isoxazolylmethyl, thiazolylmethyl, isothiazolylmethyl, triazolylmethyl, indolylmethyl, benzothiazolylmethyl, quinazolinylmethyl, isoquinazolinylmethyl, pyridylethyl, pyrimidinylethyl, pyridazinylethyl, pyrazinylethyl or pyridylpropyl. The preferable one is pyridylmethyl, pyrimidinylmethyl, pyridazinylmethyl, pyrazinylmethyl, thienylmethyl, furylmethyl, pyrrolylmethyl, imidazolylmethyl, oxazolylmethyl, isoxazolylmethyl, thiazolylmethyl, isothiazolylmethyl or triazolylmethyl, and especially preferably pyridylmethyl, pyrazinylmethyl, thienylmethyl, furylmethyl, pyrrolylmethyl, imidazolylmethyl, oxazolylmethyl, isoxazolylmethyl or thiazolylmethyl.

"A 3 to 7 membered hetero ring" of "an optionally substituted 3 to 7 membered hetero ring" includes, for example, a saturated or unsaturated 3 to 7 heteroring containing 1 to 2 nitrogen atoms, 0 or 1 sulfur atom or 0 or 1 oxygen atom, such as aziridine, azetidine, pyrrolidine, dihydropyrrole, tetrahydropyridine, piperidine, piperazine, thiazoline, thiazolidine, morpholine, thiomorpholine, azepane, tetrahydroazepine, tetrahydrodiazepine, or hexahydrodiazepine. The preferred one is azetidine, pyrrolidine, tetrahydropyridine, piperazine, thiazoline, thiazolidine, morpholine or thiomorpholine, and especially preferably azetidine, pyrrolidine, tetrahydropyridine, thiazoline, thiazolidine or morpholine.

The substitution group of "optionally substituted $C_1$-$C_6$ alkyl", "optionally substituted $C_3$-$C_7$ cycloalkxyl", "optionally substituted aryl", "optionally substituted heteroaryl", "optionally substituted aralkyl", "optionally substituted heteroarylalkyl" and "optionally substituted 3 to 7 membered hetero ring" in $R^{3b}$, respectively includes hydroxy group, straight or branched $C_1$-$C_6$ alkoxy, such as methoxy, ethoxy, n-propoxy, isopropoxy, n-butoxy, isobutoxy, tert-butoxy, n-pentyloxy or n-hexyloxy, straight or branched $C_1$-$C_6$ alkylthio such as methylthio, ethylthio, n-propylthio, isopropylthio, n-butylthio, isobutylthio, tert-butylthio, n-pentylthio or n-hexylthio, straight or branched $C_2$-$C_7$ alkylcarbonyl, such as acetyl, propionyl, n-propylcarbonyl, isopropylcarbonyl, n-butylcarbonyl, isobutylcarbonyl, tert-butylcarbonyl, n-pentylcarbonyl or n-hexylcarbonyl, straight or branched $C_2$-$C_7$ alkylcarbonyloxy, such as acetyloxy, propionyloxy, n-propylcarbonyloxy, isopropylcarbonyloxy, n-butylcarbonyloxy, isobutylcarbonyloxy, tert-butylcarbonyloxy, n-pentylcarbonyloxy or n-hexylcarbonyloxy, straight or branched $C_2$-$C_7$ alkoxycarbonyl such as methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl or n-hexyloxycarbonyl, $C_3$-$C_7$ cycloalkyl such as cyclopropyl, cyclobutyl, cyclopentyl, cyclohexyl or cycloheptyl, optionally protected carboxyl, halogen atom such as fluorine atom, chlorine atom, bromine atom or iodide atom, cyano, —$NR^dR^e$, —$CONR^dR^e$, —$OCONR^dR^e$, —$CONR^dSO_2R^e$, —$SO_2NR^dR^e$, —$NR^dSO_2NR^dR^e$, or —$NR^cCONR^dR^e$ (in which $R^d$ and $R^e$ are the same as defined above). These substitution groups may be protected with a suitable protective group. The substitution position(s) are not limited as far as these are chemically possible, and are single or plural.

"A group which reproduces carboxyl group by hydrolysis in vivo" in $R^{3b}$ which is possible only in the case that m is 1 includes any group as far as it reproduces carboxyl group by hydrolysis in vivo, and means the group used when derived into the compound called a prodrug. The preferable ones are $C_1$-$C_6$ alkyl, such as, methyl or ethyl, $C_2$-$C_{12}$ alkoxyalkyl, such as methoxymethyl, ethoxymethyl, 2-methoxyethyl, 2-methoxyethoxymethyl, phthalidyl, 2-(4-morpholinyl)ethyl,(2-oxo-1,3-dioxol-4-yl)methyl, (5-methyl-2-oxo-1,3-dioxol-4-yl)methyl, (5-t-butyl-2-oxo-1,3-dioxol-4-yl)methyl, (5-phenyl-2-oxo-1,3-dioxol-4-yl)methyl, pivaloyloxymethyl, acetyloxymethyl, acetyloxyl-ethyl, cyclohexylacetyloxymethyl, 1-methylcyclohexylcarbonyloxymethyl, ethoxycarbonyloxyl-ethyl or cyclohexyloxycarbonyloxyl-ethyl, especially preferably, phthalidyl or (5-methyl-2-oxo-1,3-dioxol-4-yl)methyl, pivaloyloxymethyl.

When A is —$(CH_2)_s$—$NR^a$—$(CH_2)_t$—(in which s and t are the same as defined above, $R^a$ is hydrogen atom, a protective group of amino group or optionally substituted $C_1$-$C_6$ alkyl), a protective group of amino group in $R^a$ includes various protective groups usually used, preferably such as $C_2$-$C_7$ alkoxycarbonyl such as tert-butoxycarbonyl, $C_1$-$C_5$ halogenoalkoxycarbonyl such as 2-iodoethoxycarbonyl or 2,2,2-trichloroethoxycarbonyl, substituted or unsubstituted $C_2$-$C_7$ alkenyloxycarbonyl such as allyloxycarbonyl, aralkyloxycarbonyl such as benzyloxycarbonyl, p-methoxybenzyloxycarbonyl, o-nitrobenzyloxycarbonyl or p-nitrobenzyloxycarbonyl, or trialkylsily such as trimethylsilyl, triethylsilyl or tert-butyldimethylsilyl. Furthermore, various protective groups which reproduce amino group by hydrolysis in vivo can be used. The preferable one is for example, (5-methyl-1,3-dioxolene-2-one-4-yl)methoxycarbonyl.

"$C_1$-$C_6$ alkyl" includes for example, straight or branched $C_1$-$C_6$ alkyl such as methyl, ethyl, n-propyl, isopropyl, n-butyl, isobutyl, tert-butyl, n-pentyl or n-hexyl, preferably straight or branched $C_1$-$C_3$ alkyl such as methyl, ethyl, n-propyl or isopropyl, and especially preferably methyl or ethyl.

The substituted group of "optionally substituted $C_1$-$C_6$ alkyl" in $R^a$ includes hydroxy group, straight or branched $C_1$-$C_6$ alkoxy, such as methoxy, ethoxy, n-propoxy, isopropoxy, n-butoxy, isobutoxy, tert-butoxy, n-pentyloxy or n-hexyloxy, straight or branched $C_1$-$C_6$ alkylthio such as methylthio, ethylthio, n-propylthio, isopropylthio, n-butylthio, isobutylthio, tert-butylthio, n-pentylthio or n-hexylthio, straight or branched $C_2$-$C_7$ alkylcarbonyl, such as acetyl, propionyl, n-propylcarbonyl, isopropylcarbonyl, n-butylcarbonyl, isobutylcarbonyl, tert-butylcarbonyl, n-pentylcarbonyl or n-hexylcarbonyl, straight or branched $C_2$-$C_7$ alkylcarbonyloxy, such as acetyloxy, propionyloxy, n-propylcarbonyloxy, isopropylcarbonyloxy, n-butylcarbonyloxy, isobutylcarbonyloxy, tert-butylcarbonyloxy, n-pentylcarbonyloxy or n-hexylcarbonyloxy, straight or branched $C_2$-$C_7$ alkoxycarbonyl such as methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl or n-hexyloxycarbonyl, $C_3$-$C_7$ cycloalkyl such as cyclopropyl, cyclobutyl, cyclopentyl, cyclohexyl or cycloheptyl, optionally protected carboxyl, halogen atom such as fluorine atom, chlorine atom, bromine atom or iodide atom, cyano, —$NR^dR^e$, —$CONR^dR^e$, —$OCONR^dR^e$, —$CONR^dSO_2R^e$, —$SO_2NR^dR^e$, —$NR^dSO_2NR^dR^e$, or —$NR^dCONR^dR^e$ (in which $R^d$ and $R^e$ are the same as defined above).

The signal "r" in A is an integer of 1~3, preferably 1, 2.
The signal "s" in A is an integer of 1~3, preferably 0, 1, 2.
The signal "t" in A is an integer of 1~3, preferably 0, 1, 2.

"A group which reproduces carboxyl group by hydrolysis in vivo" in R includes any group as far as it reproduces carboxyl group by hydrolysis in vivo, and means the group used when derived into the compound called a prodrug. The preferable group is a formula [4]:

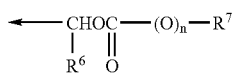

[4]

wherein $R^6$, $R^7$ and n are the same as defined above.

"$C_1$-$C_6$ alkyl" in $R^6$ includes for example, straight or branched $C_1$-$C_6$ alkyl such as methyl, ethyl, n-propyl, isopropyl, n-butyl, isobutyl, tert-butyl, n-pentyl or n-hexyl, and preferably methyl.

"$C_1$-$C_{10}$ alkyl" in $R^7$ includes straight or branched $C_1$-$C_{10}$ alkyl such as methyl, ethyl, n-propyl, isobutyl, tert-butyl, n-pentyl, n-hexyl, n-heptyl, n-octyl, n-nonyl or n-decyl, and preferably, methyl, ethyl, n-propyl, isobutyl, tert-butyl, n-pentyl or n-hexyl.

"$C_3$-$C_{10}$ cycloalkyl" in $R^7$ includes such as cyclopropyl, cyclobutyl, cyclopentyl, cyclohexyl, cycloheptyl, cyclooctyl, cyclononyl or cyclodecyl, and preferably, cyclopropyl, cyclobutyl, cyclopentyl or cyclohexyl.

The substitution group of "optionally substituted $C_1$-$C_{10}$ alkyl" and "optionally substituted $C_3$-$C_{10}$ cycloalkyl" in $R^7$ includes straight or branched $C_1$-$C_6$ alkyl such as methyl, ethyl, n-propyl, isobutyl, tert-butyl, n-pentyl or n-hexyl, and preferably, methyl or ethyl. The preferable one of the formula [4] is pivaloyloxymethyl, acetyloxymethyl, acetyloxyl-ethyl, cyclohexylacetyloxymethyl, 1-methylcyclohexylcarbonyloxymethyl, ethoxycarbonyloxyl-ethyl or cyclohexyloxycarbonyloxyl-ethyl, and especially preferably pivaloyloxymethyl.

Other example of "a group which reproduces carboxyl group by hydrolysis in vivo" in R is $C_1$-$C_6$ alkyl such as methyl or ethyl, $C_2$-$C_{12}$ alkoxyalkyl such as methoxymethyl, ethoxymethyl, 2-methoxyethyl, 2-methoxyethoxymethyl, phthalidyl, 2-(4-morpholinyl)ethyl, (2-oxo-1,3-dioxol-4-yl) methyl, (5-methyl-2-oxo-1,3-dioxol-4-yl)methyl, (5-t-butyl-2-oxo-1,3-dioxol-4-yl)methyl or (5-phenyl-2-oxo-1,3-dioxol-4-yl)methyl, and especially preferably, phthalidyl or (5-methyl-2-oxo-1,3-dioxol-4-yl)methyl.

The protective group of carboxyl includes various protective groups usually used, preferably straight or branched $C_1$-$C_6$ alkyl, such as methyl, ethyl, isopropyl or tert-butyl, $C_1$-$C_6$ halogenoalkyl, such as 2-iodoethyl or 2,2,2-trichloroethyl, $C_2$-$C_7$ alkoxymethyl such as methoxymethyl, ethoxymethyl or isobutoxymethyl, $C_2$-$C_7$ alkylcarbonyloxymethyl such as acetyloxymethyl, propionyloxymethyl, butyryloxymethyl or pivaloyloxymethyl, $C_4$-$C_{11}$ 1-alkoxycarbonyloxyethyl such as 1-ethoxycarbonyloxyethyl, aralkyl group such as benzyl, p-methoxybenzyl, o-nitrobenzyl or p-nitrobenzyl, $C_3$-$C_7$ alkenyl such as allyl or 3-methylallyl, benzhydryl, phthalidyl, (2-oxo-1,3-dioxol-4-yl)methyl, (5-methyl-2-oxo-1,3-dioxol-4-yl)methyl, (5-t-butyl-2-oxo-1,3-dioxol-4-yl)methyl, or (5-phenyl2-oxo-1,3-dioxol-4-yl) methyl.

The protective group of hydroxy group or amino group includes various protective groups usually used, preferably for example, $C_2$-$C_7$ alkoxycarbonyl, such as tert-butoxycarbonyl, $C_1$-$C_5$ halogenoalkoxycarbonyl such as 2-iodoethoxycarbonyl or 2,2,2-trichloroethoxycarbonyl, substituted or unsubstituted $C_2$-$C_7$ alkenyloxycarbonyl such as allyloxycarbonyl, aralkyloxycarbonyl such as benzyloxycarbonyl, p-methoxybenzyloxycarbonyl, o-nitrobenzyloxycarbonyl or p-nitrobenzyloxycarbonyl, or trialkylsily such as trimethylsilyl, triethylsilyl or tert-butyldimethylsilyl. Furthermore, various protective groups which reproduce hydroxy group and/or amino group by hydrolysis in vivo can be used, preferably for example, (5-methyl-1,3-dioxolene-2-one-4-yl) methoxycarbonyl can be used.

The pharmaceutically acceptable salt of the carbapenem compound of the present invention is a conventional non-toxic salt. Such a salt includes, as a salt with a carboxyl group in the molecule, a salt with an inorganic base such as sodium, potassium, calcium or magnesium, ammonium, or a salt with an organic base such as triethylammonium, pyridinium or diisopropylammonium. As a salt with a basic group in the molecule, a salt with an inorganic acid such as hydrochloric acid, sulfuric acid or phosphoric acid, or a salt with an organic acid such as formic acid, acetic acid, oxalic acid, methanesulfonic acid or benzenesulfonic acid can be exemplified.

The pharmaceutically acceptable salt of the carbapenem compound of the present invention may be in the form of an anhydride thereof, or a hydrate thereof, or a solvate thereof.

The second aspect of the present invention relates to a pharmaceutical composition containing a carbapenem compound as an active ingredient.

Since the carbapenem compound of the present invention has a potent antibacterial activity, excellent oral absorbability and furthermore, has stability to DHP-1, the compound is expected as a potent antibacterial agent which is clinically applicable, especially an orally antibacterial agent.

The carbapenem compound of the present invention exhibits broad antibacterial spectrum including gram positive bacteria, such as *Staphylococcus aureus, Staphylococcus epidermidis, Streptococcus pyogenes, Streptococcus pneumoniae, Enterococcus faecalis*, etc., and gram negative bacteria, such as *Escherichia coli*, the genus *Proteus, Klebsiella pneumoniae, Haemophilus influenzae, Neisseria gonorrhea*, the genus *Branhamella*, etc. The carbapenem compound of the present invention has been found to have a potent antibacterial activity especially against penicillin resistant *Streptococcus pneumoniae* (PRSP) or *Haemophilus influenzae* (which widely gain resistance to known β-lactam agents by mutation of a penicillin binding protein (PBP) such as β-lactamase non-producing ampicillin resistant *Haemophilus influenzae*

(BLNAR), which have been recently increasingly isolated and provide a clinical trouble.).

It is well known that dehydropeptidase-I (DHP-I), a renal enzyme can easily hydrolyze a carbapenem derived from natural sources. Some of the present carbapenem compounds show resistance to DHP-I and it is possible to use them solely. However, it is possible to use the compound of the present invention together with a DHP-I inhibitor, if necessary.

When used as an antibacterial agent in the treatment of infectious diseases caused by bacteria, the carbapenem compounds of the present invention are administered, for example, orally in the form of a tablet, a capsule, powders, syrup, etc. or parenterally such as intravenous injection, intramuscular injection, or intrarectal administration.

The suitable administration forms as mentioned above may be prepared in a conventional manner by mixing an active ingredient with a pharmaceutically acceptable carrier, excipient, binder, stabilizer, etc. When administered in the form of injection, a pharmaceutically acceptable buffering agent, solubilizer, isotonic agent, etc. may be added thereto.

The dosage of the compound varies according to the symptoms, ages, body weights, the administration form, the frequency of the administration, etc., but it is usually in the range of 100 to 3000 mg per day for an adult, which is administered once or divided into several dosage units. Besides, the dosage of the compound may be increased or decreased, if necessary.

The carbapenem compound of the present invention is prepared by various known methods (Tetrahedron, 39, 2531-2549 (1983), Tetrahedron Letters, 31, 2853-2856 (1990), ibid. 34, 3211-3214 (1993), ibid. 36, 4563-4566 (1995), Japanese patent publication B 4-40357, WO 02/053566, WO 03/040146, WO 03/089431, etc.). One of these methods, for example is illustrated as follows:

The compound of the formula [1-a] is prepared by for example, process (1) mentioned below.

Process (1)

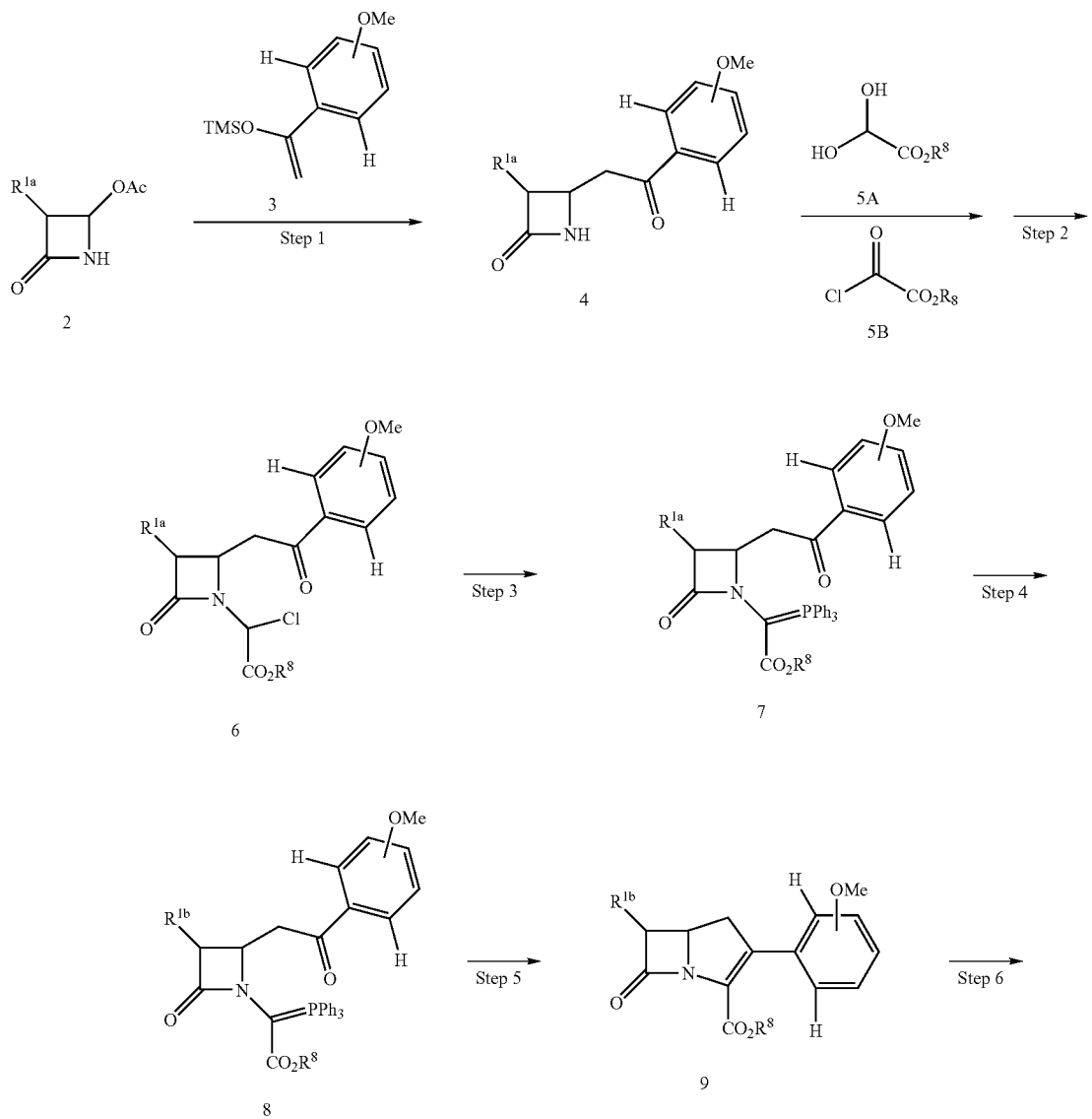

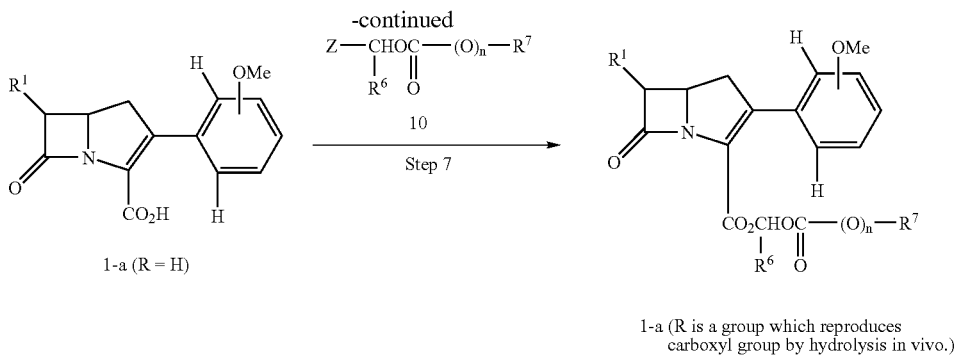

1-a (R = H)

1-a (R is a group which reproduces carboxyl group by hydrolysis in vivo.)

In the above formulas, $R^1$, $R^6$ and $R^7$ are the same as defined above, $R^8$ is a protective group of carboxyl group or group which reproduces carboxyl group by hydrolysis in vivo, $R^{1a}$ and $R^{1b}$ are independently $C_1$-$C_3$ alkyl group or $C_1$-$C_3$ alkyl substituted by protected hydroxy group. Z is chlorine atom, bromine atom or iodine atom.

Step 1: Process for Preparation of Compound 4

Compound 4 is prepared by reacting compound 2 and compound 3 in the presence of acid catalyst in an inert solvent. The acid catalyst includes zinc chloride, zinc bromide, zinc iodide, tin tetrachloride, trifluoromethanesulfonic acid trimethylsilyl ester or boron trifluoride-diethyl ether complex.

The inert solvent includes dichloromethane, 1,2-dichloroethane, acetonitrile, monochlorobenzene, dioxane, tetrahydrofuran, benzene or toluene.

The reaction is carried out at −78° C. to 60° C., preferably at −30° C. to 40° C. The starting compound 3 is prepared by enol-etherification of various acetophenone derivatives prepared by known methods (e.g. Synthesis and reaction of organic compound [II] page 751-875 (1977), Sin Jikken Kagaku Kouza edited by The Chemical Society of Japan, Vol. 14 (Maruzen), or Organic Synthesis [III], Aldehyde-Ketone-Quinone, page 149-353 (1991), Sin Jikken Kagaku Kouza edited by The Chemical Society of Japan, 4th Edition (Maruzen)).

Step 2: Process for Preparation of Compound 6

Corresponding hemiacetal is prepared by heating compound 4 and compound 5A under dehydrating condition in an inert solvent. The inert solvent includes dichloromethane, 1,2-dichloroethane, monochlorobenzene, benzene, toluene or xylene. The reaction was carried out at 50° C. to 200° C., preferably at 80° C. to 150° C. In accordance of the known method (the Journal of Organic Chemistry, 61, 7889-7894 (1996)) the corresponding hemiacetal compound is also prepared by reacting compound 4 and compound 5B in the presence of a base in an inert solvent, followed by reduction to give an imido compound. The base includes triethylamine, diisopropylethylamine or N-methylmorpholine. The inert solvent for imidation includes dichloromethane, 1,2-dichloroethane or monochiorobenzene. The imidation was carried out at −50° C. to 50° C., preferably at −30° C. to 30° C., The preferable reducing agent is zinc and the reduction is carried out in a mixed solvent such as acetic acid and dichloromethane, acetic acid and 1,2-dichloroethane, and acetic acid and monochlorobenzene at −50° C. to 50° C., preferably at −30° C. to 30° C.

Thus obtained hemiacetal compound is chlorinated using a chlorinating agent such as thionyl chloride, oxalyl chloride or phosphorous oxychloride. The chlorination is conducted in an inert solvent such as ether, tetrahydrofuran or dichloromethane, in the presence of a base such as lutidine, pyridine, quinoline, diisopropylethylamine or triethylamine at −78° C. to 60° C., preferably at −30° C. to 40° C.

Step 3: Process for Preparation of Compound 7

Compound 7 is prepared by reacting compound 6 and triphenylphosphine in an inert solvent such as tetrahydrofuran, dioxane, or dimethoxyethane in the presence of a base such as lutidine, pyridine, quinoline, dilsopropylethylamine or triethylamine at 0° C. to 100° C., preferably at 10° C. to 70° C.

Step 4: Process for Preparation of Compound 8

If necessary, the protective group of hydroxy group in $R^{1a}$ is removed and followed by reprotection. The removal of the protective group and protection are known (for example, see T. W. Greene, P. G. M. Wuts: Protective Groups in Organic Synthesis; 3rd ed., Wiley, New York (1999), or P. Kocienski, Protecting Groups, Thieme, Stuttgart (1994)).

Step 5: Process for Preparation of Compound 9

Compound 9 is prepared by cyclizing compound 8 in an inert solvent such as benzene, toluene or xylene at 80° C. to 200° C.

Step 6: Process for Preparation of Compound [1-a] (R is Hydrogen Atom)

Carbapenem compound [1-a] (R is hydrogen atom) is prepared by removing a protective group of carboxyl group in $R^8$ of compound 9, or removing a protective group of hydroxy group when $R^{1b}$ is a protective group of hydroxy group. The removal of the protective group is carried out by known method such as treating with acid base, reduction agent (see T. W. Greene, P. G. M. Wuts: Protective Groups in Organic Synthesis; 3rd ed., Wiley, New York (1999), or P. Kocienski, Protecting Groups, Thieme, Stuttgart (1994)).

Step 7: Process for Preparation of Compound [1-a] (R is a Group which Reproduces Carboxyl group by Hydrolysis in Vivo)

Compound [1-a] (R is a group which reproduces carboxyl group by hydrolysis in vivo) is prepared by introducing using a conventional method, a group which reproduces carboxyl group by hydrolysis in vivo into carbapenem compound [1-a] (R is hydrogen atom). For example, carbapenem compound [1-a] (R is hydrogen atom) or its carboxylic acid salt is reacted with various halides of the compound 10, if necessary, in the presence of a base such as diisopropylethylamine, triethylamine, 4-dimethylaminopyridine, potassium carbonate or sodium hydrogencarbonate, or phase transfer catalyst such as triethylbenzylammoniun chloride or tetrabutylammonium bromide. The reaction solvent is not limited as far as it is inert and preferably dimethylformamide, dimethyl sulfoxide, hexamethylphosphoramide, acetonitrile, dioxane, tetrahydrofuran or acetone. The carboxylic acid salt includes preferably its sodium or potassium salt. The reaction is carried out at −78° C. to 100° C., preferably −20° C. to 60° C. Furthermore, in step 2, using compound 5A or 5B having a group which reproduces carboxyl group by hydrolysis in vivo in $R^8$, and then, via each step, carbapenem compound [1-a] (R is a group which reproduces carboxyl group by hydrolysis in vivo) can be directly prepared.

In the above steps, after reaction the product is isolate by the method according to organic chemistry, and when the product is water soluble, the reaction mixture is adjusted to around neutralization and is subjected to column chromatography using absorption resin, etc. and the fractions containing the object compound are taken and lyophilized to the object compound.

The compound of the formula [1-b] is prepared in accordance of process (1).

The compound of the formula [1-c] is prepared, for example by process (2).

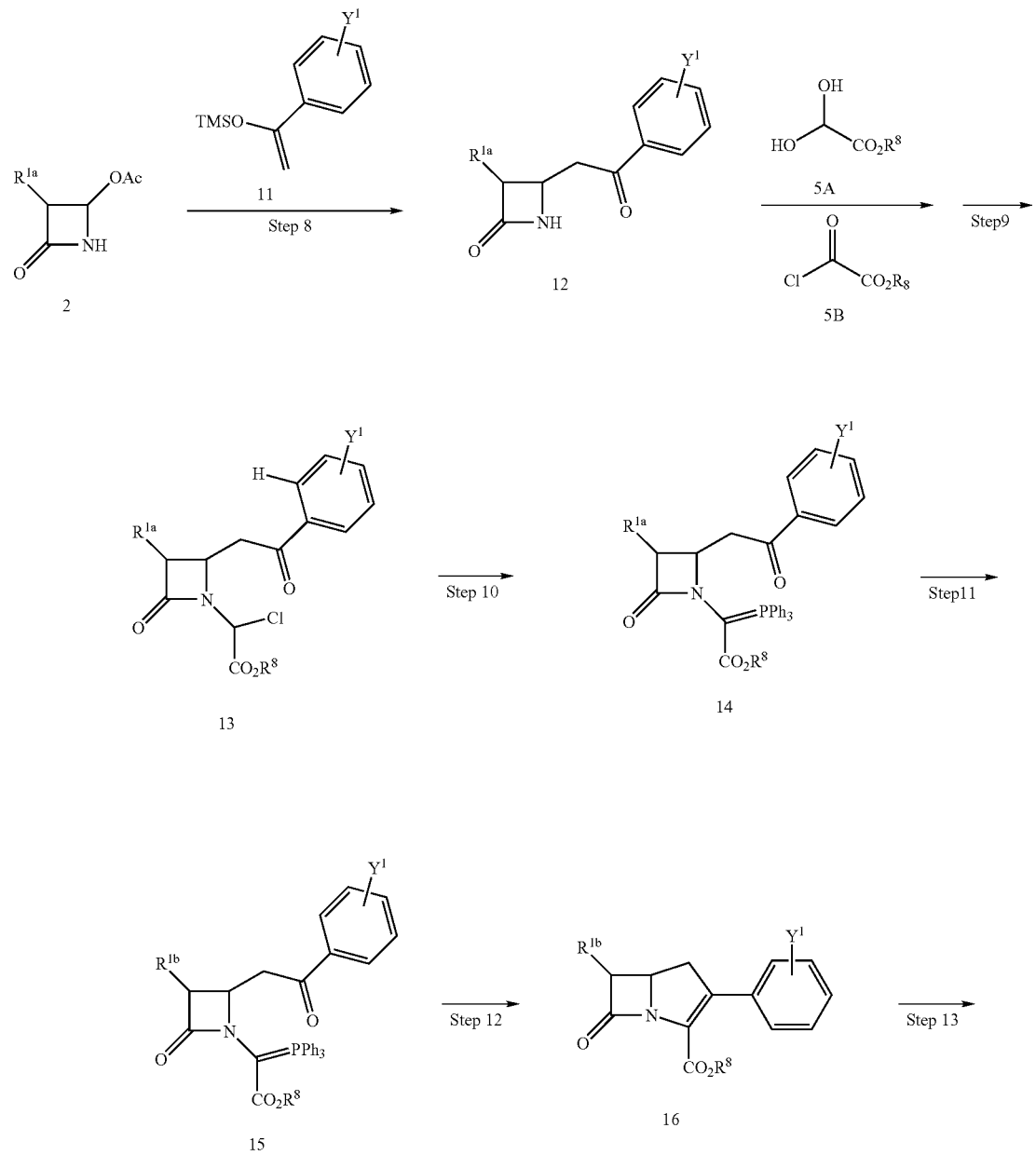

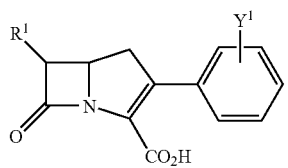

1-c (R = H)

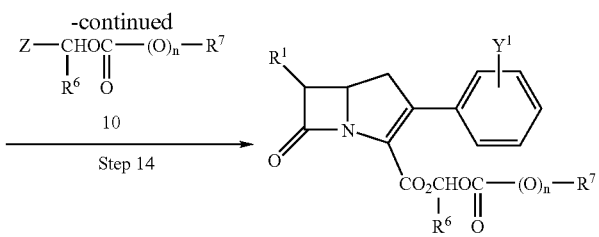

1-c (R is a group which reproduces carboxyl group by hydrolysis in vivo.)

In the above formulas, $R^1$, $R^{1a}$, $R^{1b}$, $R^6$, $R^7$, $R^8$, $Y^1$ and Z are the same as defined above.

Step 8: Process for Preparation of Compound 12

Compound 12 is prepared by reacting compound 2 and compound 11 in the presence of acid catalyst in an inert solvent. The acid catalyst includes zinc chloride, zinc bromide, zinc iodide, tin tetrachloride, trifluoromethanesulfonic acid trimethylsilyl ester or boron trifluoride-diethylether complex.

The inert solvent includes dichloromethane, 1,2-dichloroethane, acetonitrile, monochlorobenzene, dioxane, tetrahydrofuran, benzene or toluene.

The reaction is carried out at −78° C. to 60° C., preferably at −30° C. to 40° C. The starting compound 11 is also prepared by enol-etherification of various actetophenone derivatives prepared by known methods (e.g. Synthesis and reaction of organic compound [II] page 751-875 (1977), Sin Jikken Kagaku Kouza edited by The Chemical Society of Japan, Vol. 14 (Maruzen), or Organic Synthesis [III], Aldehyde Ketone Quinone, page 149-353 (1991), Sin Jikken Kagaku Kouza edited by The Chemical Society of Japan, 4th Edition (Maruzen)).

Step 9: Process for Preparation of Compound 13

Corresponding hemiacetal is prepared by heating compound 12 and compound 5A under dehydrating condition in an inert solvent. The inert solvent includes dichloromethane, 1,2-dichloroethane, monochlorobenzene, benzene, toluene or xylene. The reaction was carried out at 50° C. to 200° C., preferably at 80° C. to 150° C. In accordance of the known method (the method described in the Journal of Organic Chemistry, 61, 7889-7894 (1996)) the corresponding hemiacetal compound is also prepared by reacting compound 12 and compound 5B in the presence of a base in an inert solvent, followed by reduction to give an imido compound, The base includes triethylamine, diisopropylethylamine or N-methylmorpholine. The inert solvent for imidation includes dichloromethane, 1,2-dichloroethane or monochlorobenzene. The imidation was carried out at −50° C. to 50° C., preferably at −30° C. to 30° C. The reduction is carried out in preferably zinc, in a mixed solvent such as acetic acid and dichloromethane, acetic acid and 1,2-dichloroethane or acetic acid and monochlorobenzene at −50° C. to 50° C., preferably at −30° C. to 30° C.

Thus obtained hemiacetal compound is chlorinated using a chlorinating agent such as thionyl chloride, oxalyl chloride or phosphorous oxychloride. The chlorination is conducted in an inert solvent such as ether, tetrahydrofuran or dichloromethane, in the presence of a base such as lutidine, pyridine, quinoline, diisopropylethylamine or triethylamine at −78° C. to 60° C., preferably at −30° C. to 40° C.

Step 10: Process for Preparation of Compound 14

Compound 14 is prepared by reacting compound 13 with triphenylphosphine in an inert solvent such as tetrahydrofuran, dioxane or dimethoxyethane, in the presence of a base such as lutidine, pyridine, quinoline, diisopropylethylamine or triethylamine at 0° C. to 100° C., preferably at 10° C. to 70° C.

Step 11: Process for Preparation of Compound 15

If necessary, the protective group of hydroxy group in $R^{1a}$ is removed and followed by reprotection. The removal of the protective group or protecting is known (for example, T. W. Greene, P. G. M. Wuts: Protective Groups in Organic Synthesis; 3rd ed., Wiley, New York (1999), or P. Kocienski, Protecting Groups, Thieme, Stuttgart (1994)).

Step 12: Process for Preparation of Compound 16

Compound 16 is prepared by cyclizing compound 15 in an inert solvent such as benzene, toluene or xylene at 80° C. to 200° C.

Step 13: Process for Preparation of Compound [1-c] (R is Hydrogen Atom)

Carbapenem compound [1-c] (R is hydrogen atom) is prepared by removing a protective group of carboxyl group at $R^8$ of compound 16, or removing a protective group of hydroxy group when $R^{1b}$ is a protective group of hydroxy group. The removal of the protective group is carried out by known method such as treating with an acid, a base and a reduction agent (see T. W. Greene, P. G. M. Wuts: Protective Groups in Organic Synthesis; 3rd ed., Wiley, New York (1999), or P. Kocienski, Protecting Groups, Thieme, Stuttgart (1994)).

Step 14: Process for Preparation of Compound [1-c] (R is a Group Which reproduces carboxyl group by hydrolysis in vivo)

Compound [1-c] (R is a group which reproduces carboxyl group by hydrolysis in vivo) is prepared by introducing using a conventional method, a group which reproduces carboxyl group by hydrolysis in vivo into carbapenem compound [1-c] (R is hydrogen atom). For example, carbapenem compound [1-c] (R is hydrogen atom) or its carboxylic acid salt is reacted with various halides of the compound 10, if necessary, in the presence of a base such as diisopropylethylamine, triethylamine, 4-dimethylaminopyridine, potassium carbonate or sodium hydrogencarbonate, or phase transfer catalyst such as triethylbenzylammoniun chloride or tetrabutylammonium bromide. The reaction solvent is not limited as far as it is inert and preferably dimethylformamide, dimethyl sulfoxide, hexamethylphosphoramide, acetonitrile, dioxane, tetrahydrofuran or acetone. The carboxylic acid salt includes preferably its sodium or potassium salt. The reaction is carried out at −78° C. to 100° C., preferably −20° C. to 60° C. Furthermore, in step 9, using compound 5A or 5B having a group which reproduces carboxyl group by hydrolysis in vivo in $R^8$, and then, via each step, carbapenem compound [1-c] (R is a group which reproduces carboxyl group by hydrolysis in vivo) can be directly prepared.

In the above steps, after reaction the product is isolate by the method according to organic chemistry, and when the product is water soluble, the reaction mixture is adjusted to around neutralization and is subjected to column chromatography using absorption resin, etc. and the fractions containing the object compound are taken and lyophilized to the object compound.

The compound of the formula [1-d] is prepared for example, by proceed (3).

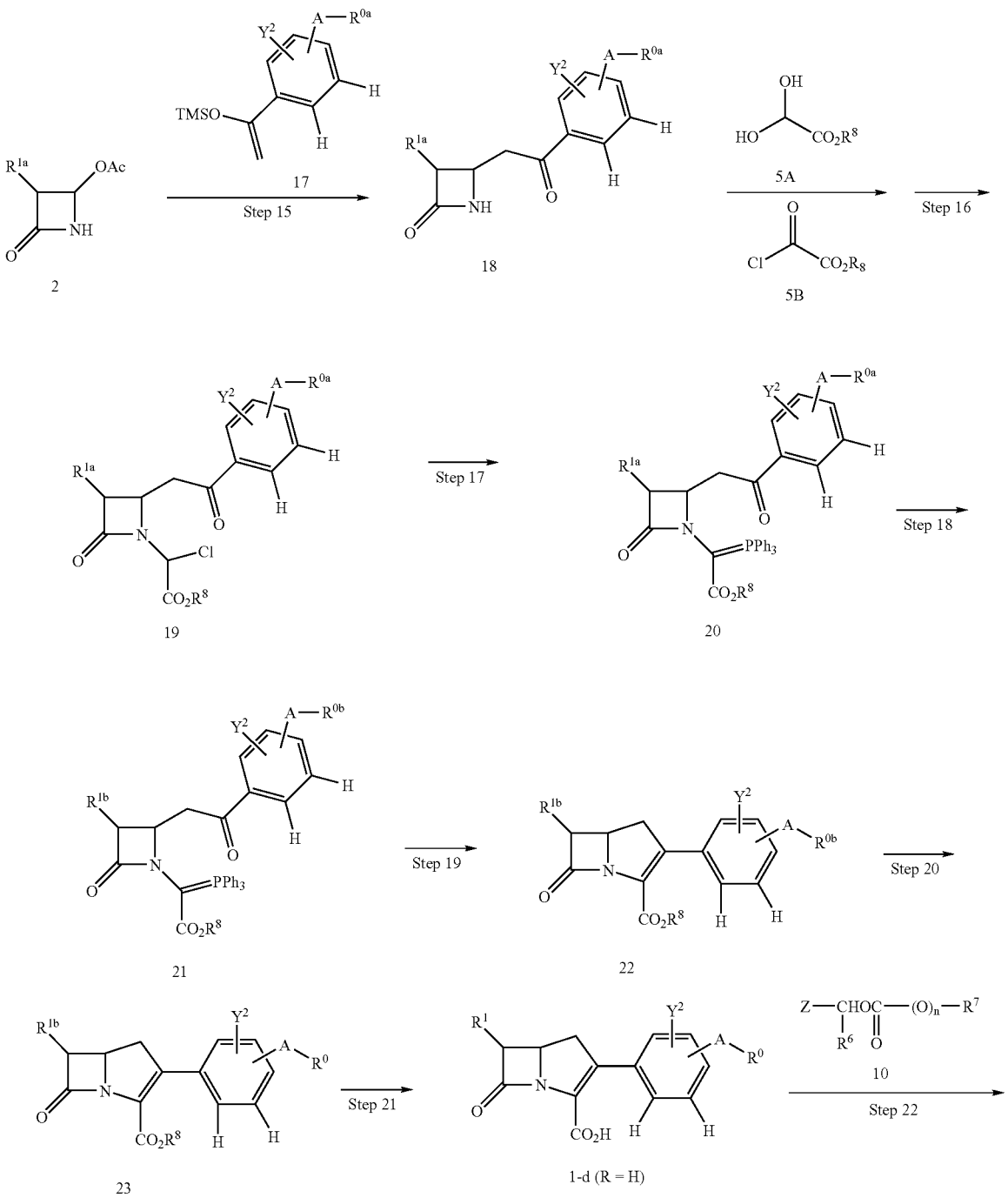

-continued

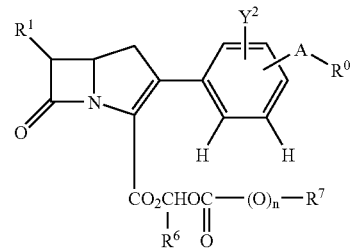

1-d (R is a group which reproduces carboxyl group by hydrolysis in vivo.)

In the above formulas $R^0$, $R^1$, $R^{1a}$, $R^{1b}$, $R^6$, $R^7$, $R^8$, A, $Y^2$ and Z are the same as defined above, $R^{0a}$ and $R^{0b}$ are hydroxy group, a protective group of amino group, the formula [2]:

wherein $R^{2a}$ and $R^{3a}$ are the same as defined above, or the formula [3]:

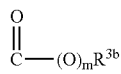

wherein m and $R^{3b}$ are the same as defined above.

Step 15: Process for Preparation of Compound 18

Compound 18 is prepared by reacting compound 2 and compound 17 in the presence of acid catalyst in an inert solvent. The acid catalyst includes zinc chloride, zinc bromide, zinc iodide, tin tetrachloride, trifluoromethanesulfonic acid trimethylsilyl ester or boron trifluoride-diethyl ether complex.

The inert solvent includes dichloromethane, 1,2-dichloroethane, acetonitrile, monochlorobenzene, dioxane, tetrahydrofuran, benzene or toluene.

The reaction is carried out at −78° C. to 60° C., preferably at −30° C. to 40° C. The starting compound 17 is prepared by enol-etherification of various acetophenone derivatives prepared by known methods (e.g. Synthesis and reaction of organic compound [II] page 751-875 (1977), Sin Jikken Kagaku Kouza edited by The Chemical Society of Japan, Vol. 14 (Maruzen), or Organic Synthesis [III], Aldehyde-Ketone-Quinone, page 149-353 (1991), Sin Jikken Kagaku Kouza edited by The Chemical Society of Japan, 4th Edition (Maruzen)).

Step 16: Process for Preparation of Compound 19

Corresponding hemiacetal is prepared by heating compound 18 and compound 5A under dehydrating condition in an inert solvent. The inert solvent includes dichloromethane, 1,2-dichloroethane, monochlorobenzene, benzene, toluene or xylene. The reaction was carried out at 50° C. to 200° C., preferably at 80° C. to 150° C. In accordance with the known method (the method described in the Journal of Organic Chemistry, 61, 7889-7894 (1996)) the corresponding hemiacetal compound is also prepared by reacting compound 18 and compound 5B in the presence of a base in an inert solvent, followed by reduction to give an imido compound. The base includes triethylamine, diisopropylethylamine or N-methylmorpholine. The inert solvent for imidation includes dichloromethane, 1,2-dichloroethane or monochlorobenzene. The imidation was carried out at −50° C. to 50° C., preferably at −30° C. to 30° C. The reduction is carried out in preferably zinc, in a mixed solvent such as a mixture of acetic acid and dichloromethane, a mixture of acetic acid and 1,2-dichloroethane or a mixture of acetic acid and monochlorobenzene at −50° C. to 50° C., preferably at −30° C. to 30° C.

Thus obtained hemiacetal compound is chlorinated using a chlorinating agent such as thionyl chloride, oxalyl chloride or phosphorous oxychloride. The chlorination is conducted in an inert solvent such as ether, tetrahydrofuran or dichloromethane, in the presence of a base such as lutidine, pyridine, quinoline, diisopropylethylamine or triethylamine at −78° C. to 60° C., preferably at −30° C. to 40° C.

Step 17: Process for Preparation of Compound 20

Compound 20 is prepared by reacting compound 19 with triphenylphosphine in an inert solvent such as tetrahydrofuran, dioxane or dimethoxyethane, in the presence of a base such as lutidine, pyridine, quinoline, diisopropylethylamine or triethylamine at 0° C. to 100° C., preferably at 10° C. to 70° C.

Step 18: Process for Preparation of Compound 21

If necessary, the protective group of hydroxy group in $R^{1a}$ and a protective group in $R^{0a}$ are removed and followed by reprotecting. The removal of the protective group or protecting is known (for example see T. W. Greene, P. G. M. Wuts: Protective Groups in Organic Synthesis; 3rd ed., Wiley, New York (1999), or P. Kocienski, Protecting Groups, Thieme, Stuttgart (1994).

Step 19: Process for Preparation of Compound 22

Compound 22 is prepared by cyclizing compound 21 in an inert solvent such as benzene, toluene or xylene at 80° C. to 200° C.

Step 20: Process for Preparation of Compound 23

Compound 23 is prepared by removing a protective group in $R^{0b}$ of compound 22, if necessary, followed by known chemical reaction (acylation, carbamate-formation, urea-formation). The removal of the protective group is carried our by known method (for example, see T. W. Greene, P. G. M. Wuts: Protective Groups in Organic Synthesis; 3rd ed., Wiley, New York (1999), or P. Kocienski, Protecting Groups, Thieme, Stuttgart (1994)).

Step 21: Process for preparation of compound [1-d] (R is Hydrogen Atom)

Carbapenem compound [1-d] (R is hydrogen atom) is prepared by removing a protective group of carboxyl group in $R^8$ of compound 23, or removing a protective group of hydroxy group when $R^{1b}$ is a protective group of hydroxy group. The removal of the protective group is carried out by known method such as treating with acid base, reduction agent (see such as T. W. Greene, P. G. M. Wuts: Protective Groups in Organic Synthesis; 3rd ed., Wiley, New York (1999), or P. Kocienski, Protecting Groups, Thieme, Stuttgart (1994)).

Step 22: Process for Preparation of Compound [1-d] (R is a Group which Reproduces carboxyl Group by hydrolysis in Vivo)

Compound [1-d] (R is a group which reproduces carboxyl group by hydrolysis in vivo) is prepared by introducing using a conventional method, a group which reproduces carboxyl group by hydrolysis in vivo into carbapenem compound [1-d] (R is hydrogen atom). For example, carbapenem compound [1-d] (R is hydrogen atom) or its carboxylic acid salt is reacted with various halides of the compound 10, if necessary, in the presence of a base such as diisopropylethylamine, triethylamine, 4-dimethylaminopyridine, potassium carbonate or sodium hydrogencarbonate, or phase transfer catalyst such as triethylbenzylammoniun chloride or tetrabutylammonium bromide. The reaction solvent is not limited as far as it is inert and it includes preferably dimethylformamide, dimethyl sulfoxide, hexamethylphosphoramide, acetonitrile, dioxane or tetrahydrofuranor acetone. The carboxylic acid salt includes preferably its sodium or potassium salt. The reaction is carried out at −78° C. to 100° C., preferably −20° C. to 60° C. Furthermore, in step 16, using compound 5A or 5B having a group which reproduces carboxyl group by hydrolysis in vivo in $R^8$, and then, via each step, carbapenem compound [1-d] (R is a group which reproduces carboxyl group by hydrolysis in vivo) can be directly prepared.

In the above steps, after reaction the product is isolated by the method according to organic chemistry, and when the product is water soluble, the reaction mixture is adjusted to around neutralization and is subjected to column chromatography using absorption resin, etc. The fractions containing the object compound are taken and lyophilized to give the object compound.

The optical isomers based on asymmetric carbon atoms on the present carbapenem compound at 5- and 6-positions of 7-oxo-1-azabicyclo[3.2.0]hept-2-ene, a core structure, exist as shown in a following formula [5],

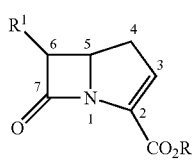

[5]

These isomers are all conveniently expressed by only one formula, but the scope of the present invention should not be construed to be limited thereto, and includes all isomers and a mixture of isomers based on each asymmetric carbon atom. The preferable isomers are ones wherein the 5-carbon atom has an R-configuration such as (5R, 6R)-compounds or (5R, 6S)-compounds. More preferable compounds are one represented by a following formula [5a],

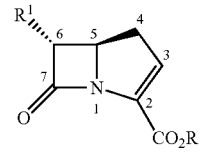

[5-a]

Furthermore, when $R^1$ is 1-hydroxyethyl group, there are isomers having an R-configuration and an S-configuration at position 8 as shown in a following formula [5b], and an isomer having the R-configuration is preferable.

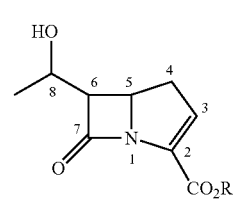

[5b]

The isomers having (5R,6S,8R)-configuration of the following formula [5C]:

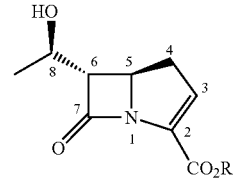

[5c]

are most preferable.

In regard to the substitution position on benzene ring which is, a side chain at position 3, said substitution position is not limited, and meta or para position is preferable.

Examples of carbapenem compound of the present invention are illustrated as compounds 1 to 176 in Tables 1 to 20.

TABLE 1

| Compound number | R |
|---|---|
| 1 | —CHOC(=O)C₆H₁₁ with Me (—CH(Me)OC(=O)-cyclohexyl) |
| 2 | —CH₂OC(=O)CHMe₂ |

TABLE 1-continued

[Structure: carbapenem with HO-CH(CH3)- group, 4-methoxyphenyl substituent, CO2R]

| Compound number | R |
|---|---|
| 3 | —CH(Me)OC(O)CH(Me)2 |
| 4 | —CH2OC(O)C(Me)(cyclohexyl) |
| 5 | —CH(Me)OC(O)OEt |
| 6 | —CH(Me)OC(O)OCH(Me)2 |
| 7 | —CH(Me)OC(O)cyclohexyl |
| 8 | —CH2OC(O)cyclohexyl |
| 9 | —CH(Me)OC(O)OCH2CH2Me |
| 10 | —CH2OC(O)C(Me)3 |
| 11 | —CH(Me)OC(O)OC(Me)3 |
| 12 | —CH(Me)OC(O)Ocyclopentyl |
| 13 | —CH(Me)OC(O)C(Me)3 |

TABLE 1-continued

[Structure: carbapenem with HO-CH(CH3)- group, 4-methoxyphenyl substituent, CO2R]

| Compound number | R |
|---|---|
| 14 | 3-methylphthalide-yl |
| 15 | (5-methyl-2-oxo-1,3-dioxol-4-yl)methyl (with Et) |
| 16 | (5-phenyl-2-oxo-1,3-dioxol-4-yl)methyl (with Et) |

TABLE 2

[Structure: carbapenem with HO-CH(CH3)- group, 3-methoxyphenyl substituent, CO2R]

| Compound number | R |
|---|---|
| 17 | —CH(Me)OC(O)Ocyclohexyl |
| 18 | —CH2OAc |
| 19 | —CH(Me)OAc |
| 20 | —CH2OC(O)CH(Me)2 |
| 21 | —CH(Me)OC(O)CH(Me)2 |

TABLE 2-continued
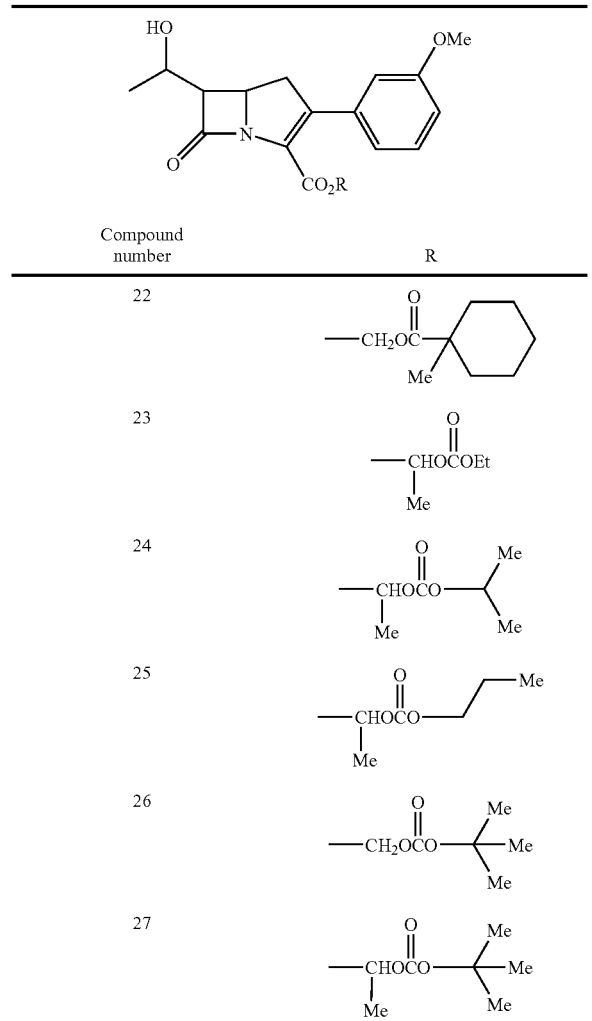
| Compound number | R |
|---|---|
| 22 | —CH₂OC(O)-1-methylcyclohexyl |
| 23 | —CH(Me)OC(O)OEt |
| 24 | —CH(Me)OC(O)CH(Me)₂ |
| 25 | —CH(Me)OC(O)OCH₂CH₂Me |
| 26 | —CH₂OC(O)C(Me)₃ |
| 27 | —CH(Me)OC(O)C(Me)₃ |
TABLE 2-continued
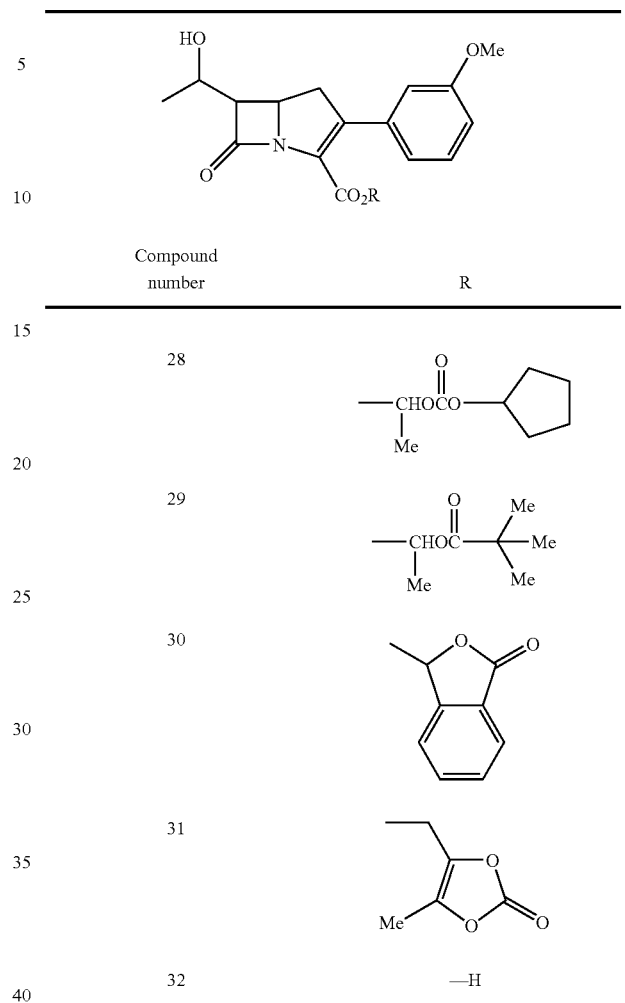
| Compound number | R |
|---|---|
| 28 | —CH(Me)OC(O)cyclopentyl |
| 29 | —CH(Me)OC(O)C(Me)₃ |
| 30 | 3-methylphthalidyl |
| 31 | (5-methyl-2-oxo-1,3-dioxol-4-yl)ethyl |
| 32 | —H |
TABLE 3
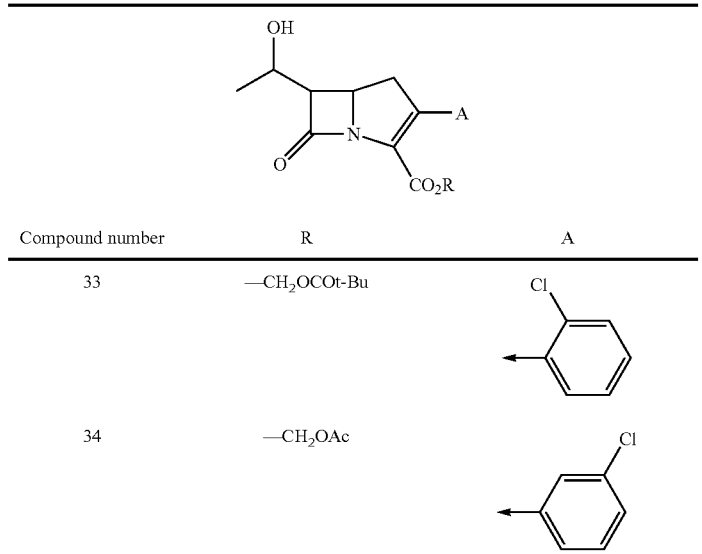
| Compound number | R | A |
|---|---|---|
| 33 | —CH₂OCOt-Bu | 2-chlorophenyl |
| 34 | —CH₂OAc | 3-chlorophenyl |

TABLE 3-continued
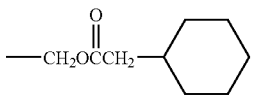
| Compound number | R | A |
|---|---|---|
| 35 | —CH₂OC(O)CH₂-cyclohexyl | 4-Cl-phenyl |
| 36 | —CH₂OC(O)C(Me)(cyclohexyl) | 4-OPr-phenyl |
| 37 | —CH(Me)OC(O)OEt | 4-O-n-Bu-phenyl |
| 38 | —CH(Me)OC(O)O-cyclohexyl | 4-Br-phenyl |
| 39 | —CH(Me)OAc | 3-O-n-Bu-phenyl |
| 40 | —CH₂OCOt-Bu | 3-O-iPr-phenyl |
TABLE 4
| Compound number | R | A |
|---|---|---|
| 41 | —CH₂OCOt-Bu | 4-OCH₂CH₂OEt-phenyl |
| 42 | —CH₂OAc | 4-CH₂OEt-phenyl |

TABLE 4-continued
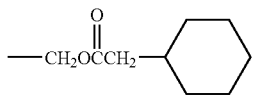
| Compound number | R | A |
|---|---|---|
| 43 | 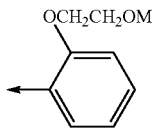 | 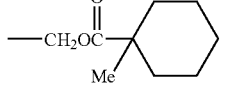 |
| 44 | 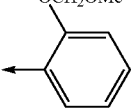 | 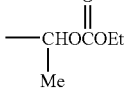 |
| 45 | 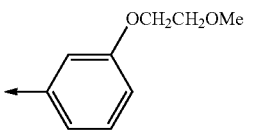 | 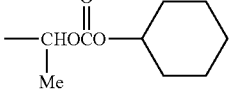 |
| 46 | 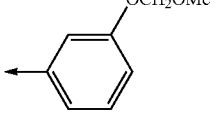 | 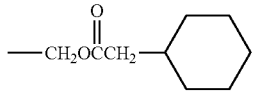 |
| 47 | 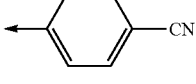 |  |
| 48 | —CH$_2$OCOt-Bu | 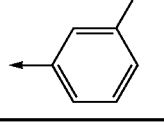 |
TABLE 5
| Compound number | R | A |
|---|---|---|
| 49 | —CH$_2$OCOt-Bu | 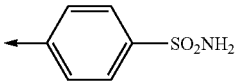 |
| 50 | —CH$_2$OAc |  |

TABLE 5-continued
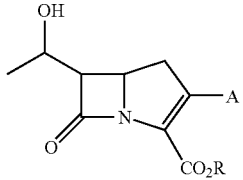
| Compound number | R | A |
|---|---|---|
| 51 | 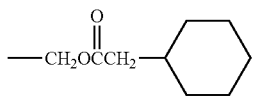 | 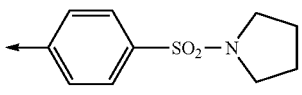 |
| 52 | 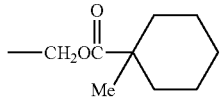 | 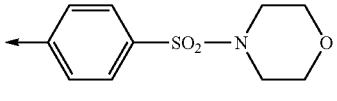 |
| 53 | 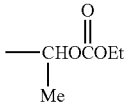 | 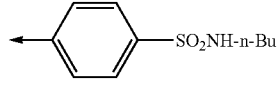 |
| 54 | —CH₂OCOt-Bu | 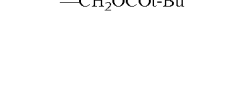 |
| 55 | 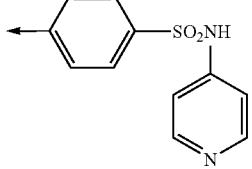 | 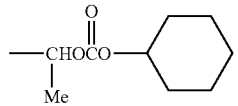 |
| 56 | 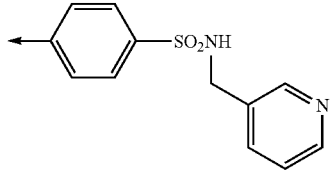 | 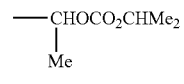 |

TABLE 6
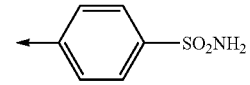
| Compound number | R | A |
|---|---|---|
| 57 | —H | 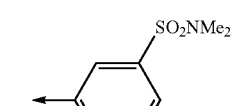 |
| 58 | —H | 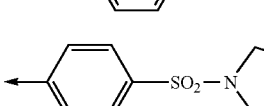 |
| 59 | —H | 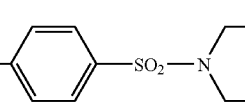 |
| 60 | —H | 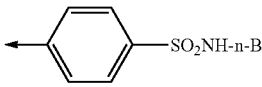 |
| 61 | —H | 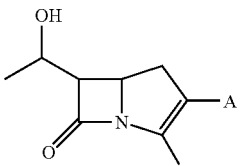 |
TABLE 6-continued
| Compound number | R | A |
|---|---|---|
| 62 | —H | 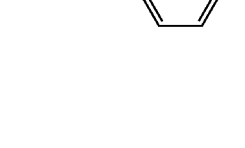 |
| 63 | —H | 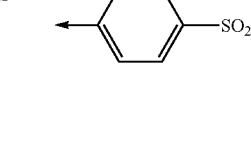 |
| 64 | —H | 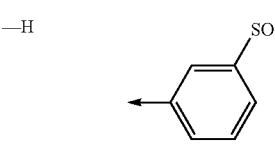 |
TABLE 7
| Compound number | R | A |
|---|---|---|
| 65 | —CH₂OCOt-Bu | 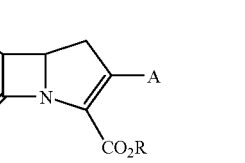 |
| 66 | —CH₂OAc | 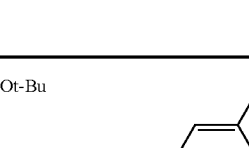 |

TABLE 7-continued
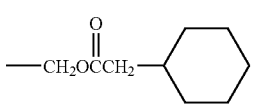
| Compound number | R | A |
|---|---|---|
| 67 | 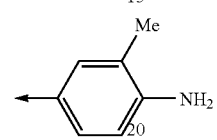 | 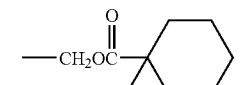 |
| 68 | 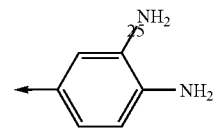 | 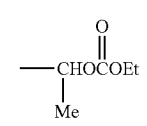 |
| 69 | 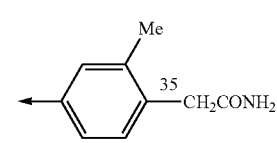 |  |
| 70 | —CH$_2$OCOt-Bu | 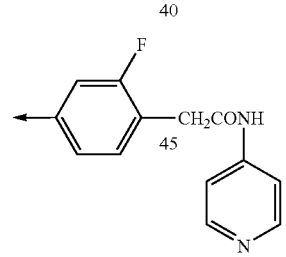 |
| 71 | 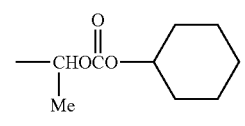 | 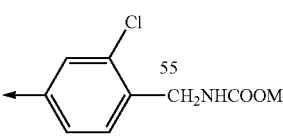 |
| 72 | —CH$_2$OCOt-Bu |  |

TABLE 8
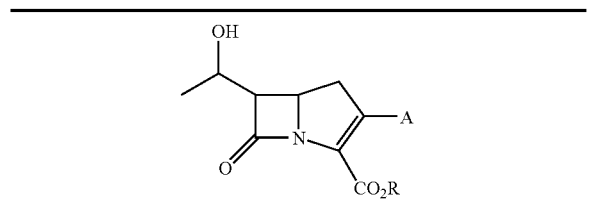
| Compound number | R | A |
|---|---|---|
| 73 | —H | 2-F, 4-(NHCO-4-pyridyl)phenyl |
| 74 | —H | 3-OMe, 4-NH₂ phenyl |
| 75 | —H | 3-Me, 4-NH₂ phenyl |
| 76 | —H | 3-NH₂, 4-NH₂ phenyl |
TABLE 8-continued
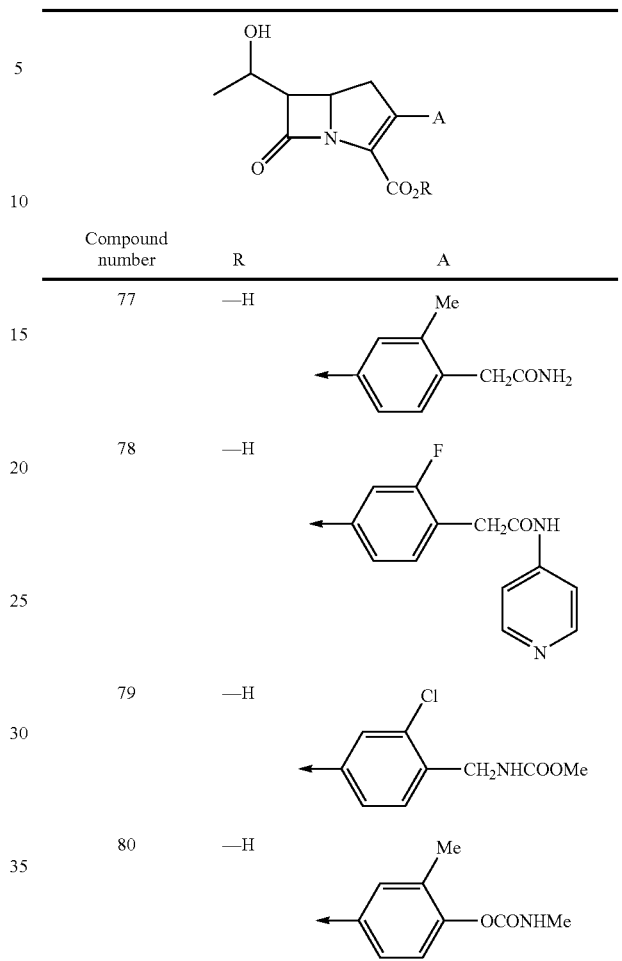
| Compound number | R | A |
|---|---|---|
| 77 | —H | 2-Me, 4-CH₂CONH₂ phenyl |
| 78 | —H | 2-F, 4-CH₂CONH-(4-pyridyl) phenyl |
| 79 | —H | 2-Cl, 4-CH₂NHCOOMe phenyl |
| 80 | —H | 2-Me, 4-OCONHMe phenyl |
TABLE 9
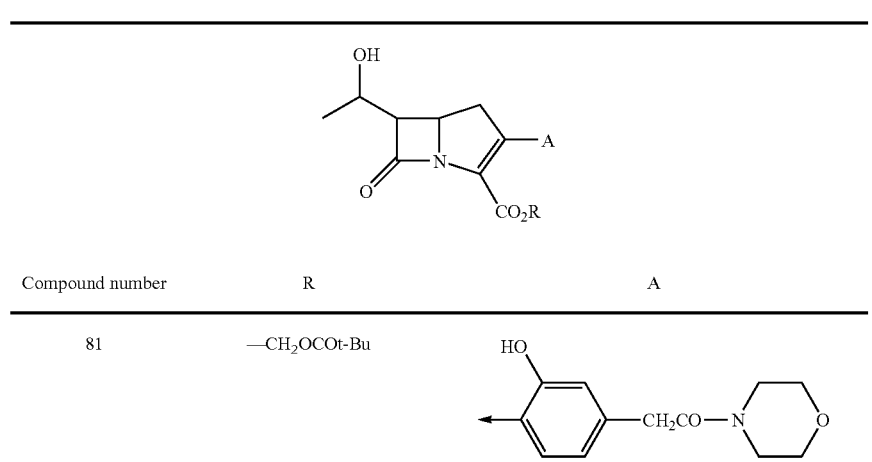
| Compound number | R | A |
|---|---|---|
| 81 | —CH₂OCOt-Bu | 3-OH, 4-CH₂CO-morpholino phenyl |

TABLE 9-continued
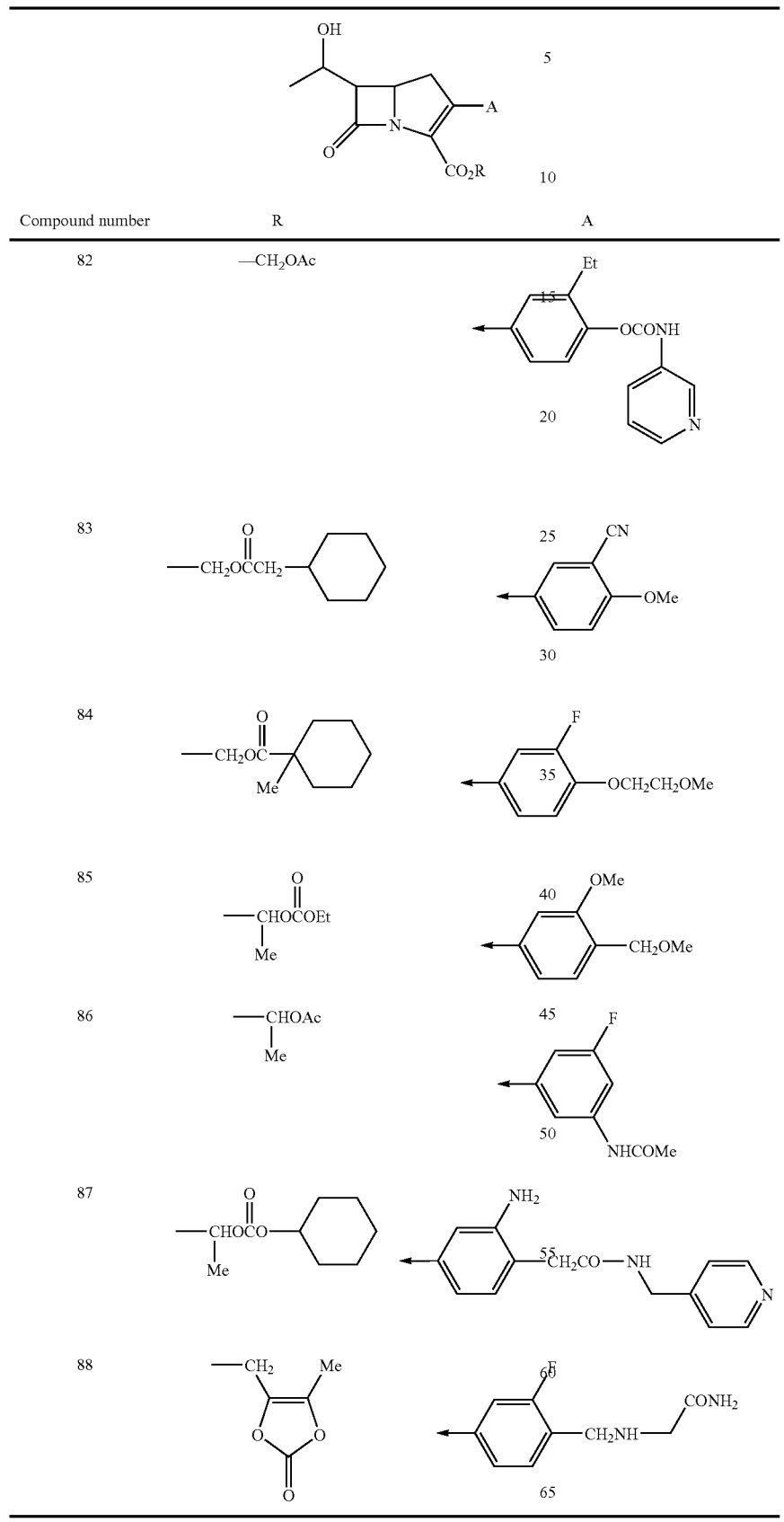
| Compound number | R | A |
|---|---|---|
| 82 | —CH$_2$OAc | 2-Et, 4-(—OCONH-(pyridin-3-yl))phenyl |
| 83 | —CH$_2$OC(O)CH$_2$-cyclohexyl | 2-CN, 4-OMe phenyl (attached at 5) |
| 84 | —CH$_2$OC(O)-C(Me)(cyclohexyl) | 2-F, 4-OCH$_2$CH$_2$OMe phenyl |
| 85 | —CH(Me)OC(O)OEt | 2-OMe, 4-CH$_2$OMe phenyl |
| 86 | —CH(Me)OAc | 3-F, 5-NHCOMe phenyl |
| 87 | —CH(Me)OC(O)O-cyclohexyl | 2-NH$_2$, 4-(CH$_2$CO—NH—CH$_2$-(pyridin-4-yl))phenyl |
| 88 | —CH$_2$-(4-Me-5-H-1,3-dioxol-2-on-4-yl) | 2-F, 4-(CH$_2$NH—CH$_2$CONH$_2$)phenyl |

TABLE 10

[Core structure: carbapenem with OH-CH(CH3)- substituent, CO2R, and A group]

| Compound number | R | A |
|---|---|---|
| 89 | —H | 3-hydroxy-4-(CH2CO-morpholino)phenyl |
| 90 | —H | 2-ethyl-4-(OCONH-(pyridin-3-yl))phenyl |
| 91 | —H | 3-cyano-4-methoxyphenyl |
| 92 | —H | 2-fluoro-4-(OCH2CH2OMe)phenyl |

TABLE 10-continued

| Compound number | R | A |
|---|---|---|
| 93 | —H | 2-methoxy-4-(CH2OMe)phenyl |
| 94 | —H | 3-fluoro-5-(NHCOMe)phenyl |
| 95 | —H | 2-amino-4-(CH2CO—NH—CH2-(pyridin-4-yl))phenyl |
| 96 | —H | 2-fluoro-4-(CH2NH-CH2CONH2)phenyl |

TABLE 11

| Compound number | R | A |
|---|---|---|
| 97 | —CH2OCOt-Bu | 2-amino-4-(OCH2CONHMe)phenyl |
| 98 | —CH2OCOCHMe2 | 2-fluoro-4-(CH2NHCONHMe)phenyl |

TABLE 11-continued
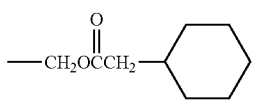
| Compound number | R | A |
|---|---|---|
| 99 | 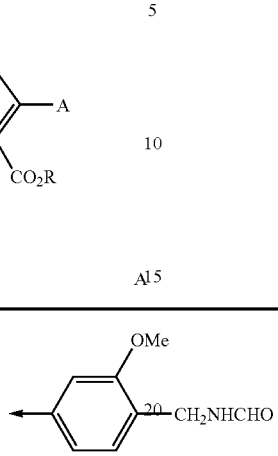 | 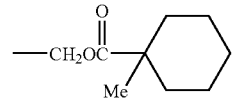 |
| 100 | 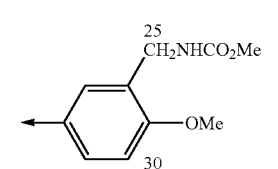 | 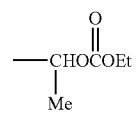 |
| 101 | 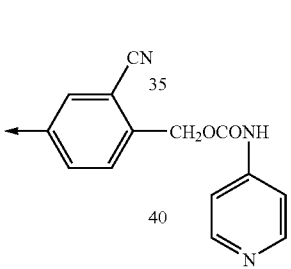 | 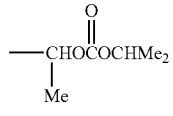 |
| 102 | 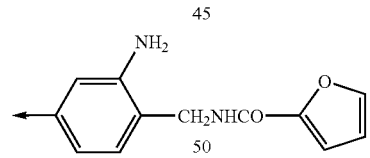 | 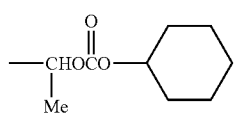 |
| 103 | 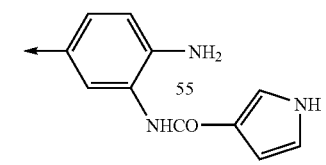 | 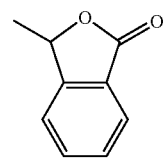 |
| 104 | 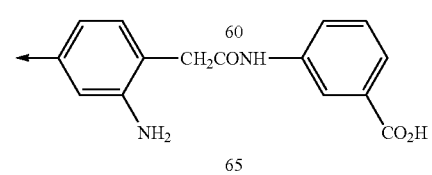 |  |

TABLE 12

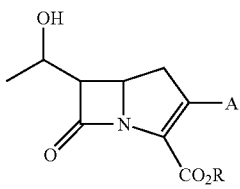

| Compound number | R | A |
|---|---|---|
| 105 | —H | 2-NH₂, 1-OCH₂CONHMe phenyl |
| 106 | —H | 2-F, 1-CH₂NHCONHMe phenyl |
| 107 | —H | 2-OMe, 1-CH₂NHCHO phenyl |
| 108 | —H | 2-OMe, 1-CH₂NHCO₂Me phenyl |

TABLE 12-continued

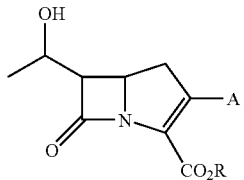

| Compound number | R | A |
|---|---|---|
| 109 | —H | 2-CN, 1-CH₂OCONH-(pyridin-4-yl) phenyl |
| 110 | —H | 2-NH₂, 1-CH₂NHCO-(furan-2-yl) phenyl |
| 111 | —H | 2-NH₂, 1-NHCO-(1H-pyrrol-3-yl) phenyl |
| 112 | —H | 2-NH₂, 1-CH₂CONH-(3-CO₂H-phenyl) phenyl |

TABLE 13

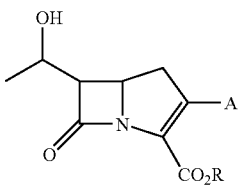

| Compound number | R | A |
|---|---|---|
| 113 | —CH₂OCOt-Bu | 2-NH₂, 1-CH₂OH phenyl |
| 114 | —CH₂OCOCHMe₂ | 2-F, 1-NHCH₂CH₂OH phenyl |

TABLE 13-continued

[Structure: carbapenem core with 1-hydroxyethyl substituent, CO₂R group, and substituent A]

| Compound number | R | A |
|---|---|---|
| 115 | —CH₂OC(O)CH₂-cyclohexyl | 4-(2-hydroxy-1-amino)phenyl (OH, NH₂) |
| 116 | —CH₂OC(O)-C(Me)(cyclohexyl) | 4-(2-hydroxy-1-NHCOMe)phenyl |
| 117 | —CH(Me)OC(O)OEt | 3-NHCHO, 4-CH₂CH₂OH phenyl |
| 118 | —CH(Me)OC(O)CHMe₂ | 3-NHCOMe, 4-NHCOMe phenyl |
| 119 | —CH(Me)OC(O)O-cyclohexyl | 4-OCH₂CH₂OH, 3-NH₂ phenyl |
| 120 | 3-methylphthalidyl | 4-(NHCONH-pyridin-3-yl), 2-F phenyl |

TABLE 14

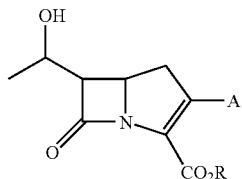

| Compound number | R | A |
|---|---|---|
| 121 | —H | 4-position on benzene with 2-NH₂, 3-CH₂OH substituents |
| 122 | —H | benzene with 2-NHCH₂CH₂OH, 3-F |
| 123 | —H | benzene with 2-NH₂, 3-OH |
| 124 | —H | benzene with 2-NHCOMe, 3-OH |

TABLE 14-continued

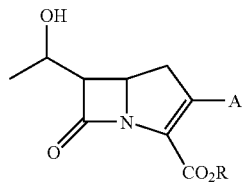

| Compound number | R | A |
|---|---|---|
| 125 | —H | benzene with 2-CH₂OH, 3-NHCHO |
| 126 | —H | benzene with 2-NHCOMe, 3-NHCOMe |
| 127 | —H | benzene with 2-OCH₂CH₂OH, 3-NH₂ |
| 128 | —H | benzene with 2-NHCONH(3-pyridyl), 3-F |

TABLE 15

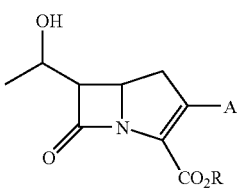

| Compound number | R | A |
|---|---|---|
| 129 | —CH₂OCOt-Bu | benzene with 2-CH₂CONH(4-pyridyl), 3-NH₂ |
| 130 | —CH₂OAc | benzene with 2-CH₂CONHCH₂(3-pyridyl), 3-NH₂ |

TABLE 15-continued
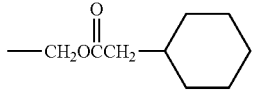
| Compound number | R | A |
|---|---|---|
| 131 | 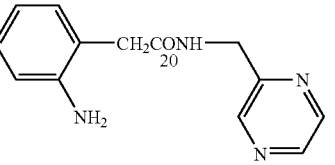 | 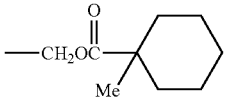 |
| 132 | 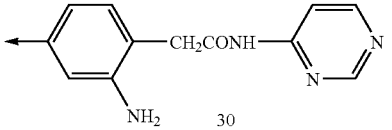 | 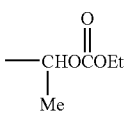 |
| 133 | 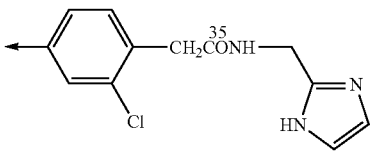 |  |
| 134 | —CH₂OCOt-Bu | 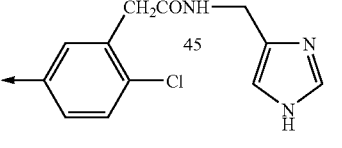 |
| 135 | 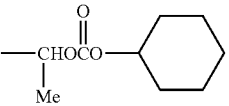 | 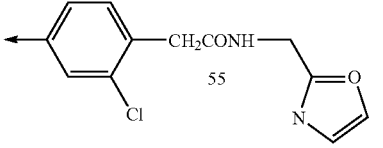 |
| 136 | —CH₂OCOt-Bu | 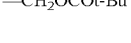 |

TABLE 16

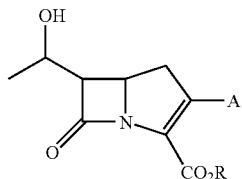

| Compound number | R | A |
|---|---|---|
| 137 | —H | 4-aminobenzyl-CH₂CONH-(4-pyridyl) |
| 138 | —H | 4-aminobenzyl-CH₂CONH-CH₂-(3-pyridyl) |
| 139 | —H | 4-aminobenzyl-CH₂CONH-CH₂-(pyrazinyl) |
| 140 | —H | 4-aminobenzyl-CH₂CONH-(4-pyrimidinyl) |

TABLE 16-continued

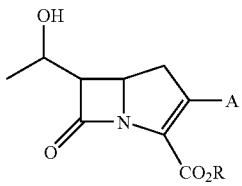

| Compound number | R | A |
|---|---|---|
| 141 | —H | 2-chlorobenzyl-CH₂CONH-CH₂-(2-imidazolyl) |
| 142 | —H | 2-chlorobenzyl-CH₂CONH-CH₂-(4-imidazolyl) |
| 143 | —H | 2-chlorobenzyl-CH₂CONH-CH₂-(2-oxazolyl) |
| 144 | —H | 2-chlorobenzyl-CH₂NHCO-CH₂-(4-imidazolyl) |

TABLE 17

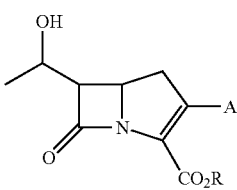

| Compound number | R | A |
|---|---|---|
| 145 | —CH₂OCOt-Bu | 4-amino-2-benzyl-CH₂CONH-(2-oxazolyl) |
| 146 | —CH₂OAc | 3-amino-4-benzyl-OCH₂CONH-CH₂-(4-pyridyl) |

TABLE 17-continued
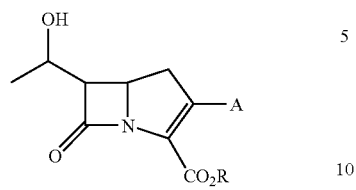
| Compound number | R | A |
|---|---|---|
| 147 | | |
| 148 | | |
| 149 | | |
| 150 | | |
| 151 | | |
| 152 | | |

TABLE 18
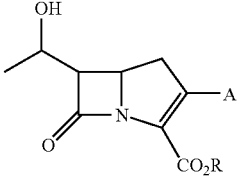
| Compound number | R | A |
|---|---|---|
| 153 | —H | 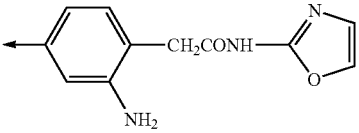 |
| 154 | —H | 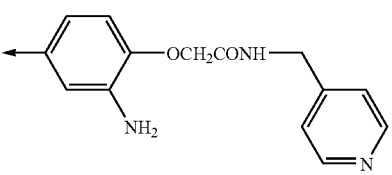 |
| 155 | —H | 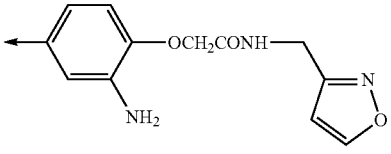 |
| 156 | —H | 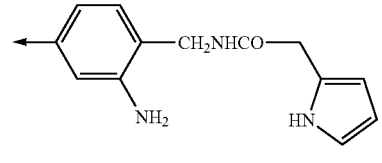 |
TABLE 18-continued
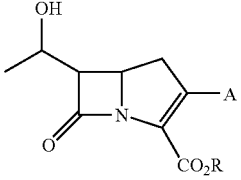
| Compound number | R | A |
|---|---|---|
| 157 | —H | 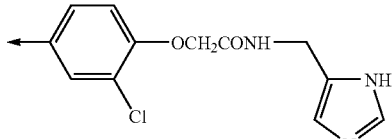 |
| 158 | —H | 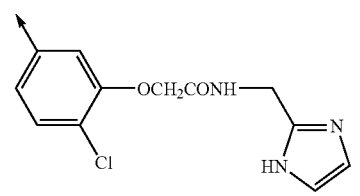 |
| 159 | —H | 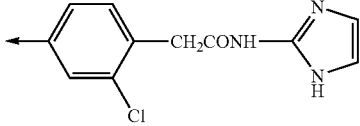 |
| 160 | —H | 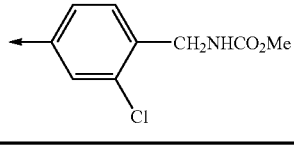 |
TABLE 19
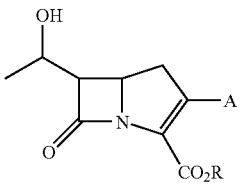
| Compound number | R | A |
|---|---|---|
| 161 | —CH$_2$OCOt-Bu | 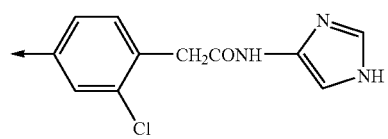 |

TABLE 19-continued
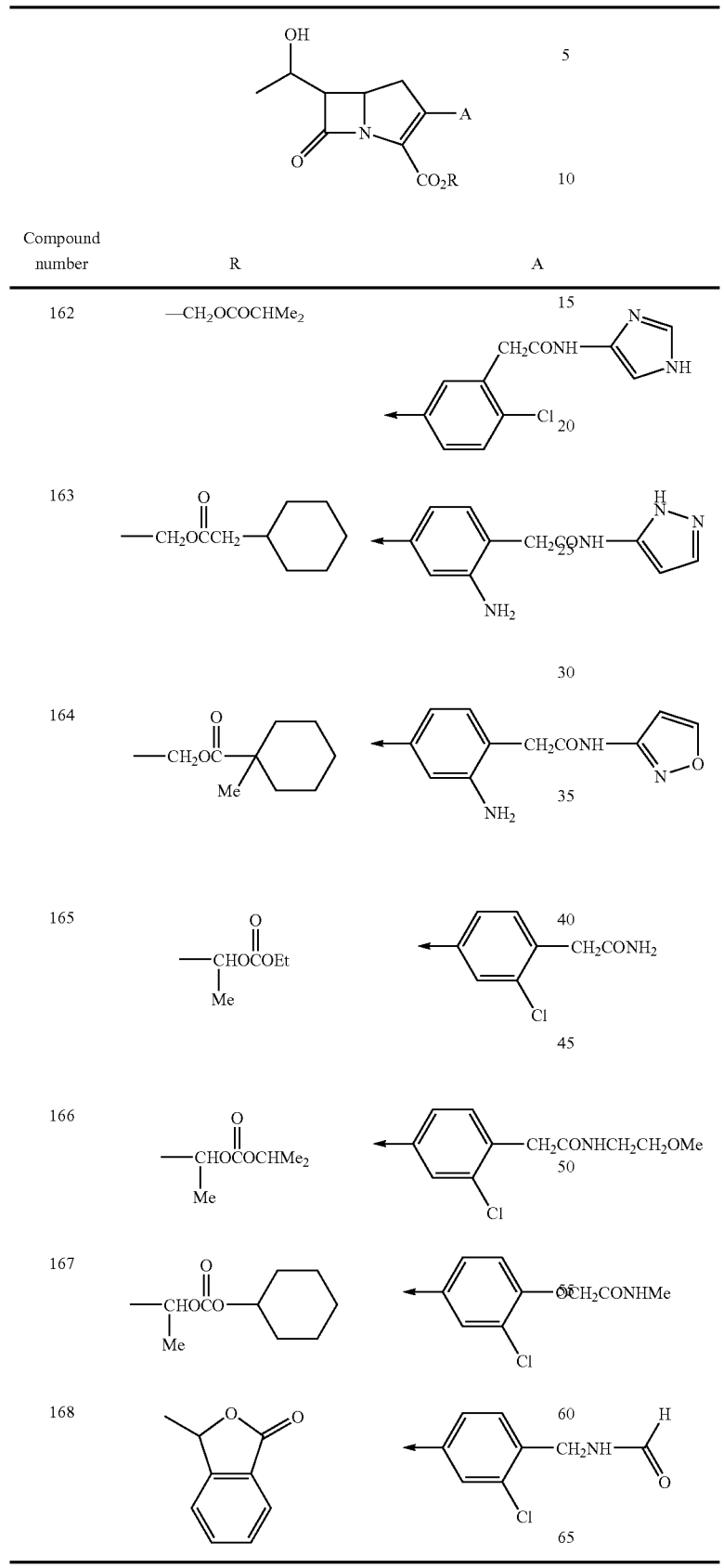
| Compound number | R | A |
|---|---|---|
| 162 | —CH₂OCOCHMe₂ | 2-Cl-5-(CH₂CONH-imidazol-4-yl)phenyl |
| 163 | —CH₂OC(O)CH₂-cyclohexyl | 2-NH₂-4-(CH₂CONH-pyrazol-5-yl)phenyl |
| 164 | —CH₂OC(O)-(1-Me-cyclohexyl) | 2-NH₂-4-(CH₂CONH-isoxazol-3-yl)phenyl |
| 165 | —CH(Me)OCOEt | 2-Cl-4-CH₂CONH₂-phenyl |
| 166 | —CH(Me)OCOCHMe₂ | 2-Cl-4-(CH₂CONHCH₂CH₂OMe)phenyl |
| 167 | —CH(Me)OCO-cyclohexyl | 2-Cl-5-(OCH₂CONHMe)phenyl |
| 168 | 3-methylphthalid-3-yl | 2-Cl-4-(CH₂NHCHO)phenyl |

TABLE 20

![Core structure with OH-CH(CH3)- on β-lactam fused to pyrroline with CO2R and substituent A]

| Compound number | R | A |
|---|---|---|
| 169 | —H | ←⟨phenyl, 2-Cl⟩—CH$_2$CONH—(imidazol-4-yl) |
| 170 | —H | ←⟨phenyl, 2-Cl (para to arrow)⟩—CH$_2$CONH—(imidazol-4-yl) |
| 171 | —H | ←⟨phenyl, 2-NH$_2$⟩—CH$_2$CONH—(pyrazol-3-yl) |
| 172 | —H | ←⟨phenyl, 2-NH$_2$⟩—CH$_2$CONH—(isoxazol-3-yl) |
| 173 | —H | ←⟨phenyl, 2-Cl⟩—CH$_2$CONH$_2$ |
| 174 | —H | ←⟨phenyl, 2-Cl⟩—CH$_2$CONHCH$_2$CH$_2$OMe |
| 175 | —H | ←⟨phenyl, 2-Cl⟩—OCH$_2$CONHMe |
| 176 | —H | ←⟨phenyl, 2-Cl⟩—CH$_2$NH—CHO |

The compounds illustrated above have stereoisomers as described above or else stereoisomers based on asymmetric carbon atoms, and the compounds include all these isomers.

EXAMPLE

The present invention is explained by the following examples, but the present invention is not limited to these examples Abbreviations Used in the Following Examples Means Below.
Ac: acetyl group
AOC: allyloxycarbonyl group
t-Bu: tert-butyl group
DMF: N,N-dimethylformamide
DMSO: dimethy sulfoxide
Et: ethyl group
Me: methyl group
MOPS: 4-morpholine propanesulfinic acid
Ph: phenyl group
PNB: p-nitrobenzyl group
TBDMS: tert-butyl(dimethyl) silyl group
THF: tetrahydrofuran
TMS: trimethylsilyl group
ATR: total reflection-absorption method
br: broad Reference Example 1

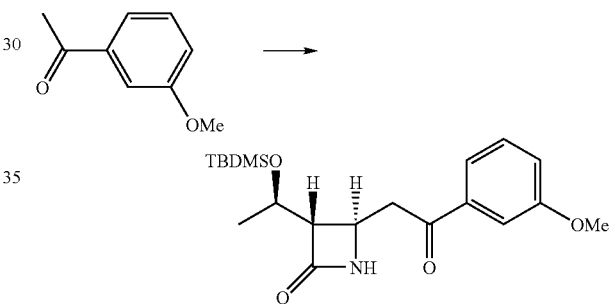

To m-methoxyacetophenone (7.5 g, 50 mmol) and triethylamine (10.5 ml, 75 mmol) in dichloromethane (200 ml) was dropped at 0° C. under stirring trifluoromethanesulfonic acid trimethylsilyl ester (10.9 ml, 60 mmol) and the mixture was stirred at room temperature for 1 hour. To the reaction mixture was added at room temperature (2R,3R)-3-((1R)-1-{[tert-butyl(dimethyl)silyl]oxy}ethyl)-4-oxo-2-azetidinyl acetate (14.4 g, 50 mmol) and zinc iodide (9.6 g, 30 mmol), and the mixture was stirred for 2 hours. To the reaction mixture was added a 5% aqueous potassium hydrogensulfate solution (250 ml), and an organic layer was separated by a separatory funnel. An aqueous layer was extracted with chloroform (100 ml×twice). The extract was combined with the organic layer, dried over magnesium sulfate, filtered and concentrated. The residue was purified with silica gel chromatography (silica gel 400 g, hexane:ethyl acetate=2:1~0:1) to give (3S,4R)-3-((1R)-1-{[tert-butyl(dimethyl)silyl]oxy}ethyl)-4-[2-(3-methoxyphenyl)-2-oxoethyl]azetidin-2-one (15.91 g, yield 84%) as a pale yellowish solid.

$^1$H NMR (400 MHz, CDCl$_3$) δ 0.079 (s, 3 H), 0.086 (s, 3 H), 0.88 (s, 9 H), 1.26 (d, 3 H, J=6.2 Hz), 2.89 (dd, 1 H, J=5.3, 2.2 Hz), 3.16 (dd, 1 H, J=17.7, 10.2 Hz), 3.45 (dd, 1 H, J=17.7, 3.0 Hz), 3.87 (s, 3 H), 4.10-4.15 (m, 1 H), 4.20-4.26 (m, 1 H), 6.11 (br s, 1 H), 7.15 (ddd, 1 H, J=8.0, 2.6, 0.9 Hz), 7.40 (t, 1 H, J=8.0 Hz), 7.47 (dd, 1 H, J=2.6, 1.6 Hz), 7.51-7.53 (m, 1 H).

Reference Example 2

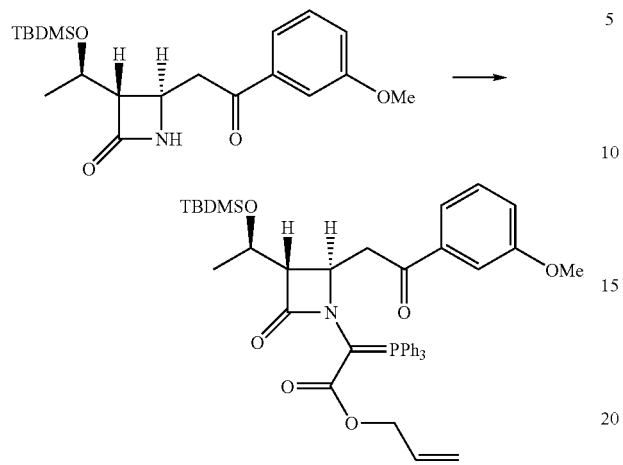

(3S,4R)-3-((1R)-1-{[tert-Butyl(dimethyl)silyl]oxy}ethyl)-4-[2-(3-methoxyphenyl)-2-oxoethyl]azetidin-2-one obtained in Reference example 1 (15.67 g, 41.5 mmol) and allyl glyoxalate monohydrate (7.14 g, 54 mmol) were dissolved in toluene (400 ml), and the mixture was refluxed for 8 hours while excluding resulting water with Dean Stark trap. The reaction solution was concentrated. The residue and 2,6-lutidine (6.67 g, 62.3 mmol) was dissolved in THF (200 ml). Thereto was dropped at −20° C. thionyl chloride (7.4 g, 62.3 mmol) and the mixture was stirred for 30 minutes, followed by stirring for 30 minutes at room temperature. To the reaction mixture was added THF (200 ml), the insoluble materials were filtered under an atmosphere of nitrogen, and washed with THF. The filtrate and the washed solution were combined and concentrated. The residue was dissolved in 1,4-dioxane (600 ml), and thereto were added 2,6-lutidine (9.8 g, 91.3 mmol) and triphenylphosphine (24.0 g, 91.3 mol), followed by stirring at 60° C. for 4 hours. After cooling, the reaction mixture was concentrated, and ethyl acetate (500 ml) was added to the residue. The mixture was washed with brine (100 ml×3 times), dried over magnesium sulfate, and concentrated. The residue was purified with silica gel column chromatography (silica gel 500 g, hexane:ethyl acetate=2:1~1:1) to give allyl {(2R,3S)-3-((1R)-1-{[tert-butyl(dimethyl)silyl]oxy}ethyl)-2-[2-(3-methoxyphenyl)-2-oxoethyl]-4-oxoazetidin-1-yl}(triphenylphosphoranilidene)acetate (23.8 g, yield 78%) as a yellow amorphous.

Reference Example 3

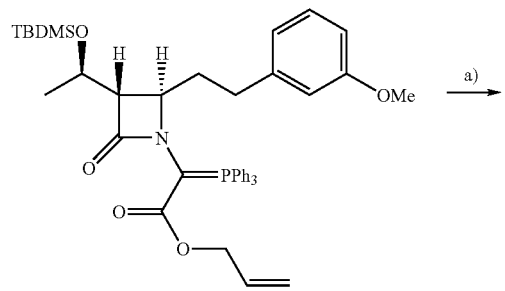

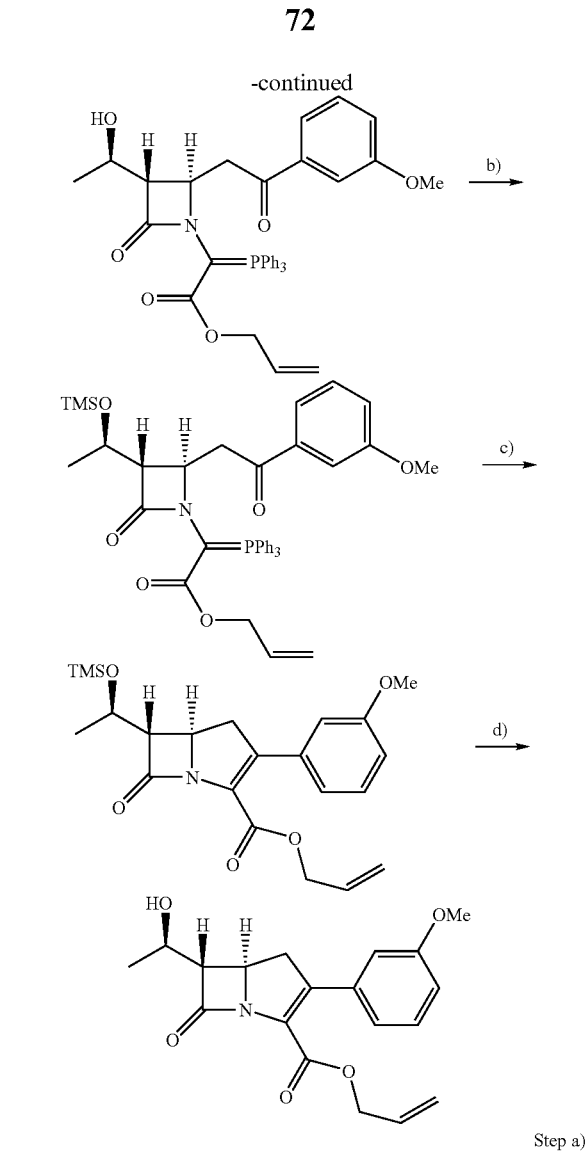

Step a)

Allyl {(2R,3S)-3-((1R)-1-{[tert-butyl(dimethyl)silyl]oxy}ethyl)-2-[2-(3-methoxyphenyl)-2-oxoethyl]-4-oxoazetidin-1-yl}(triphenylphosphoranilidene)acetate (3.0 g) prepared by Reference example 2 was dissolved at room temperature in a 70% aqueous trifluoroacetic acid solution (10 ml). To the reaction mixture was added ethyl acetate (100 ml) and the mixture was washed with saturated brine (100 ml×twice), and a saturated hydrogencarbonate solution (100 ml×twice), dried over magnesium sulfate, filtered, and concentrated to give allyl {(2R,3S)-3-[(1R)-1-hydroxyethyl]-2-[2-(3-methoxyphenyl)-2-oxoethyl]-4-oxoazetidin-1-yl}(triphenylphosphoranilidene)acetate (3.09 g) as a pale yellow amorphous. This product was subjected to next reaction without further purification.

Step b)

Allyl {(2R,3S)-3-[(1R)-1-hydroxyethyl]-2-[2-(3-methoxyphenyl)-2-oxoethyl]-4-oxoazetidin-1-yl}(triphenylphosphoranilldene)acetate (3.09 g) prepared by step a) and triethylamine (0.86 ml, 6.12 mmol) were dissolved in THF (15 ml), and thereto was added at 0° C. chlorotrimethylsilane (0.62 ml, 4.9 mmol), followed by stirring for 30 minutes. Triethylamine (0.86 ml, 6.12 mmol) and chlorotrimethylsilane (0.62 ml, 4.9 mmol) were further added thereto and the mixture was stirred for 20 minutes. To the reaction mixture was added ethyl acetate, and the mixture was washed with aqueous hydrogencarbonate solution/saturated brine (1:1, 50 ml×twice), and saturated brine (100 ml), dried over magnesium sulfate, filtrated, and concentrated to give allyl ((2R,3S)-2-[2-(3-methoxyphenyl)-2-oxoethyl]-4-oxo-3-{(1R)-1-[(trimethylsilyl)oxy]ethyl}azetidin-1-yl)(triphenylphosphoranilidene)acetate (3.26 g) as a yellow oil. This product was subjected to next reaction without further purification.

Step c)

Allyl ((2R,3S)-2-[2-(3-methoxyphenyl)-2-oxoethyl]-4-oxo-3-{(1R)-1-[(trimethylsilyl)oxy]ethyl}azetidin-1-yl)(triphenylphosphoranilldene)acetate prepared by step b) was dissolved in xylene (100 ml), and thereto was added N,O-bistrimethylsilylacetoamide (1.0 ml), followed by refluxing for 4 hours. After cooling the reaction mixture was concentrated, and the residue was purified with column chromatography (silica gel 100 g, chloroform:methanol=100:0~100:3) to give allyl (5R,6S)-3-(3-methoxyphenyl)-7-oxo-6-{(1R)-1-[(trimethylsilyl)oxy]ethyl}-1-azabicyclo[3.2.0]hept-2-ene-2-carboxylate (1.70 g, quantatively) as a pale yellow oil.

LC/MS (EI) 416 (M+1), 344 (M+1-TMS).

$^1$H NMR (400 MHz, CDCl$_3$) δ 0.15 (s, 9 H), 1.30 (d, 3 H, J=6.2 Hz), 3.13-3.31 (m, 3 H), 3.80 (s, 3 H), 4.19-4.24 (m, 2 H), 4.60-4.66 (m, 1 H), 4.69-4.74 (m, 1 H), 5.16-5.19 (m, 1 H), 5.24-5.29 (m, 1 H), 5.81-5.90 (m, 1 H), 6.86-6.93 (m, 3 H), 7.24-7.28 (m, 1 H).

Step d)

Allyl (5R,6S)-3-(3-methoxyphenyl)-7-oxo-6-{(1R)-1-[(trimethylsilyl)oxy]ethyl}-1-azabicyclo[3.2.0]hept-2-ene-2-carboxylate (1.70 g, 4.09 mmol) prepared by step c) was dissolved in THF (40 ml) and water (20 ml), and the mixture was cooled in a water bath and thereto was gradually dropped 1N hydrochloric acid using a pH meter so as to become pH=2.5. After 15 minutes, thereto were added an aqueous saturated sodium hydrogencarbonate solution (50 ml) and saturated brine (50 ml), and the mixture was extracted with chloroform (50 ml×3 times). The organic layers were combined and dried over magnesium sulfate, filtered, and concentrated to give allyl (5R,6S)-6-[(1R)-1-hydroxyethyl]-3-(3-methoxyphenyl)-7-oxo1-azabicyclo[3.2.0]hept-2-ene-2-carboxylate (1.37 g, 3.99 mmol, yield 98%) as a pale yellow oil.

LC/MS (EI) 344 (M+1).

$^1$H NMR (400 MHz, CDCl$_3$) δ 1.38 (d, 3 H, J=6.3 Hz), 1.63 (br s, 1 H), 3.17-3.33 (m, 3 H), 3.80 (s, 3 H), 4.23-4.33 (m, 2 H), 4.60-4.66 (m, 1 H), 4.69-4.75 (m, 1 H), 5.16-5.20 (m, 1 H), 5.23-5.28 (m, 1 H), 5.80-5.90 (m, 1 H), 6.87-6.94 (m, 3 H), 7.25-7.29 (m, 1 H).

Reference Example 4

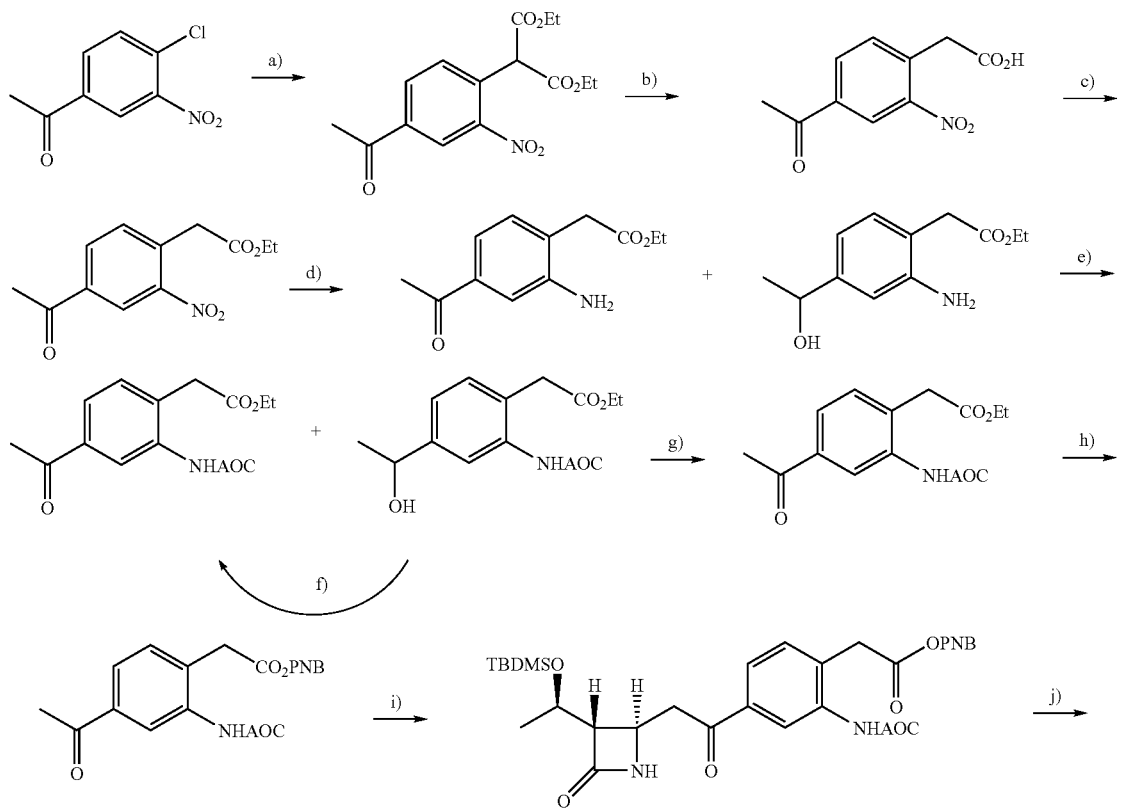

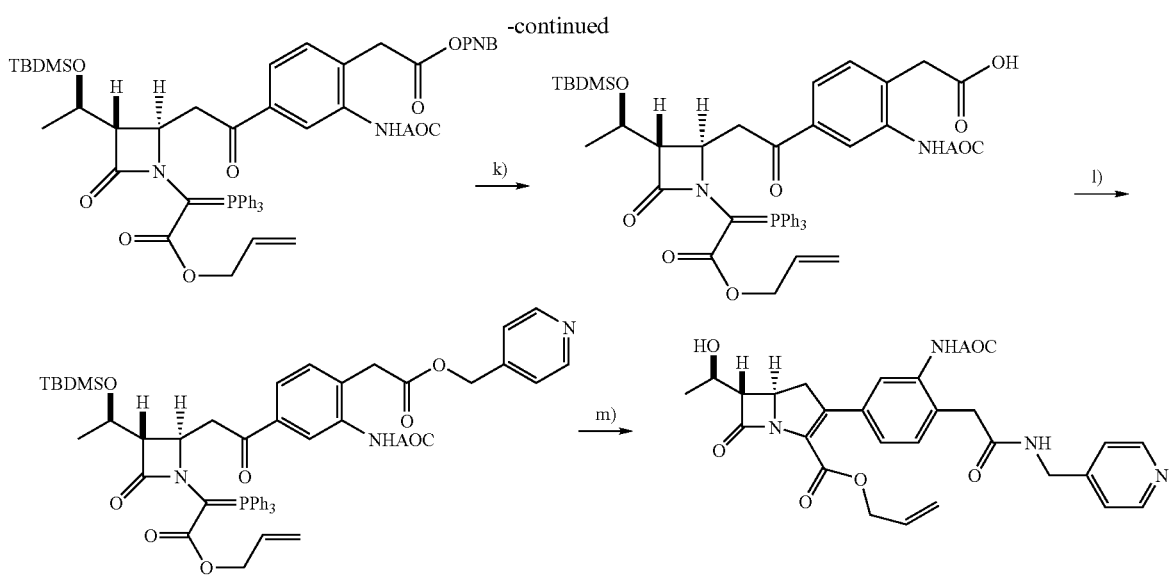

Step a)
Diethyl (4-acetyl-2-nitrophenyl)malonate

To a 20% ethanol solution containing sodium ethoxide (68.7 g) was dropped at 4~50° C. under stirring diethyl malonate (32.4 g), followed by stirring for 10 minutes. To the mixture was added at room temperature 4-chloro-3-nitroacetophenone (20.2 g) and the mixture was stirred for 3 hours. To the reaction mixture were added 2N hydrochloric acid (200 mL) and chloroform (200 mL), and the organic layer was separated. The aqueous layer was extracted with chloroform (2×100 mL), and the organic layers were combined, dried over magnesium sulfate, filtered, and the solvent was evaporated in vacuo to give a mixture of the object compound and diethyl malonate (54.1 g, quantitatively). The mixture was subjected to next reaction without further purification.

The sample for analysis was purified with silica gel column chromatography (hexane/ethyl acetate).

$^1$H NMR (400 MHz, CDCl$_3$) δ 1.29 (t, 6 H,. J=7.1 Hz), 2.67 (s, 3 H), 4.280 (q, 2 H, J=7.1 Hz), 4.283 (q, 2 H, J=7.1 Hz), 5.33 (s, 1 H), 7.67 (d, 1 H, J=8.1 Hz), 8.20 (dd, 1 H, J=8.1, 1.8 Hz), 8.60 (d, 1 H, J=1.8 Hz).

Step b)

(4-Acetyl-2-nitrophenyl)acetic acid

A mixture of diethyl(4-acetyl-2-nitrophenyl)malonate and diethyl malonate (54.1 g) prepared by step a) was dissolved in 4M HCl (800 mL)/dioxane (800 mL), and the solution was stirred at 100° C. for 8 hours. After cooling, dioxane was removed in vacuo, and the aqueous layer was extracted with chloroform (200 mL×1, 100 mL×2). The organic layers were combined, dried over magnesium sulfate, filtered, and the solvent was removed in vacuo to give the object compound (23.1 g, quantitatively) as a brown solid.

$^1$H NMR (400 MHz, CDCl$_3$) δ 2.68 (s, 3 H), 4.14 (s, 2 H), 7.50 (d, 1 H, J=7.9 Hz), 8.18 (dd, 1 H, J=1.7, 7.9 Hz), 8.68 (d, 1 H, J=1.7 Hz).

Step c)

Ethyl (4-acetyl-2-nitrophenyl)acetate (4-Acetyl-2-nitrophenyl)acetic acid (23.1 g) prepared by step b) was dissolved in ethanol (500 mL) and thereto was added concentrated hydrochloric acid (50 mL), followed by refluxing for 6 hours. After cooling, ethanol was removed in vacuo, and to the aqueous layer were added ethyl acetate (300 mL) and a saturated sodium hydrogencarbonate solution (100 mL). The mixture was neutralized with addition of sodium hydrogencarbonate powder. The aqueous layer was separated and the organic layer was washed with a saturated sodium hydrogencarbonate solution (100 mL) and saturated brine (100 mL), dried over magnesium sulfate, filtered, and the solvent was removed in vacuo. The residue was purified with column chromatography (SiO$_2$ 100 g, hexane/ethyl acetate 1:1) to give the object compound (23.2 g, 91%) as a brown oil. The aqueous layer was acidified with hydrochloric acid and extracted with chloroform to recover (4-acetyl-2-nitrophenyl)acetic acid (1.8 g, 8%).

$^1$H NMR (400 MHz, CDCl$_3$) δ 1.26 (t, 3 H, J=7.1 Hz), 2.67 (s, 3 H), 4.09 (s, 2 H), 4.18 (q, 2 H, J=7.1 Hz), 7.49 (d, 1 H, J=7.9 Hz), 8.16 (dd, 1 H, J=1.8, 7.9 Hz), 8.65 (d, 1 H, J=1.8 Hz). LCMS (EI) 252 (M+1)+.

Step d)

A mixture of ethyl (4-acetyl-2-aminophenyl)acetate and ethyl [2-amino-4-(1-hydroxyethyl)phenyl]acetate Ethyl (4-acetyl-2-nitrophenyl)acetate (23.2 g) prepared by step c) was dissolved in ethanol (660 mL) and thereto was added Pd—C (5%, 5.9 g). The mixture was stirred at ordinary pressure under an atmosphere of hydrogen for 9.5 hours. Pd—C was filtered off with Celite, and the solvent was removed in vacuo to give the object compound (20.4 g, quantitatively) as a brown oil. Ratio of the ketone compound and the alcohol compound was 1:2 by NMR analysis. This product was subjected to next reaction without further purification.

LCMS (EI) 222 (M+1)+ketone, 224 (M+1)+alcohol.

Step e)

Ethyl (4-acetyl-2-{[(allyloxy)carbonyl]amino}phenyl)acetate and ethyl [2-{[(allyloxy)carbonyl]amino}-4-(1-hydroxyethyl)phenyl]acetate A mixture of ethyl (4-acetyl-2-aminophenyl)acetate and ethyl [2-amino-4-(1-hydroxyethyl)phenyl]acetate (20.4 g) prepared by step d) was dissolved in pyridine (184 mL) and thereto was dropped at room temperature allyloxycarbonyl chloride (22.2 g), followed by stirring for 30 minutes. To the reaction mixture were added a saturated ammonium chloride solution (100 mL) and saturated brine (100 mL), and then pyridine was removed in vacuo. To the aqueous layer was added 2M hydrochloric acid (200 mL) and the mixture was extracted with ethyl acetate (3×100 mL). The organic layers were combined, washed with 2M hydrochloric acid (3×50 mL) and saturated brine (50 mL), filtered and the solvent was removed in vacuo. The residue was purified with column chromatography (SiO$_2$ 500 g, hexane/ethyl acetate 3:1~1:1) to give ethyl (4-acetyl-2-{[(allyloxy)carbonyl]amino}phenyl)acetate (7.34 g, 26%) as a gray oil, and ethyl [2-{[(allyloxy)carbonyl]amino}-4-(1-hydroxyethyl)phenyl]acetate (14.1 g, 50%) as a purple oil.

Ethyl (4-acetyl-2-{[(allyloxy)carbonyl]amino}phenyl)acetate $^1$H NMR (400 MHz, CDCl$_3$) δ 1.28 (t, 3 H, J=7.1 Hz), 2.60 (s, 3 H), 3.68 (s, 2 H), 4.18 (q, 2 H, J=7.1 Hz), 4.69-4.71 (m, 2 H), 5.26-5.30 (m, 1 H), 5.37-5.41 (m, 1 H), 5.95-6.05 (m, 1 H), 7.30 (d, 1 H, J=8.0 Hz), 7.69 (dd, 1 H, J=1.8, 8.0 Hz), 8.12 (bs, 1 H), 8.42 (bs, 1 H). LCMS (EI) 306 (M+1)+.

Ethyl [2-{[(allyloxy)carbonyl]amino}-4-(1-hydroxyethyl)phenyl]acetate $^1$H NMR (400 MHz, CDCl$_3$) δ 1.28 (t, 3 H, J=7.1 Hz), 1.49 (d, 3 H, J=6.4 Hz), 3.61 (s, 2 H), 4.16 (q, 2 H, J=7.1 Hz), 4.67-4.69 (m, 2 H), 4.89 (q, 1 H, J=6.4 Hz), 5.24-5.28 (m, 1 H), 5.34-5.40 (m, 1 H), 5.94-6.03 (m, 1 H), 7.12 (dd, 1 H, J=1.7, 7.8 Hz), 7.18 (d, 1 H, J=7.8 Hz), 7.81 (bs, 1 H), 8.07 (bs, 1 H). LCMS (EI) 308 (M+1)+.

Step f)

Ethyl (4-acetyl-2-{[(allyloxy)carbonyl]amino}phenyl)acetate

Ethyl [2-{[(allyloxy)carbonyl]amino}-4-(1-hydroxyethyl)phenyl]acetate (10.3 g) prepared by step e) was dissolved in acetone (30 mL) and thereto was added at room temperature Jons' reagent (10 mL), followed by stirring for 30 minutes. To the reaction solution were added saturated bicarbonate solution (50 mL) and saturated brine (100 mL), and the mixture was extracted with ethyl acetate (3×50 mL). The organic layer was combined, dried over magnesium sulfate, filtered and the solvent was removed in vacuo to give a crude product. The crude product was combined with the crude product prepared separately prepared in a scale of 1 g and purified with column chromatography (SiO$_2$ 300 g, hexane/ethyl acetate 1:1) to give the object compound (10.3 g, 85%) as a yellow oil.

Step g)

(4-Acetyl-2-{[(allyloxy)carbonyl]amino}phenyl)acetic acid

Ethyl (4-acetyl-2-{[(allyloxy)carbonyl]amino}phenyl)acetate (17.6 g) prepared by step e) and step f) was dissolved in ethanol (176 mL) and thereto was added at 0° C. 1M aqueous NaOH solution (132 mL), followed by stirring for 1 hour. To the reaction solution was added 2M hydrochloric acid (400 mL), and ethanol was removed in vacuo. The resulting solid was collected by filtration and washed with 2M hydrochloric acid, and dried in vacuo to give the object compound as a pale brown solid (11.2 g, 70%). Further the aqueous layer was extracted with ethyl acetate, dried over magnesium sulfate, filtered, and the solvent was removed in vacuo to give the object compound (3.58 g, 22%) as a brown solid.

$^1$H NMR (400 MHz, CDCl$_3$) δ 2.59 (s, 3 H), 3.74 (s, 2 H), 4.68-4.70 (m, 2 H), 5.27 (bd, 1 H, J=10.8 Hz), 5.35 (bd, 1 H, J=15.3 Hz), 5.60 (bs, 1 H), 7.34 (d, 1 H, J=7.9 Hz), 7.70 (bs, 1 H), 7.74 (dd, 1 H, J=1.5, 7.9 Hz), 8.25 (bs, 1 H).

Step h)

4-Nitrobenzyl (4-acetyl-2-{[(allyloxy)carbonyl]amino}phenyl)acetate

To (4-acetyl-2-{[(allyloxy)carbonyl]amino}phenyl)acetic acid (10.9 g) prepared by step g) and triethylamine (11 mL) in DMF (100 mL) was added at room temperature p-nitrobenzyl bromide (17.0 g), and the mixture was stirred at room temperature for 1 hour. To the reaction mixture were added saturated brine (500 mL) and water (300 mL), and the mixture was extracted with ethyl acetate (200 mL, 2×100 mL). The organic layers were combined, washed with saturated brine (100 mL), dried over magnesium sulfate, filtered and the solvent was removed in vacuo. The residue was purified with column chromatography (SiO$_2$ 300 g, hexane/ethyl acetate/chloroform=3:1:4~0:1:1) to give the object compound (16.4 g, 98%) as a pale brown solid. Further the product was recrystallized from chloroform/hexane to give the object compound (10.4 g, 64%) as a white solid.

$^1$H NMR (400 MHz, CDCl$_3$) δ 2.61 (s, 3 H), 3.78 (s, 2 H), 4.68-4.70 (m, 2 H), 5.24 (s, 2 H), 5.27-5.30 (m, 1 H), 5.35-5.40 (m, 1 H), 5.93-6.01 (m, 1 H), 7.32 (d, 1 H, J=8.0 Hz), 7.46-7.50 (m, 2 H), 7.71 (dd, 1 H, J=1.8, 8.0 Hz), 7.73 (bs, 1 H), 8.22 (td, 2 H, J=2.3, 6.8 Hz), 8.38 (bs, 1 H). LCMS (EI) 413 (M+1)+.

Step i)

4-Nitrobenzyl (2-{[(allyloxy)carbonyl]amino}-4-{[(2R,3S)-3-((1R)-1-{[tert-butyl(dimethyl)silyl]oxy}ethyl)-4-oxoazetidin-2-yl]acetyl}phenyl)acetate To 4-nitrobenzyl (4-acetyl-2-{[(allyloxy)carbonyl]amino}phenyl)acetate (10.0 g) and triethylamine (8.2 mL) in dichloromethane (100 mL) was dropped at 0° C. trifluoromethanesulfonic acid trimethylsilyl ester (11.9 g). After detecting the production of silylenol ether by TLC, (2R,3R)-3-((1R)-1-{[tert-butyl(dimethyl)silyl]oxy}ethyl)-4-oxo-2-azetidinyl acetate (6.98 g) and zinc iodide (4.65 g) were added thereto at 0° C. After stirring for 1 hour, further (2R,3R)-3-((1R)-1-{[tert-butyl(dimethyl)silyl]oxy}ethyl)-4-oxo-2-azetidinyl acetate (3.0 g) was added thereto and the mixture was stirred at room temperature for 14 hours. To the reaction mixture were added a 5% aqueous potassium hydrogensulfate solution (380 mL) and saturated brine (100 mL), and the mixture was extracted with ethyl acetate (200 mL, 2×100 mL). The organic layers were combined, dried over magnesium sulfate, filtered and the solvent was removed in vacuo.

The residue was purified with column chromatography (SiO₂ 500 g, hexane/ethyl acetate 1:1~1:3) to give the object compound (11.4 g, 70%) as a pale amorphous.

¹H NMR (400 MHz, CDCl₃) δ 0.08 (s, 3 H), 0.08 (s, 3 H), 0.88 (s, 9 H), 1.25 (d, 3 H, J=6.2 Hz), 2.90 (dd, 1 H, J=2.2, 5.1 Hz), 3.18 (dd, 1 H, J=10.1, 17.8 Hz), 3.45 (dd, 1 H, J=3.0, 17.8 Hz), 3.79 (s, 2 H), 4.10-4.15 (m, 1 H), 4.20-4.26 (m, 1 H), 4.69 (td, 2 H, J=1.4, 4.4 Hz), 5.25 (s, 2 H), 5.27-5.31 (m, 1 H), 5.35-5.40 (m, 1 H), 5.93-6.03 (m, 1 H), 6.12 (bs, 1 H), 7.34 (d, 1 H, J=8.0 Hz), 7.47-7.50 (m, 2 H), 7.70 (dd, 1 H, J=1.8, 8.0 Hz), 7.83 (bs, 1 H), 8.21-8.24 (m, 2 H), 8.39 (bs, 1 H). LCMS (EI) 640 (M+1)+.

Step j)

Allyl [(2R,3S)-2-[2-(3-{[(allyloxy)carbonyl]amino}-4-{2-[(4-nitrobenzyl)oxy]-2-oxoethyl}phenyl)-2-oxoethyl]-3-((1R)-1-{[tert-butyl(dimethyl)silyl]oxy}ethyl)-4-oxoazetidin-1-yl](triphenylphosphoranilidene)acetate 4-Nitrobenzyl (2-{[(allyloxy)carbonyl]amino}-4-{[(2R,3S)-3-((1R)-1-{[tert-butyl(dimethyl)silyl]oxy}ethyl)-4-oxoazetidin-2-yl]acetyl}phenyl)acetate (11.4 g) prepared by step i) was treated in the same method as Reference example 2 to give the object compound (10.4 g, 59%) as a pale brown amorphous.

LCMS (EI) 998 (M+1)+.

Step k)

(2-{[(Allyloxy)carbonyl]amino}-4-{[(2R,3S)-1-[2-(allyloxy)-2-oxo-1-(triphenylphosphoranihdene)ethyl]-3-((1R)-1-{[tert-butyl(dimethyl)silyl]oxy}ethyl)-4-oxoazetidin-2-yl]acetyl}phenyl)acetic acid Allyl [(2R,3S)-2-[2-(3-{[(allyloxy)carbonyl]amino}-4-{2-[(4-nitrobenzyl)oxy]-2-oxoethyl}phenyl)-2-oxoethyl]-3-((1R)-1-{[tert-butyl(dimethyl)silyl]oxy}ethyl)-4-oxoazetidin-1-yl](triphenylphosphoranilidene)acetate (10.4 g) prepared by step j) was dissolved in THF (200 mL) and thereto was added zinc (3.4 g) to give a suspension. Further thereto was added at room temperature 2M ammonium chloride solution (26 mL) and the mixture was stirred for 2 hours. Thereto was added acetic acid (6.3 g) and the mixture was stirred for further 1 hour. To the reaction mixture was added a 5% aqueous potassium hydrogensulfate solution (200 mL) and the mixture was extracted with ethyl acetate (3×100 mL). The extracts were combined, washed with a 5% aqueous potassium hydrogensulfate solution (100 mL), dried over magnesium sulfate, filtered and the solvent was removed in vacuo. The residue was purified with column chromatography (SiO₂ 300 g, chloroform/methanol 98:2~90:10) to give the object compound (9.11 g, quantitatively) as a reddish brown amorphous.

LCMS (EI) 863 (M+1)+.

Step l)

Allyl [(2R,3S)-2-[2-(3-{[(allyloxy)carbonyl]amino}-4-{2-oxo-2-[(pyridine4-ylmethyl)amino]ethyl}phenyl)-2-oxoethyl]-3-((1R)-1-{[tert-butyl(dimethyl)silyl]oxy}ethyl)-4-oxoazetidin-1-yl](triphenylphosphoranilidene)acetate 2-{[(Allyloxy)carbonyl]amino}-4-{[(2R,3S)-1-[2-(allyloxy)-2-oxo-1-(triphenylphosphoranilidene)ethyl]-3-((1R)-1-{[tert-butyl(dimethyl)silyl]oxy}ethyl)-4-oxoazetidin-2-yl]acetyl}phenyl)acetic acid (1.5 g) prepared by step k) and 4-picolylamine (0.67 g) were dissolved in THF (15 mL) and thereto was added WSCl.HCl (0.38 g), followed by stirring for 30 minutes. Further WSCl.HCl (0.38 g) was added thereto and the mixture was stirred for 14 hours. To the reaction mixture was added saturated brine (50 mL) and the mixture was extracted with chloroform (3×50 mL). The organic layers were combined, dried over magnesium sulfate, filtered and the solvent was removed in vacuo to give a crude product (2.92 g, quantitatively).

LCMS (EI) 953 (M+1)+.

Step m)

Allyl (5R,6S)-3-(3-{[(allyloxy)carbonyl]amino}-4-{2-oxo-2-[(pyridin-4-ylmethyl)amino]ethyl}phenyl)-6-[(1R)-1-hydroxyethyl]-7-oxo-1-azabicyclo[3.2.0]hept-2-ene-2-carboxylate Allyl [(2R,3S)-2-[2-(3-{[(allyloxy)carbonyl]amino}-4-{2-oxo-2-[(pyridin-4-ylmethyl)amino]ethyl}phenyl)-2-oxoethyl]-3-((1R)-1-{[tert-butyl(dimethyl)silyl]oxy}ethyl)-4-oxoazetidin-1-yl](triphenylphosphoranilidene)acetate (2.9 g) prepared by step l) was treated in the same method as Referential example 3 to give the object compound (0.58 g) as a brown amorphous. Although this product contained triphenylphosphinoxide, the product was subjected to next reaction without further purification.

Reference Example 5

2-(4-Acetyl-2-chlorophenyl)ethyl acetate

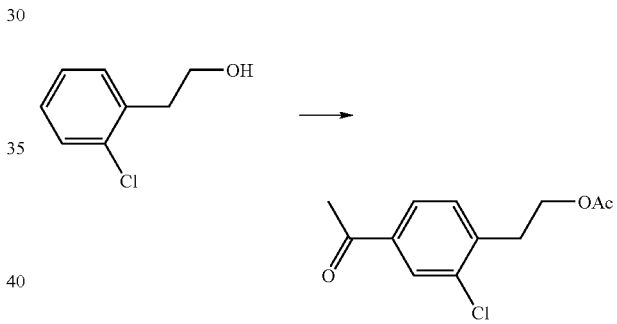

2-Chlorophenethyl alcohol (10 g) was dissolved in hexane (300 ml) and thereto was added aluminum chloride (28.1 g). Under ice cooling, acetyl chloride (15.0 g) was dropped thereto. After 1 hour, the reaction mixture was added in ice water, then extracted with ethyl acetate, and washed with brine. The organic layer was dried, concentrated and the residue was purified with silica gel column chromatography (hexane:acetic acidethyl=3:1) to give the object compound (4.47 g).

¹H NMR (400 MHz, CDCl₃) δ 2.03 (s, 3H), 2.59 (s, 3H), 3.13 (t, 2H, J=6.8 Hz), 4.33 (t, 2H, J=6.8 Hz), 7.46 (d, 1H, J=8.3 Hz), 7.76 (dd, 1H, J=8.3, 2.2 Hz), 7.85 (d, 1H, J=2.2 Hz)

Reference Example 6

1-[3-Chloro-4-(2-hydroxyethyl)phenyl]ethanone

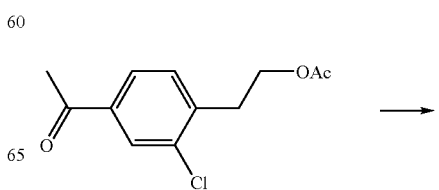

-continued

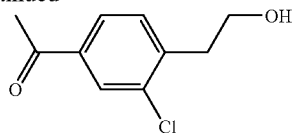

2-(4-Acetyl-2-chlorophenyl)ethyl acetate (4.87 g) was dissolved in methanol (80 ml), and thereto was added concentrated hydrochloric acid (20 ml), followed by refluxing. Four hours later the temperature of the reaction mixture was kept at room temperature, and methanol was removed in vacuo. Then the residue was diluted with ethyl acetate, washed with brine, dried and concentrated to give the object compound (4.42 g).

$^1$H NMR (400 MHz, CDCl$_3$) δ 2.59 (s, 3H), 3.08 (t, 2H, J=6.6 Hz), 3.93 (t, 2H, J=6.8 Hz), 7.46 (d, 1H, J=8.3 Hz), 7.76 (dd, 1H, J=8.3, 2.2 Hz), 7.89 (d, 1H, J=2.2 Hz)

Reference Example 7

4-Acetyl-2-cchlorophenylacetic acid

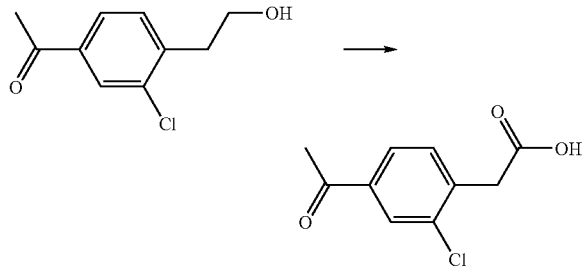

1-[3-Chloro-4-(2-hydroxyethyl)phenyl]ethanone (4.42 g) was dissolved in acetone (50 ml), and thereto was added Jones reagent (13 ml). The reaction mixture was diluted with ethyl acetate, washed with brine, dried, and concentrated. The residue was purified with silica gel column chromatography (chloroform:methanol=25:1) to give the object compound (2.65 g).

$^1$H NMR (400 MHz, CDCl$_3$) δ 2.59 (s, 3H), 3.89 (s, 2H), 7.51 (d, 1H, J=8.3 Hz), 7.84 (d, 1H, J=8.3 Hz), 7.90 (s, 1H)

Reference Example 8

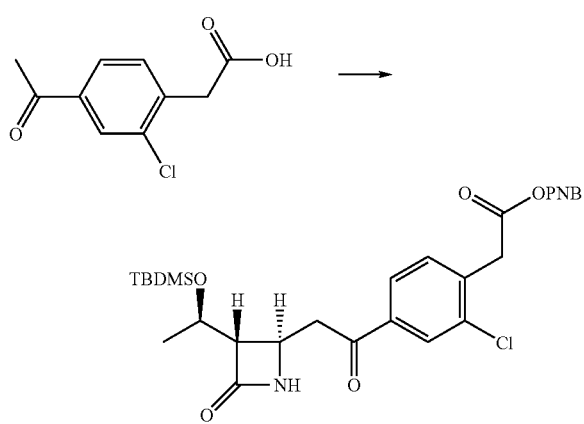

To 4-acetyl-2-chlorophenylacetic acid (2.65 g, 12.5 mmol) in DMF solution (26 mL) were added triethylamine (3.5 ml, 25 mmol) and 4-nitrobenzyl bromide (5.4 g, 25mol), and the mixture was stirred at room temperature for 30 minutes. The reaction mixture was added to an ice cooled saturated potassium hydrogencarbonate solution, the organic layer was separated by a separatory funnel, and the aqueous layer was extracted with ethyl acetate. The organic layers were combined and dried over sodium sulfate, filtered and concentrated. The residue was purified with silica gel chromatography (silica gel 180 ml, hexane:EtOAc=2:1→1:1) to give 4-nitrobenzyl (4-acetyl-2-chlorophenyl)acetate (3.56 g, yield, 82%) as white crystals. The product was subjected to next reaction without further purification. To 4-nitrobenzyl (4-acetyl-2-chlorophenyl)acetate (3.56 g, 11.4 mmol) and triethylamine (2.0 ml, 15.9 mmol) in dichloromethane (36 ml) was dropped at 0° C. under stirring trifluoromethanesulfonic acid trimethylsilyl ether (2.4 ml, 14.8 mmol), and the mixture was stirred for 20 minutes. To the reaction mixture were added at 0° C. dichloromethane (50 mL), (2R,3R)-3-((1R)-1-{[tert-butyl(dimethyl)silyl]oxy}ethyl)-4-oxo-2-azetidinyl acetate (4.6 g, 15.9 mmol), and zinc iodide (2.2 g, 6.8 mmol), and then the ice bath was removed. The mixture was stirred at room temperature for 4.5 hours and then added to an ice cooled saturated potassium hydrogencarbonate solution. The organic layer was separated by a separatory funnel and the aqueous layer was extracted with ethyl acetate. The organic layers were combined, dried over sodium sulfate, filtered, and concentrated. The residue was purified with silica gel chromatography (silica gel 180 ml, hexane:EtOAc=4:1→0:1) to give 4-nitrobenzyl(4-{[(2R,3S)-3-((1R)-1-{[tert-butyl(dimethyl)silyl]oxy}ethyl)-4-oxoazetidin-2-yl]acetyl}-2-chlorophenyl)acetate (5.2 g, yield 79.7%) as a white solid.

$^1$H NMR (400 MHz, CDCl$_3$) δ 0.079 (s, 6 H), 0.88 (s, 9 H), 1.26 (d, 3 H, J=6.2 Hz), 2.88 (dd, 1 H, J=5.2, 2.4 Hz), 3.14 (dd, 1 H, J=18, 10 Hz), 3.43 (dd, 1 H, J=17.6, 2.8 Hz), 3.92 (s, 2 H), 4.09-4.12 (m, 1 H), 4.21-4.23 (m, 1 H), 5.26 (s, 2 H), 6.06 (br-s, 1 H), 7.50-7.54 (m, 3 H), 7.82 (dd, 1 H, J=8.4, 2.0 Hz), 7.89 (d, 1 H, J=2.0 Hz), 8.22 (dd, 2 H, J=6.8, 4.8 Hz).

Reference Example 9

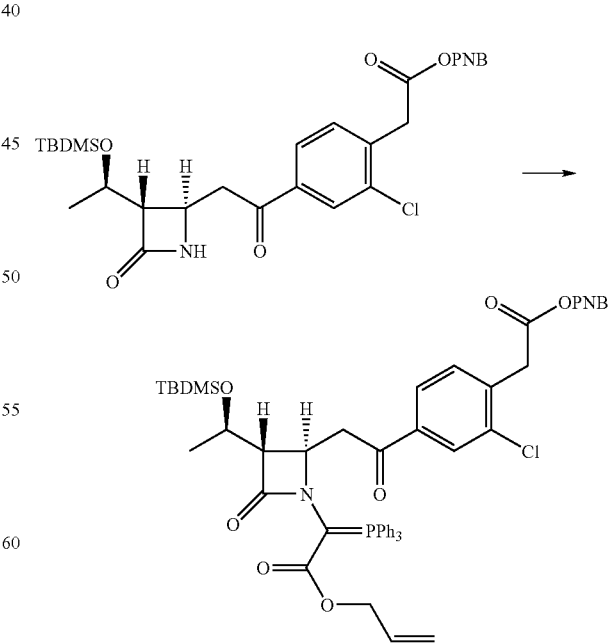

4-Nitrobenzyl (4-{[(2R,3S)-3-((1R)-1-{[tert-butyl(dimethyl)silyl]oxy}ethyl)-4-oxoazetidin-2-yl]acetyl}-2-chlorophenyl)acetate (5.2 g, 9.6 mmol) prepared by Reference example 8 and allyl glyoxalate monohydrate (1.8 g, 13.6 mmol) were dissolved in toluene (105 ml), and the mixture was refluxed for 4 hours while eliminating the resulted water with Dean Stark trap. The reaction solution was concentrated, and the residue and 2,6-lutidine (1.9 mL, 16.3 mmol) were dissolved in THF (101 ml). At between −20° C. to −30° C., thionyl chloride (0.93 mL, 12.7 mmol) was dropped thereto and stirred for 12 minutes. The insoluble materials were filtered off under an atmosphere of nitrogen, washed with THF, and the filtrate was combined with the washed solution, followed by concentration. The residue was dissolved in 1,4-dioxane (108 ml) and thereto were added triphenylphosphine (5.2 g, 19.9 mmol) and 2,6-lutidine (2.4 mL, 20.8 mmol). The mixture was stirred at 40° C. for 6 hours. After cooling, the reaction solution was concentrated, and to the residue was added ethyl acetate. The mixture was washed with brine, dried over magnesium sulfate, and concentrated. The residue was purified with silica gel column chromatography (silica gel 180 mL, hexane/ethyl acetate=2:1→1:2) to give allyl {[(2R,3S)-3-((1R)-1-{[tert-butyl(dimethyl)silyl]oxy}ethyl)-2-[2-(3-chloro-4-{2-[(4-nitrobenzyl)oxy]-2-oxoethyl}phenyl)-2-oxoethyl]-4-oxoazetidin-1-yl]}(triphenylphosphoranilidene)acetate (5.4 g, yield 64%) as a pale yellow amorphous.

LC/MS (EI) 933 (M+1)

Reference Example 10

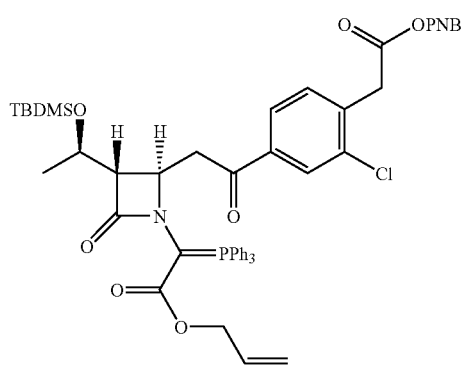

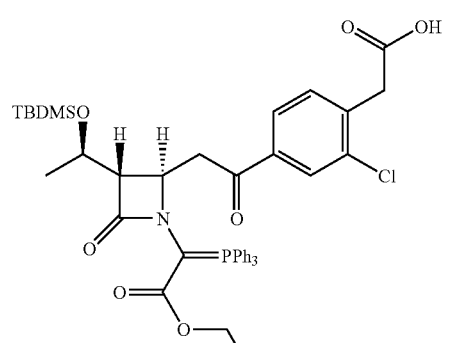

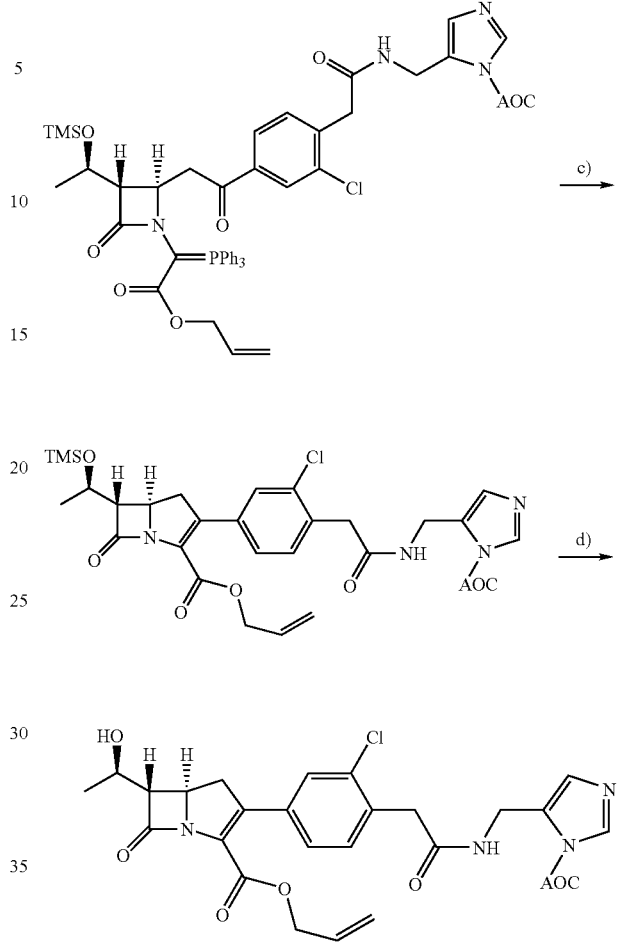

Step a)

Allyl {[(2R,3 S)-3-((1R)-1-{[tert-butyl(dimethyl)silyl]oxy}ethyl) -2-[2-(3-chloro-4-{2-[(4-nitrobenzyl)oxy]-2-oxoethyl}phenyl)-2-oxoethyl]-4-oxoazetidin-1-yl]}(triphenylphosphoraniliden)acetate (2.0 g, 2.1 mmol) prepared by Reference example 9 was dissolved in THF (40 mL), and thereto were added zinc powder 2.1 g (31.5 mol), ammonium chloride solution (2M, 16 mL, 31.5 mmol), and acetic acid (1.8 mL, 31.5 mmol), and the mixture was stirred at room temperature for 5 hours. The reaction mixture was filtered with Celite (washed with ethyl acetate), and the filtrate was washed with a 5% aqueous potassium hydrogensulfate solution and saturated brine, dried over sodium sulfate, filtered, and concentrated. The residue was purified silica gel column chromatography (silica gel 60 mL, chloroform/methanol=1: 0→25:1) to give (4-{[(2R,3S)-1-[2-(allyloxy)-2-oxo-1-(triphenylphosphoranilidene)ethyl]-3-((1R)-1-{[tert-butyl(dimethyl)silyl]oxy}ethyl)-4-oxoazetidin-2-yl]acetyl}-2-chlorophenyl)acetic acid (1.7 g, yield, 98%) as a pale yellow amorphous.

LC/MS (EI) 799 (M+1)

Step b)
(4-{[(2R,3S)-1-[2-(allyloxy)-2-oxo-1-(triphenylphosphoranilidene)ethyl]-3-((1R)-1-{[tert-butyl(dimethyl)silyl]oxy}ethyl)-4-oxoazetidin-2-yl]acetyl}-2-chlorophenyl)acetic acid (1.4 g, 1.75 mmol) prepared by step a), was added to 4-aminomethylimidazole dihydrate (0.51 g, 3.0 mmol) and triethylamine (0.83 ml, 6.0 mmol) in an ice cooled DMF (20 mL), and then thereto were added 1-hydroxybenzotriazole (0.47 g, 3.5 mmol) and EDCI (0.67 g, 3.5 mmol), followed by stirring for 5 minutes. After removal of the ice bath, the mixture was stirred for 150 minutes. To the reaction mixture were added ice water and ethyl acetate. The mixture was washed with water and saturated brine, dried over sodium sulfate, filtered and concentrated. The residue was purified with silica gel column chromatography (silica gel 60 mL, chloroform/methanol=1:0→10:1→5:1) to give allyl {[(2R,3S)-3-((1R)-1-{[tert-butyl(dimethyl)silyl]oxy}ethyl)-2-[2-(3-chloro-4-{2-[(1H-imidazol-5-ylmethyl)amino]-2-oxoethyl}phenyl)-2-oxoethyl]-4-oxoazetidin-1-yl]}(triphenylphosphoranilidene)acetate (1.3 g, yield, 84%) as a pale yellow amorphous. This product was subjected to next reaction without further purification. Allyl {[(2R,3S)-3-((1R)-1-{[tert-butyl(dimethyl)silyl]oxy}ethyl)-2-[2-(3-chloro-4-{2-[(1H-imidazol-5-ylmethyl)amino]-2-oxoethyl}phenyl)-2-oxoethyl]-4-oxoazetidin-1-yl]}(triphenylphosphoranilidene)acetate (1.29 g) and 4-dimethylaminopyridine (18 mg, 0.14 mmol) were dissolved in pyridine (13 ml), and thereto was added at 0° C. allyl chloroformate (0.2 ml, 1.9 mmol), followed by stirring for 20 minutes. To the reaction solution was added ethyl acetate. The mixture was washed with saturated bicarbonate solution and saturated brine, dried over sodium sulfate, filtered, and concentrated to give an yellow oil (1.35 g). This product was dissolved in a cooled 70% TFA solution (10 ml), and the mixture was stirred for 5 minutes. After removal of the ice bath, the mixture was stirred for 30 minutes, and again cooled in the ice bath. To the reaction solution was added saturated biscarbonate solution to adjust pH of the medium to 8.0 and then thereto was added ethyl acetate. The mixture was washed with saturated brine, dried over sodium sulfate, filtered, and concentrated to give a pale yellow amorphous (1.2 g). This product was subjected to next reaction without further purification. Thus obtained pale yellow amorphous (1.2 g) and triethylamine (1.56 ml, 11.2 mmol) were dissolved in THF (24 ml), and to the solution was added at 0° C. chlorotrimethylsilane (1.52 ml, 8.4 mmol), followed by stirring for 5 minutes. After removal of the ice bath, the mixture was stirred at room temperature for 25 minutes and again cooled in an ice bath. To the reaction mixture were added ethyl acetate and saturated bicarbonate solution. The organic layer was washed with saturated brine, dried over sodium sulfate, filtered and concentrated to give allyl 5-{[({4-[((2R,3S)-1-[2-(allyloxy)-2-oxo-1-(triphenylphosphoranilidene)ethyl]-4-oxo-3-{(1R)-1-[(trimethylsilyl)oxy]ethyl}azetidin-2-yl)acetyl]-2-chlorophenyl}acetyl)amino]methyl}-1H-imidazole-1-carboxylate (1.27 g, yield 83%) as an yellow oil.

LC/MS (EI) 919 (M+1)

Step c)

Allyl 5-{[({4-[((2R,3S)-1-[2-(allyloxy)-2-oxo-1-(triphenylphosphoranilidene)ethyl]-4-oxo-3-{(1R)-1-[(trimethylsilyl)oxy]ethyl}azetidin-2-yl)acetyl]-2-chlorophenyl}acetyl)amino]methyl}-1H-imidazole-1-carboxylate (1.27 g) prepared by step c) was dissolved in toluene (26 ml), and thereto were added N,O-bistrimethylsilylacetamide (0.7 ml) and 2,6-di-tert-butyl p-cresol (20 mg), followed by refluxing at 100° C. for 2 hours. After cooling, the reaction solution was concentrated, and the residue was purified with column chromatography (silica gel 150 mL, chloroform:methanol=100:0~100:3) to give allyl (5R,6S)-3-(4-{2-[({1-[(allyloxy)carbonyl]-1H-imidazol-5-yl}methyl)amino]-2-oxoethyl}-3-chlorophenyl)-7-oxo-6-{(1R)-1-[(trimethylsilyl)oxy]ethyl}-1-azabicyclo[3.2.0]hept-2-ene-2-carboxylate (0.78 g, yield 89%) as a yellow oil.

$^1$H NMR (400 MHz, CDCl$_3$) δ 0.15 (s, 9 H), 1.29 (d, 3 H, J=6.4 Hz), 3.10-3.30 (m, 3 H), 3.69 (s, 2 H), 4.15-4.21 (m, 2 H), 4.35 (d, 2 H, J=5.6 Hz), 4.58-4.65 (m, 2 H), 4.85-4.87 (m, 2 H), 5.18-5.46 (m, 4 H), 5.81-6.05 (m, 2 H), 6.12-6.20 (m, 1 H), 7.30 (s, 1 H), 7.36-7.70 (m, 3 H), 7.45-7.60 (m, 2 H), 8.05 (s, 1 H).

Step d)

Allyl (5R,6S)-3-(4-{2-[({1-[(allyloxy)carbonyl]-1H-imidazol-5-yl}methyl)amino]-2-oxoethyl}-3-chlorophenyl)-7-oxo-6-{(1R)-1-[(trimethylsilyl)oxy]ethyl}-1-azabicyclo[3.2.0]hept-2-ene-2-carboxylate (0.78 g, 1.22 mmol) prepared by step c) was dissolved in THF (23 ml) and water (11 ml), and the solution was cooled in a water bath. Thereto was gradually dropped using a pH meter, 0.1N hydrochloric acid to adjust pH to 3.0. Fifteen minutes later, pH of the solution was adjusted 6.8 by gradually dropping saturated bicarbonate solution thereto, and then saturated brine (50 ml) was added. The solution was extracted with ethyl acetate. The organic layers were combined, dried over sodium sulfate, filtered, and concentrated to give allyl (5R,6S)-3-(4-{2-[({1-[(allyloxy)carbonyl]-1H-imidazol-5-yl}methyl)amino]-2-oxoethyl}-3-chlorophenyl)-6-[(1R)-1-hydroxyethyl]-7-oxo-1-azabicyclo[3.2.0]hept-2-ene-2-carboxylate (0.54 g, yield 78%) as a pale yellow amorphous.

$^1$H NMR (400 MHz, CDCl$_3$) δ 1.37 (d, 3 H, J=6.0 Hz), 1.61 (br-s, 1 H), 3.13-3.35 (m, 3 H), 3.69 (s, 2 H), 4.20-4.32 (m, 2 H), 4.35 (d, 2 H, J=6.0 Hz), 4.57-4.75 (m, 2 H), 4.86 (d, 2 H, J=4.8 Hz), 5.20-5.50 (m, 4 H), 5.80-6.02 (m, 2 H), 6.10-6.20 (m, 1 H), 7.31 (s, 1 H), 7.37-7.40 (m, 2 H), 7.45-7.60 (m, 2 H), 8.06 (s, 1 H).

Example 1

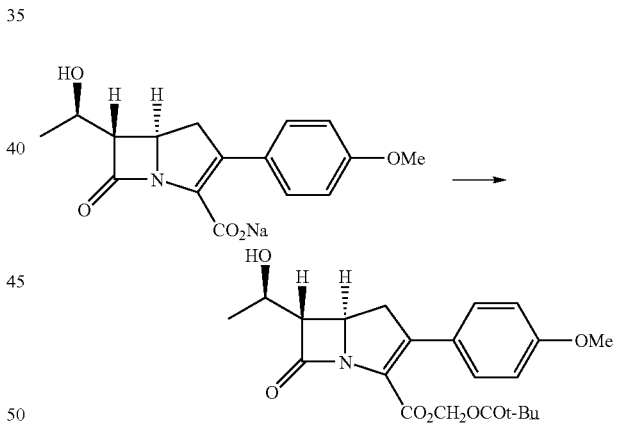

Sodium (5R,6S)-6-[(1R)-1-hydroxyethyl]-3-(4-methoxyphenyl)-7-oxo-1-azabicyclo[3.2.0]hept-2-ene-2-carboxylate (0.17 g) was dissolved in dry DMF (1.7 ml) and the solution was ice-cooled. Thereto was gradually dropped pivaloyloxymethyl iodide (0.12 g) in dry DMF (1.2 ml) and the mixture was stirred. Thirty minutes later, ethyl acetate was added thereto and the mixture was washed with bicarbonate solution, water and brine, successively. The organic layer was dried over sodium sulfate, concentrated and the residue was purified with silica gel column chromatography (hexane:ethyl acetate=1:2~ethyl acetate only) to give [(2,2-dimethylpropanoyl)oxymethyl(5R,6S)-6-[(1R)-1-hydroxyethyl]-3-(4-methoxyphenyl)-7-oxo-1-azabicyclo[3.2.0]hept-2-ene-2-carboxylate (0.15 g, yield 70%).

$^1$H NMR (400 MHz, CDCl$_3$) δ 1.19 (s, 9H), 1.37 (d, 3H, J=6.4 Hz), 1.71 (d, 1H, J=5.2 Hz), 3.18-3.32 (m, 3H), 3.82 (s,

3H), 4.23-4.31 (m, 2H), 5.79 (d, 1H, J=5.2 Hz), 5.89 (d, 1H, J=5.2 Hz), 6.87 (d, 2H, J=12.0 Hz), 7.36 (d, 2H, J=12.0 Hz)

Example 2

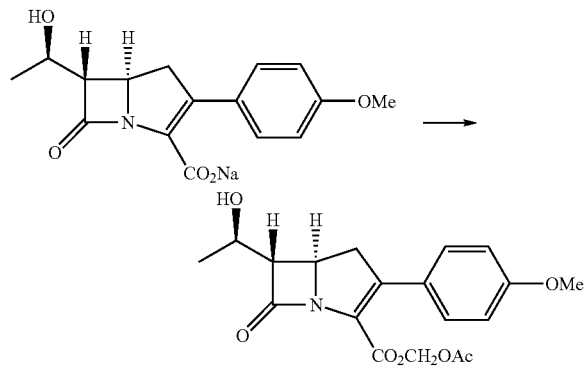

Sodium (5R,6S)-6-[(1R)-1-hydroxyethyl]-3-(4-methoxyphenyl)-7-oxo-1-azabicyclo[3.2.0]hept-2-ene-2-carboxylate (0.18 g) in dry DMF (3.6 ml) was ice-cooled, and thereto was added triethylbenzylammoniun chloride (0.11 g). To the mixture was gradually dropped bromomethylacetate (0.16 ml) and the mixture was gradually allowed to room temperature and stirred. Forty minutes later, thereto was added ethyl acetate, and the mixture was washed with bicarbonate solution, water and brine, successively. The organic layer was dried over sodium sulfate, concentrated and the residue was purified with silica gel column chromatography (ethyl acetate only) to give (acetyloxy)methyl (5R,6S)-6-[(1R)-1-hydroxyethyl]-3-(4-methoxyphenyl)-7-oxo-1-azabicyclo[3.2.0]hept-2-ene-2-carboxylate (0.15 g, yield 48%).

$^1$H NMR (400 MHz, CDCl$_3$) δ 1.38 (d, 3H, J=6.0 Hz), 1.71 (d, 1H, J=4.8 Hz), 2.09 (s, 3H), 3.20-3.30 (m, 3H), 3.83 (s, 3H), 4.22-4.31 (m, 2H), 5.80 (d, 1H, J=4.8 Hz), 5.87 (d, 1H, J=4.8 Hz), 6.88 (d, 2H, J=7.2 Hz), 7.39 (d, 2H, J=7.2 Hz)

Example 3

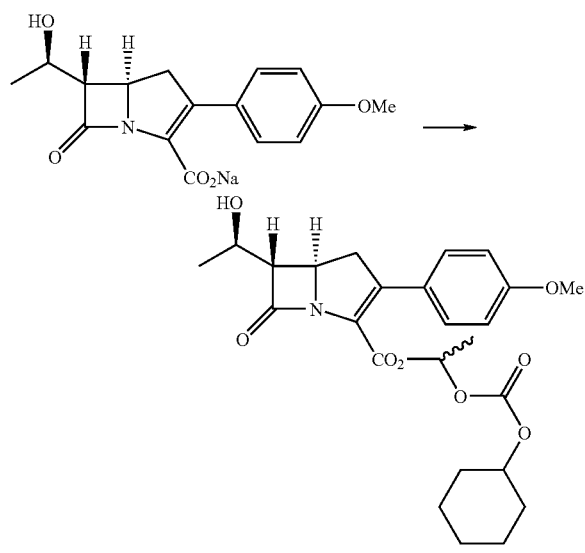

Sodium (5R,6S)-6-[(1R)-1-hydroxyethyl]-3-(4-methoxyphenyl)-7-oxo-1-azabicyclo[3.2.0]hept-2-ene-2-carboxylate (0.43 g) was dissolved in dry DMF (4.3 ml) and thereto was added triethylbenzylammonium chloride (0.25 g). Thereto was dropped 1-chloroethylcyclohexylcarbonate (0.62 g) and the mixture was stirred under heating to 50° C. One hour later, the mixture was cooled to room temperature and thereto was added ethyl acetate. The mixture was washed with bicarbonate solution, water and brine, successively. The organic layer was dried over sodium sulfate, concentrated, and the residue was purified with silica gel column chromatography (hexane:ethyl acetate=1:2→1:3→ethyl acetate only) to give 1-{[(cyclohexyloxy)carbonyl]oxy}ethyl(5R,6S)-6-[(1R)-1-hydroxyethyl]-3-(4-methoxyphenyl)-7-oxo-1-azabicyclo[3.2.0]hept-2-ene-2-carboxylate (0.12 g, yield 20%).

$^1$H NMR (400 MHz, CDCl$_3$) δ 1.13-1.99 (m, 17H), 3.17-3.31 (m, 3H), 3.82 (s, 3H), 4.19-4.26 (m, 2H), 4.60-4.65 (m, 1H), 6.83-6.90 (m, 3H), 7.39 (t, 2H, J=8.0 Hz)

Example 4

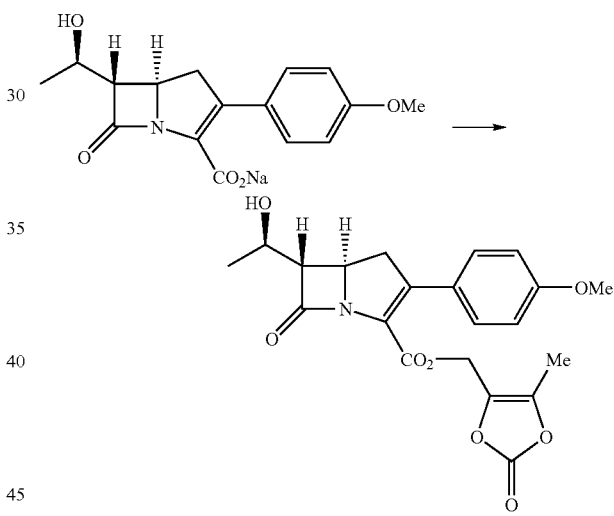

Sodium (5R,6S)-6-[(1R)-1-hydroxyethyl]-3-(4-methoxyphenyl)-7-oxo-1-azabicyclo[3.2.0]hept-2-ene-2-carboxylate (0.15 g) in dry DMF (2.0 ml) was ice-cooled. After 4-bromomethyl-5-methyl-1,3-dioxol-2-one (115 mg) was dropped thereto, the mixture was stirred for 30 minutes. After removal of the bath the mixture was further stirred for 30 minutes. Thereto was ethyl acetate, and the mixture was washed with bicarbonate solution, water and brine, successively. The organic layer was dried over sodium sulfate, concentrated and the residue was purified with silica gel column chromatography (ethyl acetate only) to give (5-methyl-2-oxo-1,3-dioxol-4-yl)methyl (5R,6S)-6-[(1R)-1-hydroxyethyl]-3-(4-methoxyphenyl)-7-oxo-1-azabicyclo[3.2.0]hept-2-ene-2-carboxylate (0.11 g, yield 60%).

$^1$HNMR (400MHz, CDCl$_3$) δ 1.37 (d, 3H, J=6.0 Hz), 1.73 (d, 1H, J=4.8 Hz), 3.18-3.32 (m, 3H), 4.24-4.29 (m, 2H), 4.90 (dd, 1H, J=39.6 Hz, 14 Hz), 5.90 (d, 1H, J=6.4 Hz), 6.88 (dd, 2H, J=9.2 Hz, 2.8 Hz), 7.30 (dd, 2H, J=9.2 Hz, 2.8 Hz)

Example 5

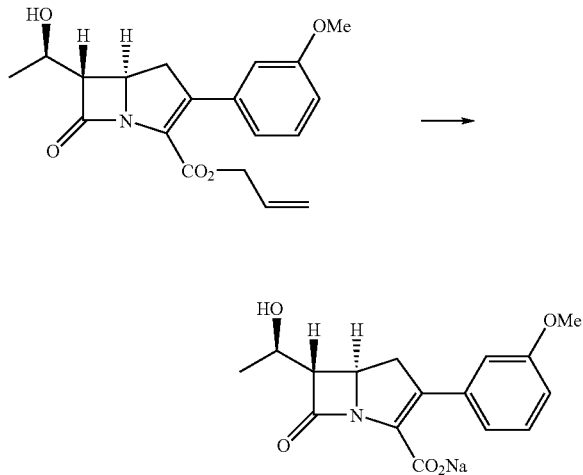

Allyl (5R,6S)-6-[(1R)-1-hydroxyethyl]-3-(3-methoxyphenyl)-7-oxo-1-azabicyclo[3.2.0]hept-2-ene-2-carboxylate (1.37 g, 3.99 mmol) prepared by Reference Example 3, triphenylphosphine (52 mg), and tetrakis(triphenylphosphine)palladium(0) (0.23 g, 0.2 mmol) were dissolved in THF (20 ml), and thereto was added at 0° C. sodium 2-ethylhexanoate in ethyl acetate (0.5 M, 8.0 ml, 4.0 mmol), followed by stirring for 1 hour. Thereto was added hexane (30 ml) and the resulting white crystals were filtered under a nitrogen atmosphere, washed with hexane, dried at room temperature in vacuo to give a crude product. The product was dissolved in a small amount of ice-water, and purified with C18 reverse column chromatography (filler: Akosil 40C18 (Wako Pure Chemical Ind.); mobile phase; 0~5%THF/ice-cooled ion-exchange water). The fractions containing the object compound were combined and THF therein was removed at room temperature in vacuo under stirring for 1 hour. The residue was lyophilized to give sodium (5R,6S)-6-[(1R)-1-hydroxyethyl]-3-(3-methoxyphenyl)-7-oxo-1-azabicyclo[3.2.0]hept-2-ene-2-carboxylate (297 mg, yield 23%).

LCMS (EI) 304 (M+1).

$^1$H NMR (400 MHz, DMSO-d6) δ 1.09 (d, 3 H, J=6.3 Hz), 2.82 (dd, 1 H, J=15.6 Hz, 9.9 Hz), 3.01 (dd, 1 H, J=15.6 Hz, 8.5 Hz), 3.08 (dd, 1 H, J=6.5 Hz, 2.8 Hz), 3.63 (s, 3 H), 3.80-3.88 (m, 1 H), 3.92-3.97 (m, 1 H), 4.94 (d, 1 H, J=5.0 Hz), 6.62 (ddd, 1 H, J=8.0 Hz, 2.5 Hz, 0.7 Hz), 6.94-6.96 (m, 1 H), 7.06 (t, 1 H, J=8.0 Hz), 7.09-7.10 (m, 1 H).

Example 6

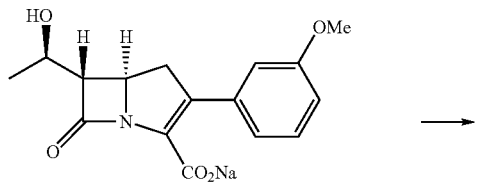

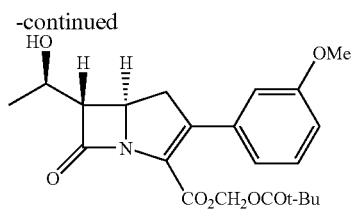

Sodium (5R,6S)-6-[(1R)-1-hydroxyethyl]-3-(3-methoxyphenyl)-7-oxo-1-azabicyclo[3.2.0]hept-2-ene-2-carboxylate (100 mg) prepared by Example 5, was treated in the same method as Example 1 to give (2,2-dimethylpropanoyl)oxy]methyl (5R,6S)-6-[(1R)-1-hydroxyethyl]-3-(3-methoxyphenyl)-7-oxo-1-azabicyclo[3.2.0]hept-2-ene-2-carboxylate (114 mg, yield 88%).

LCMS (EI) 418 (M+1).

$^1$H NMR (400 MHz, CDCl$_3$) δ 1.18 (s, 9 H), 1.36 (d, 3 H, J=6.3 Hz), 3.17-3.55 (m, 3 H), 3.80 (s, 3 H), 4.18-4.32 (m, 2 H), 5.76 (d, 1 H, J=5.5 Hz), 5.85 (d, 1 H, J=5.5 Hz), 6.87-6.92 (m, 3 H), 7.23-7.28 (m, 1 H).

Example 7

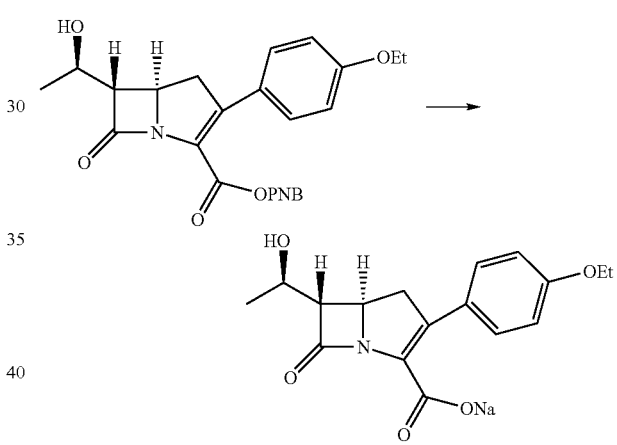

4-Nitrobenzyl (5R,6S)-3-(4-ethoxyphenyl)-6-[(1R)-1-hydroxyethyl]-7-oxo-1-azabicyclo[3.2.0]hept-2-ene-2-carboxylate (1.39 g) prepared in accordance to the method described in Tetrahedron Letters, 34, 3211-3214 (1993)] was dissolved in THF (28 mL), and thereto were added under ice cooling sodium hydrogencarbonate in ion-exchange water (28 mL), and 10% palladium-carbon [50% water] (0.14 g). Then the atmosphere was changed with a hydrogen gas, and the mixture was stirred at the same temperature for 3 hours. After filtration of the insoluble materials with Celite, to the filtrate was added chloroform (80 mL). The organic layer was separated, and extracted with ion-exchange water (20 mL). The organic solvent in the aqueous solution separated and extracted was removed over one hour period in vacuo, purified with C18 reverse column chromatography (Wakosil C18 reverse column, mobile phase; ion-exchange water/THF) and lyophilized to give sodium (5R,6S)-3-(4-ethoxyphenyl)-6-[(1R)-1-hydroxyethyl]-7-oxo-1-azabicyclo[3.2.0]hept-2-ene-2-carboxylate (0.44 g, yield 42%).

$^1$H NMR (400 MHz, D$_2$O) δ 1.20 (d, 3H, J=6.4 Hz), 1.26 (t, 3H, J=6.8 Hz), 2.95 (dd, 1H, J=17.2 Hz, 10.0 Hz), 3.25 (dd1H, J=17.2 Hz, 8.4 Hz), 3.35-3.38 (m, 1H), 4.02 (q, 2H, J=6.8 Hz), 4.12-4.17 (m, 2H), 6.83 (d, J=8.8 Hz, 2H), 7.16 (d, J=8.8 Hz, 2H),

Example 8

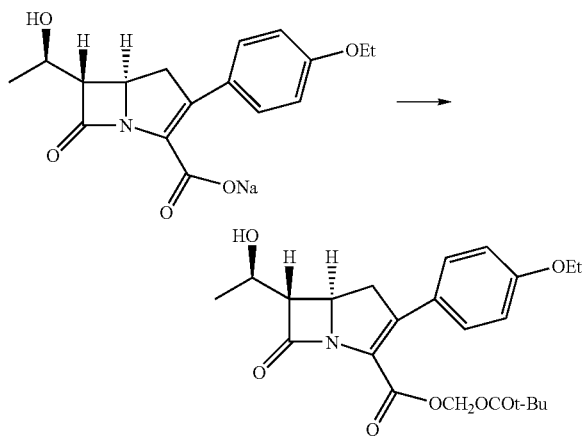

Sodium (5R,6S)-3-(4-ethoxyphenyl)-6-[(1R)-1-hydroxyethyl]-7-oxo-1-azabicyclo[3.2.0]hept-2-ene-2-carboxylate (0.2 g) prepared by Example 8 in dry DMF was ice-cooled, and thereto was at the same temperature added pivaloyloxymethyl iodide (0.14 g), followed by stirring for 90 minutes. To the reaction mixture were added ethyl acetate and ice water, and the mixture was separated by a separatory funnel. The organic layer was washed with cooled brine (4 times), dried over anhydrous sodium sulfate, and the solvent was removed in vacuo. The residue was purified by silica gel column chromatography (ethyl acetate only) to give [(2,2-dimethylpropanoyl)oxymethyl (5R,6S)-3-(4-ethoxyphenyl)-6-[(1R)-1-hydroxyethyl]-7-oxo-1-azabicyclo[3.2.0]hept-2-ene-2-carboxylate (0.15 g, yield 60%).

$^1$H NMR (400 MHz, CDCl$_3$) δ 1.19 (s, 9H), 1.36 (d, 3H, J=6.4 Hz), 1.41 (t, 3H, J=6.8 Hz), 1.81 (d, 1H, J=4.8 Hz), 3.18-3.31 (m, 3H), 4.05 (q, 2H, J=6.4 Hz), 4.23-4.28 (m, 2H), 5.79 (d, 1H, J=5.4 Hz), 5.88 (d, 1H, J=5.4 Hz), 6.81 (d, J=8.4 Hz, 2H), 7.35 (d, J=8.4 Hz, 2H)

The following compounds in tables below were prepared in the same 5 manners as in Examples 1 to 8.

TABLE 21

|  | Example 9 | Example 10 | Example 11 |
|---|---|---|---|
| R$^a$ | —H | —H | —H |
| R$^b$ | —OEt | —OEt | —H |
| R$^c$ | —H | —H | —OCF$_3$ |
| R | —Na | —CH$_2$OCOt-Bu | —Na |
| Physical data | $^1$H NMR(400MHz, D$_2$O)δ1.25(d, 3H, J=6.4Hz), 1.30(t, 3H, J=7.0Hz), 3.02 (dd, 1H, J=16.9Hz, 9.8Hz), 3.35(dd, 1H, J=16.9Hz, 8.4Hz), 3.42-3.48(m, 1H), 4.05(q, 2H, J=7.0Hz), 4.16-4.28 (m, 2H), 6.83-6.95 (m, 3H), 7.21-7.29 (m, 1H) | $^1$H NMR(400MHz, CDCl$_3$)δ1.18 (s, 9H), 1.37(d, 3H, J=6.3Hz), 1.41(t, 3H, J=7.0Hz), 1.73(d, 1H, J=4.9Hz), 3.17-3.30(m, 3H), 4.02(q, 2H, J=7.0Hz), 4.24-4.31(m, 2H), 5.78(d, 1H, J=5.5Hz), 5.86 (d, 1H, J=5.5Hz), 6.83-6.92(m, 3H), 6.99-7.26(m, 1H) | $^1$H NMR(400MHz, D$_2$O)δ1.19(dd, 3H, J=4.0Hz, 6.4Hz), 2.97 (dd, 1H, J=16.8Hz, 10Hz), 3.32(dd, 1H, J=16.8Hz, 8.4Hz), 3.39-3.41(m, 1H), 4.13-4.22(m, 2H), 7.18(d, J=8.4Hz, 2H), 7.31(d, J=8.4Hz, 2H) |

TABLE 22

|  | Example 12 | Example 13 | Example 14 |
|---|---|---|---|
| R$^a$ | —H | —H | —H |
| R$^b$ | —H | —H | —H |
| R$^c$ | —OCF$_3$ | —CH$_3$ | —CH$_3$ |

TABLE 22-continued

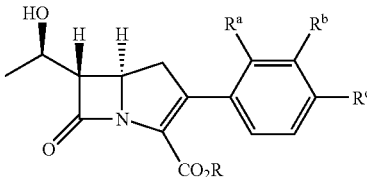

|  | Example 12 | Example 13 | Example 14 |
|---|---|---|---|
| R | —CH$_2$OCOt-Bu | —Na | —CH$_2$OCOt-Bu |
| Physical data | $^1$H NMR(400MHz, CDCl$_3$)δ1.18(s, 9H), 1.37(d, 3H, J=6.4Hz), 1.75(d, 1H, J=4.8Hz), 3.17-3.34(m, 3H), 4.26-4.33(m, 2H), 5.77(d, 1H, J=5.6Hz), 5.87(d, 1H, J=5.6Hz), 7.19(d, J=8.0Hz, 2H), 7.39(d, J=8.0Hz, 2H) | $^1$H NMR(DMSO-d$_6$, 400MHz)δ1.09(d, 3 H, J=6.3Hz), 2.18(s, 3H), 2.79(dd, 1H, J=9.8Hz, 15.7Hz), 2.99(dd, 1H, J=8.6 Hz, 15.7Hz), 3.05 (dd, 1H, J=2.8Hz, 6.6Hz), 3.80-3.88 (m, 1H), 3.90-3.97 (m, 1H), 4.93(d, 1H, J=5.0Hz), 6.95(br. d, 2H, J=8.0Hz), 7.29-7.31(m, 2H). LCMS(EI)288 (M+1+). | $^1$H NMR(CDCl$_3$, 400 MHz)δ1.19(s, 9H), 1.37(d, 3H, J=6.3 Hz), 1.90(br. d, 1H, J=4.0Hz), 2.36(s, 3 H), 3.21(dd, 1H, J=9.8Hz, 18.3Hz), 3.24(dd, 1H, J=2.8 Hz, 6.8Hz), 3.31(dd, 1H, J=8.9Hz, 18.3 Hz), 4.21-4.31(m, 2 H), 5.77(d, 1H, J=5.5Hz), 5.87(d, 1 H, J=5.5Hz), 7.16 (br. d, 2H, J=8.0Hz), 7.26(br. d, 2H, J=8.2 Hz). LCMS(EI)402 (M+1+). |

TABLE 23

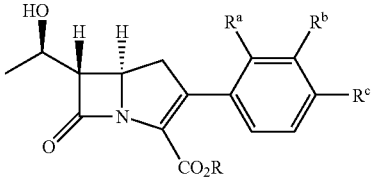

|  | Example 15 | Example 16 | Example 17 |
|---|---|---|---|
| R$^a$ | —H | —H | —H |
| R$^b$ | —CH$_3$ | —CH$_3$ | —H |
| R$^c$ | —H | —H | —CH$_2$OCH$_3$ |
| R | —Na | —CH$_2$OCOt-Bu | —Na |
| Physical data | $^1$H NMR(D$_2$O, 300 MHz)δ1.15(d, 3H, J= 6.4Hz), 2.16(s, 3 H), 2.91(dd, 1H, J= 9.7Hz, 16.8Hz), 3.27 (dd, 1H, J=8.4Hz, 16.8Hz), 3.35(dd, 1 H, J=2.8Hz, 6.0Hz), 4.06-4.18(m, 2H), 6.98-7.15(m, 4 H). IR(ATR)1743, 1585, 1389, 1308, 1250, 1223, 1134, 1001, 947, 783, 694 cm$^{-1}$. LCMS(EI)288(M+1+). | $^1$H NMR(CDCl$_3$, 300 MHz)δ1.18(s, 9H), 1.37(d, 3H, J=6.2 Hz), 2.35(s, 3H), 3.15-3.36(m, 3H), 4.23-4.33(m, 2H), 5.77(d, J=5.5Hz), 5.85(d, J=5.5Hz), 7.12-7.24(m, 4H). IR(ATR)2974, 1751, 1481, 1458, 1340, 1267, 1182, 1120, 1095, 1022, 980, 785, 731, 696 cm$^{-1}$. LCMS(EI)402(M+1+). | $^1$H NMR(DMSO-d$_6$, 400MHz)δ1.09(d, 3 H, J=6.3Hz), 2.81 (dd, 1H, J=9.8Hz, 15.7Hz), 3.03(dd, 1 H, J=8.5Hz, 15.7 Hz), 3.08(dd, 1H, J= 2.8Hz, 6.6Hz), 3.18 (s, 3H), 3.81-3.88(m, 1H), 3.91-3.97(m, 1 H), 4.28(s, 2H), 4.94 (d, 1H, J=4.9Hz), 7.09(br. d, 2H, J= 8.3Hz), 7.38(br. d, 2 H, J=8.3Hz). IR(ATR)3491, 3342, 2980, 2922, 2891, 1780, 1742, 1585, 1516, 1379, 1306, 1248, 1213, 1159, 1138, 1099, 1068, 962, 933, 847, 816, 783, 708, 677, 638 cm$^{-1}$. LCMS(EI)318(M+1+). |

TABLE 24

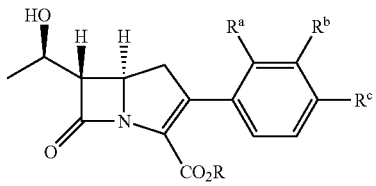

| | Example 18 | Example 19 | Example 20 |
|---|---|---|---|
| $R^a$ | —H | —H | —H |
| $R^b$ | —H | —H | —H |
| $R^c$ | —CH$_2$OCH$_3$ | —Cl | —Cl |
| R | —CH$_2$OCOt-Bu | —Na | —CH$_2$OCOt-Bu |
| Physical data | $^1$H NMR(CDCl$_3$, 400 MHz)δ1.19(s, 9H), 1.37(d, 3H, J=6.3 Hz), 1.83(d, 1H, J=4.8Hz), 3.22(dd, 1H, J=9.9Hz, 18.3Hz), 3.26(dd, 1H, J=2.7 Hz, 6.9Hz), 3.33(dd, 1H, J=8.9Hz, 18.3 Hz), 4.23-4.33(m, 2H), 5.77(d, 1H, J=5.5Hz), 5.87(d, 1H, J=5.5Hz), 7.31-7.38(m, 4H). LCMS(EI)432(M+1+). | $^1$H NMR(400MHz, D$_2$O)δ1.17(d, 3H, J=6.4Hz), 2.94(dd, 1H, J=16.9Hz, 9.8Hz), 3.30(dd, 1H, J=16.9Hz, 8.4Hz), 3.35-3.41(m,1H), 4.08-4.20(m, 2H), 7.16-7.21(m,2H), 7.21-7.27(m,2H) | $^1$H NMR(400MHz, CDCl$_3$)δ1.18(s, 9H), 1.37(d, 3H, J=6.3Hz), 1.74(d, 1H, J=4.8Hz), 3.14-3.35(m, 3H), 4.19-4.34(m, 2H), 5.76(d, 1H, J=5.5Hz), 5.87 (d, 1H, J=5.5Hz), 7.22-7.35(m, 4H) |

TABLE 25

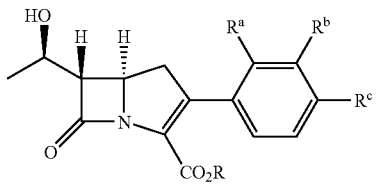

| | Example 21 | Example 22 | Example 23 |
|---|---|---|---|
| $R^a$ | —H | —H | —H |
| $R^b$ | —H | —H | —F |
| $R^c$ | —F | —F | —H |
| R | —Na | —CH$_2$OCOt-Bu | —Na |
| Physical data | $^1$H NMR(400MHz, D$_2$O)δ1.03(d, 3H, J=6.4Hz), 2.80(dd, 1H, J=16.8Hz, 8.4Hz), 3.14(dd, 1H, J=16.8Hz, 8.4Hz), 3.21-3.23(m, 1H), 3.96-4.05(m, 2H), 6.79-6.85(m, 2H), 7.06-7.10(m, 2H) | $^1$H NMR(400MHz, CDCl$_3$)δ1.18(s, 9H), 1.37(d, 3H, J=6.4Hz), 3.17-3.33(m, 3H), 4.25-4.32(m, 2H), 5.76(d, 1H, J=5.4Hz), 5.87(d, 1H, J=5.4Hz), 6.99-7.06(m, 2H), 7.33-7.37(m, 2H) | $^1$H NMR(400MHz, D$_2$O)δ1.18(d, 3H, J=6.4Hz), 2.96(dd, 1H, J=16.8Hz, 10Hz), 3.24(dd, 1H, J=16.8Hz, 8.4Hz), 3.39-3.40(m, 1H), 4.11-4.20(m, 2H), 6.92-7.04(m, 3H), 7.20-7.24(m, 1H) |

TABLE 26

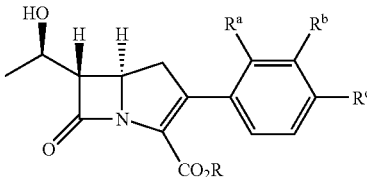

|  | Example 24 | Example 25 | Example 26 |
|---|---|---|---|
| $R^a$ | —H | —F | —F |
| $R^b$ | —F | —H | —H |
| $R^c$ | —H | —H | —H |
| R | —CH$_2$OCOt-Bu | —Na | —CH$_2$OCOt-Bu |
| Physical data | $^1$H NMR(400MHz, CDCl$_3$)δ1.18(s, 9H), 1.37(d, 3H, J=6.4Hz), 1.80(d, 1H, J=4.4Hz), 3.16-3.34(m, 3H), 4.24-4.33(m, 2H), 5.76(d, 1H, J=5.4Hz), 5.86(d, 1H, J=5.4Hz), 7.02-7.12(m, 3H), 7.30-7.32(m,1H) | $^1$H NMR(400MHz, D$_2$O)δ1.17(d, 3H, J=6.4Hz), 2.85(dd, 1H, J=16.4Hz, 9.6Hz), 3.29(dd, 1H, J=16.4Hz, 8.8Hz), 3.35-3.37(m, 1H), 4.08-4.19(m, 2H), 6.97-7.06(m, 2H), 7.14-7.19(m, 2H) | $^1$H NMR(400MHz, CDCl$_3$)δ1.17(s, 9H), 1.37(d, 3H, J=6.4Hz), 1.74(d, 1H, J=4.4Hz), 3.14-3.36(m, 3H), 4.27-4.37(m, 2H), 5.72(d, 1H, J=5.4Hz), 5.81(d, 1H, J=5.4Hz), 7.04-7.34(m, 4H) |

TABLE 27

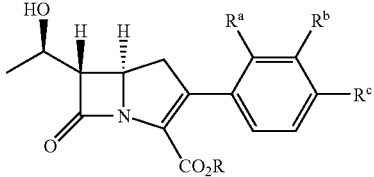

|  | Example 27 | Example 28 | Example 29 |
|---|---|---|---|
| $R^a$ | —H | —H | —H |
| $R^b$ | —H | —H | —H |
| $R^c$ | —CN | —CN | —SO$_2$NHMe |
| R | —Na | —CH$_2$OCOt-Bu | —Na |
| Physical data | $^1$H NMR(400MHz, D$_2$O)δ1.16(d, 3H, J=6.4Hz), 2.97(dd, 1H, J=16.9Hz, 9.9Hz), 3.31(dd, 1H, J=16.9Hz, 8.5Hz), 3.36-3.43 (m, 1H), 4.06-4.14 (m, 1H), 4.14-4.22 (m, 1H), 7.25-7.36 (m, 2H), 7.52-7.80 (m, 2H) | $^1$H NMR(400MHz, CDCl$_3$)δ1.18(s, 9H), 1.37(d, 3H, J=6.3Hz), 1.78(br s, 1H), 3.15-3.40(m, 3H), 4.25-4.40(m, 2H), 5.76(d, 1H, J=5.5Hz), 5.86(d, 1H, J=5.5Hz), 7.40-7.46(m, 2H), 7.60-7.68(m, 2H) | $^1$H NMR(400MHz, D$_2$O) δ1.26(d, 3H, J=6.4Hz), 2.50(s, 3H), 3.08(dd, 1H, J=16.9Hz, 9.9Hz), 3.43(dd, 1H J=16.9Hz, 8.5Hz), 3.47-3.53(m, 1H), 4.17-4.24(m, 1H), 4.24-4.36(m, 1H), 7.50 (d, 2H, J=8.6Hz), 7.75 (d, 2H, zJ=8.6Hz) |

TABLE 28

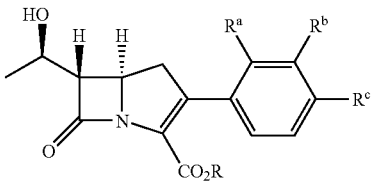

|  | Example 30 | Example 31 |
|---|---|---|
| $R^a$ | —H | —H |
| $R^b$ | —H | —H |

TABLE 28-continued

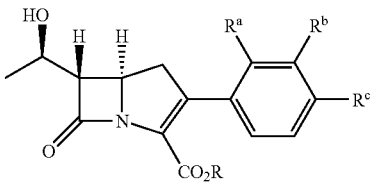

| | Example 30 | Example 31 |
|---|---|---|
| $R^c$ | —OCH$_2$CH$_2$OCH$_3$ | —OCH$_2$CH$_2$OCH$_3$ |
| R | —Na | —CH$_2$OCOt-Bu |
| Physical data | $^1$H NMR(D$_2$O, 300MHz)δ1.16(d, 3H, J=6.4Hz), 2.91(dd, 1H, J=9.5Hz, 17.0Hz), 3.26(dd, 1H, J=8.8Hz, 16.9Hz), 3.29(s, 3H), 3.33(dd, 1H, J=2.6Hz, 6.0Hz), 3.66-3.69(m, 2H), 4.06-4.17(m, 4H), 6.81-6.91(m, 2H), 7.17-7.22(m, 2H). IR(ATR)1781, 1585, 1511, 1456, 1383, 1288, 1250, 1219, 1192, 1138, 1124, 1068, 1035, 924, 860, 827, 802, 777, 710 cm$^{-1}$. LCMS(EI)348(M+1+). | $^1$H NMR(CDCl$_3$, 300MHz)δ1.20 (s, 9H), 1.37(d, 3H, J=6.4Hz), 3.20-3.28(m, 3H), 3.45(s, 3H), 3.74-3.77(m, 2H), 4.12-4.16(m, 2H), 4.22-4.30(m, 2H), 5.79(d, 1H, J=5.5Hz), 5.88(d, 1H, J=5.5 Hz), 6.87-6.92(m, 2H), 7.33-7.39 (m, 2H). IR(ATR)2974, 1774, 1751, 1604, 1510, 1456, 1340, 1248, 1182, 1124, 1093, 1022, 978, 829, 767 cm$^{-1}$. LCMS(EI)462(M+1+). |

Example 32 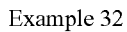 Example 33 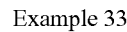

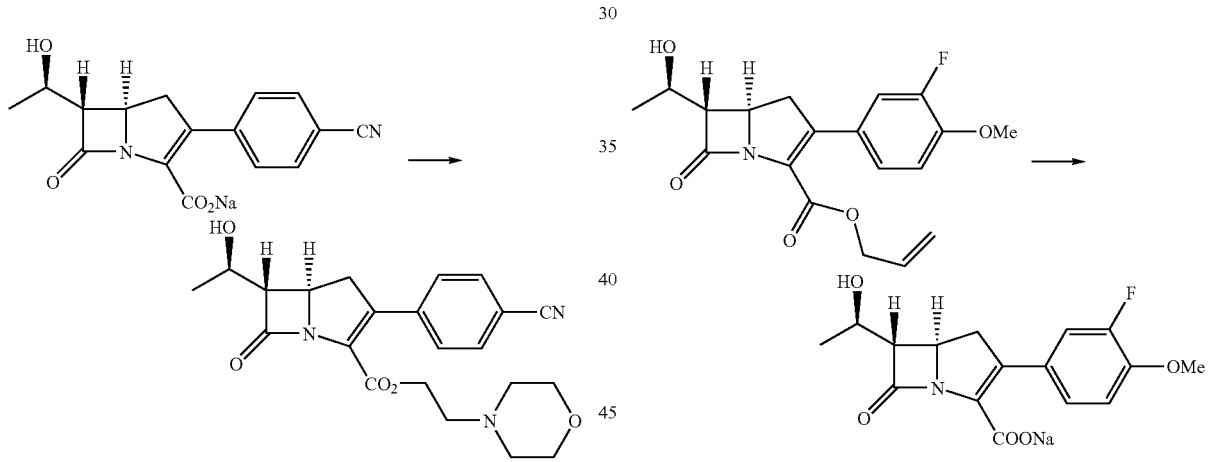

Sodium (5R,6S)-3-(4-cyanophenyl)-6-[(1R)-1-hydroxyethyl]-7-oxo-1-azabicyclo[3.2.0]hept-2-ene-2-carboxylate (0.2 g) in dry DMF (4.0 ml) was ice-cooled. Thereto ware added tetrabutylammonium iodide (0.53 g), and 4-(2-chloroethyl)-morpholine (1M toluene, 8 mL), and the mixture was stirred. Thirty minutes later, after removal of the bath the mixture was stirred for 48 hours and thereto was added ethyl acetate. The mixture was washed succesively with aqueous phosphate buffer (pH 6.86), water and brine. The organic layer was dried over sodium sulfate, concentrated, and the residue was purified with silica gel column chromatography (chloroform:methanol=1:0→10:1) to give 2-morpholin-4-yl-ethyl(5R,6S)-3-(4-cyanophenyl)-6-[(1R)-1-hydroxyethyl]-7-oxo-1-azabicyclo[3.2.0]hept-2-ene-2-carboxylate (0.10 g, yield 33%).

$^1$HNMR (400 MHz, CDCl$_3$) δ 1.37 (d, 3H, J=6.4 Hz),1.72 (s, 1H), 2.40-2.51 (m, 4H), 2.58-2.65 (m, 2H), 3.16-3.37 (m, 3H), 3.60-3.62 (m, 4H), 4.22-4.40 (m, 4H), 7.47 (d, 2H, J=8.4 Hz), 7.64 (d, 2H, J=8.4 Hz)

Allyl (5R,6S)-3-(3-fluoro-4-methoxyphenyl)-6-[(1R)-1-hydroxyethyl]-7-oxo-1-azabicyclo[3.2.0]hept-2-ene-2-carboxylate (0.807 g), tetrakis(triphenylphosphine)palladium (0) (50 mg) and triphenylphosphine (10 mg) were dissolved in THF (12 mL), and thereto was added at room temperature sodium 2-ethylhexanoate (0.5M ethyl acetate solution, 4.46 mL). The solvent was removed in vacuo, and to the residue was added dichloromethane (10 mL). The mixture was extracted with ion-exchange water (10 mL×3 times) and the aqueous layers were combined and stirred for 1 hour in vacuo. The dichloromethane was removed by distillation and the aqueous layer was purified with C18 reverse column chromatography (Wakosil 40C18, 38φ×60 mm, mobile phase; 0~5% THF ice-cooled ion-exchange water). The fractions containing the object compound were combined and THF therein was removed in vacuo under stirring for 1 hour. The residue was lyophilized to give sodium (5R,6S)-3-(3-fluoro-4-methoxyphenyl)-6-[(1R)-1-hydroxyethyl]-7-oxo-1-azabicyclo[3.2.0]hept-2-ene-2-carboxylate (450 mg, yield 59%).

¹H NMR (400 MHz, DMSO-d₆) δ 1.08 (d, 3 H, J=6.3 Hz), 2.83 (dd, 1 H, J=9.9 Hz, 15.7 Hz), 2.97 (dd, 1 H, J=8.5 Hz, 15.7 Hz), 3.06 (dd, 1 H, J=2.8 Hz, 6.6 Hz), 3.76 (s, 3 H), 3.80-3.88 (m, 1 H), 3.89-3.95 (m, 1 H), 4.94 (d, 1 H, J=5.0 Hz), 6.94 (t, 1 H, J=9.0 Hz), 7.06-7.10 (m, 1 H), 7.56 (dd, 1 H, J=2.1 Hz, 14.1 Hz).

LCMS (EI) 322 (M+1⁺).

Example 34

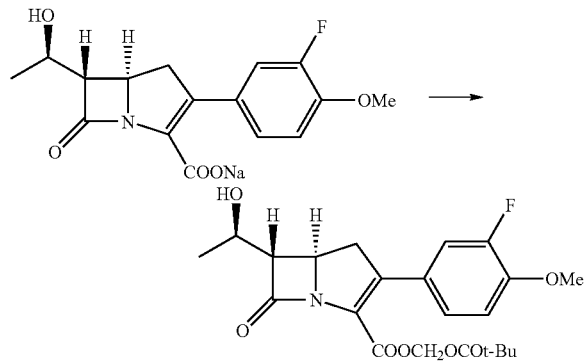

To sodium (5R,6S)-3-(3-fluoro-4-methoxyphenyl)-6-[(1R)-1-hydroxyethyl]-7-oxo-1-azabicyclo[3.2.0]hept-2-ene-2-carboxylate (100 mg) in DMF (3 mL) was added at 0° C. pivaloyloxymethyl iodide (77 mg), and the mixture was stirred for 15 minutes. To the reaction mixture was added diethyl ether (50 mL), and the mixture was washed with saturated brine (50 mL×3times), dried over magnesium sulfate, filtered, and the solvent was removed in vacuo. The residue was purified under silica gel column chromatography (chloroform:methanol=100:0~100:3) to give [(2,2-dimethyl-propanoyl)oxy]methyl (5R,6S)-3-(3-fluoro-4-methoxyphenyl)-6-[(1R)-1-hydroxyethyl]-7-oxo-1-azabicyclo[3.2.0]hept-2-ene-2-carboxylate (70 mg, 55%).

¹H NMR (400 MHz, CDCl₃) δ 1.20 (s, 9 H), 1.36 (d, 3 H. J=6.3 Hz), 3.20 (dd, 1 H, J=9.9 Hz, 18.2 Hz), 3.23-3.26 (m, 1 H), 3.29 (dd, 1 H, J=9.0 Hz, 18.2 Hz), 3.91 (s, 3 H), 4.22-4.31 (m, 2 H), 5.80 (d, 1 H, J=5.5 Hz), 5.89 (d, 1 H, J=5.5 Hz), 6.90-6.95 (m, 1 H), 7.15-7.20 (m, 2 H).

LCMS (EI) 436 (M+1⁺).

The compounds listed in tables below were prepared in the same manner as in Example 33 and Example 34.

TABLE 29

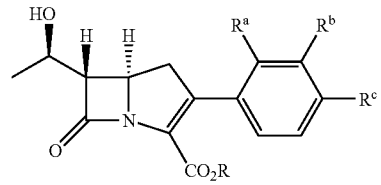

| | Example 35 | Example 36 | Example 37 |
|---|---|---|---|
| Rᵃ | —H | —H | —H |
| Rᵇ | —OCH₃ | —OCH₃ | —OCH₃ |
| Rᶜ | —F | —F | —OCH₃ |
| R | —Na | —CH₂OCOt-Bu | —Na |
| Physical data | ¹H NMR(DMSO-d₆, 400MHz)δ1.15(d, 3 H, J=6.3Hz), 2.92 (dd, 1H, J=9.9Hz,Hz), 15.8Hz), 3.08(dd, 1 H, J=8.5Hz, 15.8 Hz), 3.14(dd, 1H, J=2.8Hz, 6.5Hz), 3.77(s, 3H), 3.89-3.94(m, 1H), 3.98-4.03(m, 1H), 5.01 (d, 1H, J=4.9Hz), 6.96 (ddd, 1H, J=2.1Hz, Hz, 4.5Hz, 8.5Hz), 7.04(dd, 1H, J=8.5 Hz, 11.4Hz), 7.57 (dd, 1H, J=2.0Hz, 8.8Hz). IR(ATR)3336, 2970, 1743, 1597, 1516, 1454, 1392, 1323, 1304, 1261, 1238, 1223, 1207, 1176, 1122, 1026, 949, | ¹H NMR(CDCl₃, 400 MHz)δ1.17(s, 9H), 1.36(d, 3H, J=6.3 3.22(dd, 1H, J= 9.9Hz, 18.3Hz), 3.25-3.27(m, 1H), 3.29(dd, 1H, J=9.0 Hz, 18.4Hz), 3.89(s, 3H), 4.21-4.32(m, 2 H), 5.78(d, 1H, J= 5.5Hz), 5.86(d, 1H, J=5.5Hz), 6.88 (ddd, 1H, J=2.1 4.3Hz, 8.4Hz), 7.04 (dd, 1H, J=8.4Hz, 10.9Hz), 7.07-7.09 (m, 1H). LCMS(EI)436 (M+1+). | ¹H NMR(400MHz, D₂O)δ1.18(d, 3H, J=5.4Hz), 2.90(dd, 1H, J=16.8Hz, 9.6Hz), 3.22(dd, 1H, J=16.8Hz, 8.4Hz), 3.31-3.33(m, 1H), 3.69(s, 3H), 3.72(s, 3H), 4.08-4.15(m, 2H), 6.77-6.88(m, 2H), 6.93(s, 1H) |

TABLE 29-continued

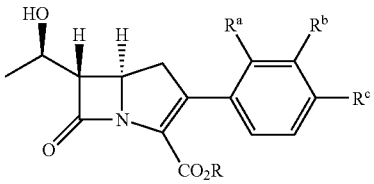

| | Example 35 | Example 36 | Example 37 |
|---|---|---|---|
| | 906, 852, 810, 771, 702 cm$^{-1}$. LCMS(EI)322 (M+1+). | | |

TABLE 30

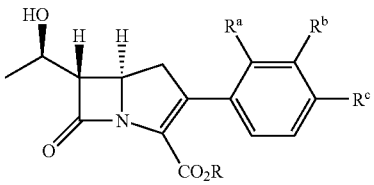

| | Example 38 | Example 39 | Example 40 |
|---|---|---|---|
| $R^a$ | —H | —H | —H |
| $R^b$ | —OCH$_3$ | —CH$_3$ | —CH$_3$ |
| $R^c$ | —OCH$_3$ | —OCH$_3$ | —OCH$_3$ |
| R | —CH$_2$OCOt-Bu | —Na | —CH$_2$OCOt-Bu |
| Physical data | $^1$H NMR(400MHz, CDCl$_3$)δ1.18(s, 9H), 1.37(d, 3H, J=6.0Hz), 1.69(d, 1H, J=4.8Hz), 3.21-3.31(m, 3H), 3.88(s, 3H), 3.90(s, 3H), 4.24-4.29(m, 2H), 5.81(d, 1H, J=5.6Hz), 5.88(d, 1H, J=5.6Hz), 6.82 (d, 1H, J=8.4Hz), 6.98(dd, 1H, J=8.4Hz, 2.0Hz), 7.07(d, 1H, J=2.0Hz) | $^1$H NMH(400MHz, D$_2$O)δ1.20(d, 3H, J=6.4Hz), 2.06(s, 3H), 2.93(dd, 1H, J=16.9Hz, 9.7Hz), 3.28(dd, 1H, J=16.9Hz, 8.6Hz), 3.33-3.39(m, 1H), 3.74(s, 3H), 4.08-4.22(m, 2H), 6.82-6.89(m, 1H), 7.00-7.14(m, 2H) | $^1$H NMH(400MHz, CDCl$_3$)δ1.19(s, 9H), 1.37(d, 3H, J=6.3Hz), 1.78(d, 1H, J=4.9Hz), 2.20(s, 3H), 3.15-3.33(m, 3H), 3.85(s, 3H), 4.20-4.31(m, 2H), 5.80(d, 1H, J=5.5Hz), 5.88(d, 1H, J=5.5Hz), 6.79(d, 1H, J=8.5Hz), 7.17(s, 1H), 7.23-7.27(m, 1H) |

TABLE 31

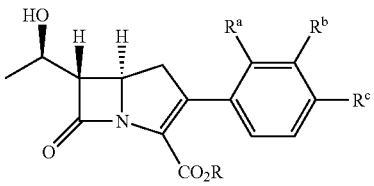

| | Example 41 | Example 42 | Example 43 |
|---|---|---|---|
| $R^a$ | —H | —H | —H |
| $R^b$ | —Cl | —Cl | —NH$_2$ |
| $R^c$ | —NH$_2$ | —NH$_2$ | —Cl |
| R | —Na | —CH$_2$OCOt-Bu | —Na |
| Physical data | $^1$H NMR(400MHz, D$_2$O)δ1.25(d, 3H, J=6.4Hz), 2.98(dd, 1H, J=16.8Hz, 9.7Hz), 3.30(dd, 1H, J=16.8Hz, 8.6Hz), | $^1$H NMR(400MHz, CDCl$_3$)δ1.21(s, 9H), 1.36(d, 3H, J=6.3Hz), 1.81(br s, 1H), 3.13-3.30(m, 3H), 4.19-4.28(m, 4H), 5.81(d, | $^1$H NMR(400MHz, D$_2$O)δ1.22(d, 3H, J=6.4Hz), 2.97(dd, 1H, J=17.0Hz, 9.8Hz), 3.30(dd, 1H, J= 7.0Hz, 8.4Hz), 3.39- |

TABLE 31-continued

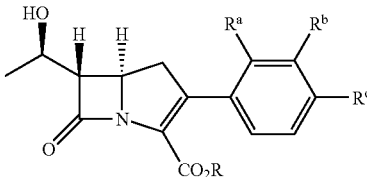

| | Example 41 | Example 42 | Example 43 |
|---|---|---|---|
| | 3.37-3.44(m, 1H), 4.12-4.25(m, 2H), 6.85(d, 1H, J=8.4Hz), 7.11(dd. 1H, J=8.4Hz, 2.1Hz), 7.29 (d. 1H, J=2.0Hz) | 1H, J=5.5Hz), 5.89(d, 1H, J=5.5Hz), 6.70(d, 1H, J=8.4Hz), 7.21 (dd, 1H,J=8.4Hz, 2.0Hz), 7.37(d, 1H, J=8.4Hz) | 3.45(m,1H), 4.12-4.25(m, 2H), 6.70 (dd, 1H, J=8.3Hz, 2.1Hz), 6.83(d. 1H, J=2.1Hz), 7.21(d. 1H, J=8.3Hz) |

TABLE 32

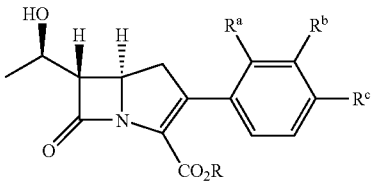

| | Example 44 | Example 45 | Example 46 |
|---|---|---|---|
| $R^a$ | —H | —H | —H |
| $R^b$ | —$NH_2$ | —$NH_2$ | —$NH_2$ |
| $R^c$ | —Cl | —$OCH_3$ | —$OCH_3$ |
| R | —$CH_2OCOt$-Bu | —Na | —$CH_2OCOt$-Bu |
| Physical data | $^1$H NMR(400MHz, CDCl$_3$)δ1.18(s, 9H), 1.36(d, 3H, J=6.3Hz), 1.78(d, 1H, J=4.78Hz), 3.11-3.32 (m, 3H), 4.07-4.20(m, 2H), 4.21-4.31(m, 2H), 5.77(d, 1H, J=5.5Hz), 5.86(d, 1H, J=5.5Hz), 6.63(dd, 1H, J=8.3Hz, 2.0Hz), 6.79(d, 1H, J=2.0Hz), 7.20(d, 1H, J=8.3Hz) | $^1$H NMR(400MHz, D$_2$O)δ1.19(d, 3H, J=6.4Hz), 2.92(dd, 1H, J=16.9Hz, 9.7Hz), 3.25(dd, 1H, J=16.9Hz, 8.6Hz), 3.31-3.39(m, 1H), 3.74(s, 3H), 4.08-4.20(m, 2H), 6.66-6.79(m, 2H), 6.81(d, 1H, J=8.4Hz) | $^1$H NMR(400MHz, CDCl$_3$)δ1.19(s, 9H), 1.37(d, 3H, J=6.3Hz), 1.76(br s, 1H), 3.13-3.30(m, 3H), 3.87(s, 3H), 4.18-4.31(m, 2H), 5.80(d, 1H, J=5.5Hz), 5.87(d, 1H, J=5.5Hz), 6.65-7.01 (m, 3H) |

TABLE 33

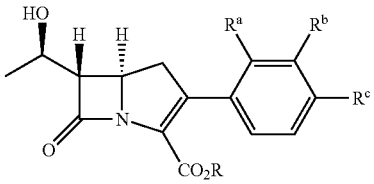

| | Example 47 | Example 48 | Example 49 |
|---|---|---|---|
| $R^a$ | —H | —H | —H |
| $R^b$ | —$NH_2$ | —$NH_2$ | —F |
| $R^c$ | —$CH_3$ | —$CH_3$ | —$NH_2$ |
| R | —Na | —$CH_2OCOt$-Bu | —Na |
| Physical data | $^1$H NMR(400MHz, D$_2$O)δ1.19(d, 3H, J=6.4Hz), 2.04(s, 3H), 2.93(dd, 1H, J=16.9Hz, 9.8Hz), 3.27(dd, 1H, | $^1$H NMR(400MHz, CDCl$_3$)δ1.19(s, 9H), 1.37(d, 3H, J=6.3Hz), 1.73(d, 1H, J=4.9Hz), 2.16(s, 3H), 3.12-3.29(m, | $^1$H NMR(400MHz, D$_2$O)δ1.17(d, 3H, J=6.4Hz), 2.86(dd, 1H, J=16.8Hz, 9.6Hz), 3.18(dd, 1H, J=16.8Hz, 8.4Hz), |

TABLE 33-continued

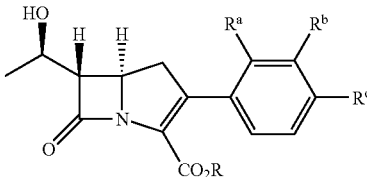

| | Example 47 | Example 48 | Example 49 |
|---|---|---|---|
| | J=16.9Hz, 8.5Hz), 3.38(dd, 1H, J=6.4Hz, 2.8Hz), 4.08-4.21(m, 2H), 6.67(dd, 1H, J=7.7Hz, 1.6Hz), 6.70(d, 1H, J=1.6Hz), 6.99(d, 1H, J=7.7Hz) | 3H), 3.68(br s, 2H), 4.20-4.30(m, 2H), 5.78(d, 1H, J=5.5Hz), 5.86(d, 1H, J=5.5Hz), 6.67 (dd, 1H, J=7.7Hz, 1.7Hz), 6.71(d, 1H, J=1.7Hz), 7.00(d, 1H, J=7.7Hz) | 3.28-3.30(m, 1H), 4.06-4.12(m, 2H), 6.73(t, 1H, J=8.4Hz), 6.87(dd, 1H, J=8.4Hz, 2.0Hz), 6.96(dd, 1H, J=8.8Hz, 2.0Hz) |

TABLE 34

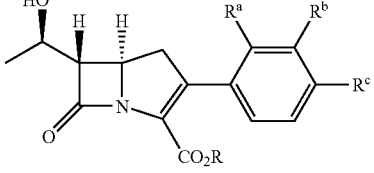

| | Example 50 | Example 51 | Example 52 |
|---|---|---|---|
| $R^a$ | —H | —H | —H |
| $R^b$ | —F | —F | —F |
| $R^c$ | —NH$_2$ | —NHCOCH$_3$ | —NHCOCH$_3$ |
| R | —CH$_2$OCOt-Bu | —Na | —CH$_2$OCOt-Bu |
| Physical data | $^1$H NMR(400MHz, CDCl$_3$)δ1.20(s, 9H), 1.36(d, 3H, J=6.0Hz), 1.77(d, 1H, J=4.8Hz), 3.16-3.27(m, 3H), 3.93 (br s, 2H), 4.21-4.27 (m, 2H), 5.81(d, 1H, J=6.4Hz), 5.90(d, 1H, J=6.4Hz), 6.70 (t, 1H, J=8.4Hz), 7.06(dd, 1H, J=8.4Hz, 1.0Hz), 7.16(dd, 1H, J=12.4Hz, 1.0Hz) | $^1$H NMR(400MHz, D$_2$O)δ1.17(d, 3H, J=5.6Hz), 2.06(s, 3H), 2.95(dd, 1H, J=16.8Hz, 10Hz), 3.28(dd, 1H, J=16.8Hz, 8.8Hz), 3.37-3.39(m, 1H), 4.06-4.22(m, 2H), 7.02-7.09(m, 2H), 7.42(t, 1H, J=8.0Hz) | $^1$H NMR(400MHz, CDCl$_3$)δ1.20(s, 9H), 1.37(d, H, J=6.4Hz), 1.77(d, 1H, J=4.8Hz), 2.23 (s, 3H), 3.17-3.33 (m, 3H), 4.24-4.31 (m, 2H), 5.79(d, 1H, J=5.6Hz), 5.88(d, 1H, J=5.6Hz), 7.12 (d, 1H, J=8.4Hz), 7.20(m, 1H), 7.40 (s, 1H), 8.34(t, 1H, J=8 .0Hz) |

TABLE 35

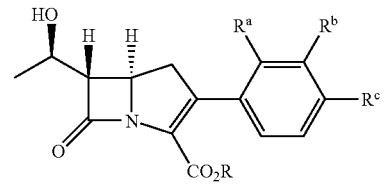

| | Example 53 | Example 54 |
|---|---|---|
| $R^a$ | —H | —H |
| $R^b$ | —F | —F |
| $R^c$ | —NHCOOCH$_3$ | —NHCOOCH$_3$ |
| R | Na | —CH$_2$OCOt-Bu |
| Physical | $^1$H NMR(400MHz, D$_2$O)δ1.22 | $^1$H NMR(400MHz, CDCl$_3$)δ |

TABLE 35-continued

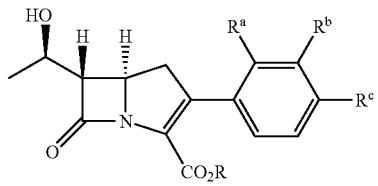

| | Example 53 | Example 54 |
|---|---|---|
| data | (d, 3H, J=6.4Hz), 3.01(dd, 1H, J=17.2Hz, 9.6Hz), 3.30(dd, 1H, J=17.2Hz, 8.4Hz), 3.42-3.44(m, 1H), 4.16-4.22(m, 2H), 7.07-7.13(m, 2H), 7.55(t, 1H, J=8.0Hz) | 1.19(s, 9H), 1.36(d, 3H, J=6.4Hz), 1.78(d, 1H, J=4.8Hz), 3.17-3.33(m, 3H), 3.81(s, 3H), 4.24-4.31(m, 2H), 5.79(d, 1H, J=5.6Hz), 5.88(d, 1H, J=5.6Hz), 6.99(s, 1H), 7.14(d, 1H, J=8.8Hz), 7.20-7.23(m, 1H), 8.10(brs, 1H) |

TABLE 36

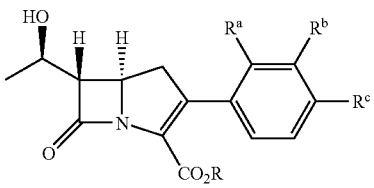

| | Example 55 | Example 56 | Example 57 |
|---|---|---|---|
| $R^a$ | —H | —H | —H |
| $R^b$ | —CONH$_2$ | —Cl | —Cl |
| $R^c$ | —OCH$_3$ | —NHCO-(4-pyridyl) | —NHCO-(4-pyridyl) |
| R | —Na | —Na | —CH$_2$OCOt-Bu |
| Physical data | $^1$H NMR(D$_2$O, 400MHz) · 1.25(d, 3H, J=6.4Hz), 3.02 (dd, 1H, J=17.0Hz, 9.8Hz), 3.37(dd, 1H, J=17.0Hz, 8.6Hz), 3.44(dd, 1H, J=6.0Hz, 2.7Hz), 3.90(s, 3H), 3.95-3.98(m, 1H), 4.21-4.24(m, 1H), 7.08(d, 1H, J=8.8Hz), 7.50(dd, 1H, J=8.7Hz, 2.4Hz), 7.69(d, 1H, J=2.4Hz). LCMS(EI)347 (M+1+). | $^1$H NMR(D$_2$O, 300MHz) · 1.20(d, 3H, J=6.4Hz), 2.97 (dd, 1H, J=16.8Hz, 9.7Hz), 3.29(dd, 1H, J=16.8Hz, 8.4Hz), 3.40(dd, 1H, J=5.9Hz, 2.7Hz), 4.10-4.23 (m, 2H), 7.25(dd, 1H, J=8.4Hz, 1.9Hz), 7.42(d, 1H, J=1.9Hz), 7.45(d, 1H, J=8.4Hz), 7.73-7.75(m, 2H), 8.61-8.63(m, 2H). IR(ATR)751, 1664, 1578, 1516, 1389, 1308, 1254, 1221, 1130, 1055, 1001, 897cm$^{-1}$. | $^1$H NMR(CDCl$_3$, 300MHz) · 1.21(s, 9H), 1.37(d, 3H, J=6.2Hz), 3.18-3.38 (m, 3H), 4.24-4.36 (m, 2H), 5.81(d, 1H, J=5.5Hz), 5.89(d, 1H, J=5.5Hz), 7.36 (dd, 1H, J=8.6Hz, 2.0Hz), 7.54(d, 1H, J=2.0Hz), 7.73-7.76 (m, 2H), 8.52(br s, 1H), 8.57(d, 1H, J=8.6Hz), 8.85-8.87 (m, 2H). IR(ATR)1751, 1686, 1599, 1572, 1514, 1479, 1394, 1369, 1261, 1192, 1116, 1095, 1053, 1024, 980, 887, 827 cm$^{-1}$. |

TABLE 37

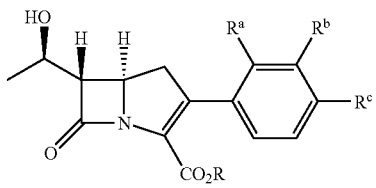

| | Example 58 | Example 59 | Example 60 |
|---|---|---|---|
| $R^a$ | —H | —H | —H |
| $R^b$ | —Cl | —Cl | —Cl |
| $R^c$ | —NHCO-(2-furyl) | —NHCO-(2-furyl) | —NHCO-(2-pyrrolyl) |
| R | —Na | —CH$_2$OCOt-Bu | —Na |
| Physical data | $^1$H NMR(D$_2$O, 300 MHz) · 1.19(d, 3H, J=6.4Hz), 2.99(dd, 1H, J=16.8Hz,9.7 Hz), 3.30(dd, 1H, J= 16.8Hz, 8.2Hz), 3.41(dd, 1H, J= 6.0Hz, 2.7Hz), 4.10-4.22(m, 2H), 6.58(dd, 1H, J= 3.7Hz, 1.7Hz), 7.21 (dd, 1H, J=3.7Hz, 0.9Hz), 7.24(dd, 1 H, J=8.4Hz, 2.0 Hz), 7.43(d, 1H, J= 2.0Hz), 7.47(d, 1H, J=8.4Hz), 7.64(dd, 1H, J=1.7Hz, 0.9 Hz). IR(ATR) 1749, 1676, 1589, 1518, 1462, 1389, 1308, 1261, 1228, 1165, 1138, 1113, 1049, 1011, 885, 750cm$^{-1}$. | $^1$H NMR(CDCl$_3$, 300MHz) · 1.20 (s, 9H), 1.37(d, 3 H, J=6.2Hz), 3.17-3.36(m, 3H), 4.23-4.34(m, 2H), 5.81(a, 1H, J= 5.5Hz), 5.89(d, 1 H, J=5.5Hz), 6.60 (dd, 1H, J=3.5 Hz, 1.8Hz), 7.29 (dd, 1H, J=3.5 Hz, 0.9Hz), 7.32 (dd, 1H, J=8.6 Hz, 2.0Hz), 7.52 (d, 1H, J=2.0Hz), 7.57(dd, 1H, J= 1.8Hz, 0.9Hz), 8.56(d, 1H, J= 8.6Hz), 8.77(br s, 1H). IR(ATR) 1751, 1686, 1589, 1514, 1460, 1396, 1313, 1261, 1192, 1160, 1097, 1022, 980, 883, 823, 758cm$^{-1}$. LCMS(EI) 531 (M+1+). | $^1$H NMR(D$_2$O, 300 MHz) · 1.20(d, 3 H, J=6.6Hz), 3.00 (dd, 1H, J=16.7 Hz, 10.3Hz), 3.31 (dd, 1H, J=16.7 Hz, 8.4Hz), 3.42 (dd, 1H, J=6.0Hz, 2.7Hz), 4.10-4.23 (m, 2H), 6.26-6.28 (m, 1H), 6.94(d, 1 H, J=3.9Hz), 7.04-7.05(m, 1H), 7.22-7.26(m, 1H), 7.39-7.43(m, 2H). LCMS(EI)416 (M+1+). |

TABLE 38

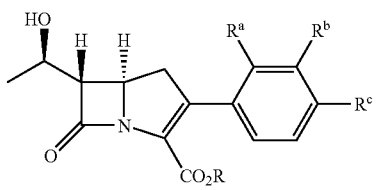

| | Example 61 | Example 62 | Example 63 |
|---|---|---|---|
| $R^a$ | —H | —H | —H |
| $R^b$ | —Cl | —CN | —CN |
| $R^c$ | —NHCO-(2-pyrrolyl) | —OMe | —OMe |
| R | —CH$_2$OCOt-Bu | —Na | —CH$_2$OCOt-Bu |
| Physical data | $^1$H NMR(CDCl$_3$, 300MHz) · 1.20 | $^1$H NMR(D$_2$O, 300 MHz) · 1.15(d, | $^1$H NMR(CDCl$_3$, 300MHz) · 1.20 |

TABLE 38-continued

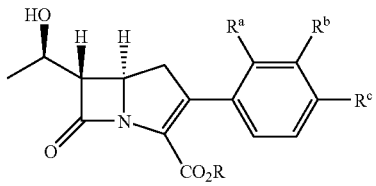

| Example 61 | Example 62 | Example 63 |
|---|---|---|
| (s, 9H), 1.37(d, 3 H, J=6.4Hz), 3.17-3.36(m, 3H), 4.25-4.34(m, 2H), 5.80(d, 1H, J= 5.5Hz), 5.89(d, 1 H, J=5.5Hz), 6.31-6.35(m, 1H), 6.78-6.81(m, 1H), 7.03-7.06(m, 1H), 7.29-7.33(m, 1H), 7.51-7.52(m, 1H), 8.25(br s, 1H), 8.49-8.52(m, 1H), 9.59(br s, 1H). | 3H, J=6.4Hz), 2.89(dd, 1H, J=16.8 Hz, 9.7Hz), 3.23 (dd, 1H, J=16.8 Hz, 8.4Hz), 3.33 (dd, 1H, J=6.0 Hz, 2.7Hz), 4.03-4.17(m, 2H), 6.96 (d, 1H, J=9.2Hz), 7.44-7.48(m, 2H). | (s, 9H), 1.37(d, 3 H, J=6.4Hz), 3.15-3.34(m, 3H), 3.97(s, 3H), 4.23-4.34(m, 2H), 5.79 (d, 1H, J=5.5Hz), 5.88(d, 1H, J= 5.5Hz), 6.97(d, 1 H, J=9.0Hz), 7.58 (d, 1H, J=2.2Hz), 7.65(dd, 1H, J= 9.0, 2.2Hz). |

TABLE 39

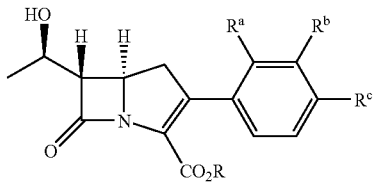

| | Example 64 | Example 65 | Example 66 |
|---|---|---|---|
| R$^a$ | —H | —H | —H |
| R$^b$ | —Cl | —Cl | —Cl |
| R$^c$ | —OCH$_3$ | —OCH$_3$ | —OCH$_3$ |
| R | —Na | —CH$_2$OCOt-Bu | 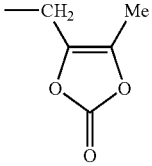 |
| Physical data | $^1$H NMR(400MHz, D$_2$O)δ1.11(d, 3H, J=6.4Hz), 2.86(dd, 1H, J=17.0Hz, 9.8Hz), 3.17(dd, 1H, J=17.0Hz, 8.5Hz), 3.29-3.31(m, 1H), 3.72(s, 3H), 4.03-4.12(m, 2H), 6.90(d, 1H, J=9.7Hz), 7.11 (dd, 1H, J=8.6Hz, 2.2Hz), 7.25(d, 1H, J=2.2Hz) | $^1$H NMR(400MHz, CDCl$_3$)δ1.20(s, 9H), 1.36(d, 3H, J=6.3Hz), 1.79(d, 1H, J=4.8Hz), 3.17-3.31(m, 3H), 3.93(s, 3H), 4.24-4.31(m, 2H), 5.80(d, 1H, J=5.5Hz), 5.88(d, 1H, J=5.5Hz), 6.90 (d, 1H, J=8.6Hz), 7.33(dd, 1H, J=8.6Hz, 2.2Hz), 7.41(d, 1H, J=2.2Hz) | $^1$H NMR(400MHz, CDCl$_3$)δ1.37(d, 3H, J=6.3Hz), 1.79(d, 1H, J=4.7Hz), 2.16 (s, 3H), 3.17-3.32(m, 3H), 3.93(s, 3H), 4.25-4.31(m, 2H), 4.88(d, 1H, J=13.9Hz), 4.97(d, 1H, J=13.9Hz), 6.91 (d, 1H, J=8.6Hz), 7.25-7.28(m, 1H), 7.38(d, 1H, J=2.2Hz) |

TABLE 40

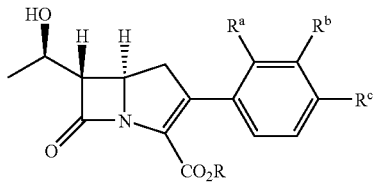

| | Example 67 | Example 68 |
|---|---|---|
| $R^a$ | —H | —H |
| $R^b$ | —Cl | —Cl |
| $R^c$ | —NHCO-CH2-(4-pyridyl) | —NHCO-CH2-(4-pyridyl) |
| R | —Na | —CH$_2$OCOt-Bu |
| Physical data | $^1$H NMR(400MHz, CDCl$_3$) δ 1.12(d, 3H, J=6.4Hz), 2.90(dd, 1H, J=17.0Hz, 9.9Hz), 3.22(dd, 1H, J=17.0Hz, 8.5Hz), 3.33(m, 1H), 3.73(s, 2H), 4.06-4.15(m, 2H), 7.13(dd, 1H, J=8.4Hz, 2.0Hz), 7.23-7.37(m, 4H), 8.33 (dd, 2H, J=4.6Hz, 1.6Hz) | $^1$H NMR(400MHz, CDCl$_3$) δ 1.18(s, 9H), 1.35(d, 3H, J=6.3Hz), 1.81(br s, 1H), 3.14-3.31(m, 3H), 3.79(s, 2H), 4.26-4.31(m, 2H), 5.77(d, 1H, J=5.5Hz), 5.86(d, 1H, J=5.5Hz), 7.24-7.27(m, 1H), 7.31(d, 2H, J=4.5Hz), 7.42(d, 1H, J=2.0Hz), 7.69(br s, 1H), 8.38(d, 1H, J=8.6Hz), 8.65(d, 2H, J=4.4Hz) |

TABLE 41

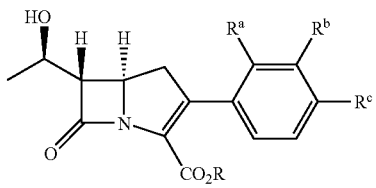

| | Example 69 | Example 70 |
|---|---|---|
| $R^a$ | —H | —H |
| $R^b$ | —NH$_2$ | —NH$_2$ |
| $R^c$ | —CH$_2$CH$_2$CONH-CH$_2$-(4-pyridyl) | —CH$_2$CH$_2$CONH-CH$_2$-(4-pyridyl) |
| R | —Na | —CH$_2$OCOt-Bu |
| Physical data | $^1$H NMR(400MHz, DMSO-d$_6$)δ 1.16(d, 3H, J=6.3Hz), 2.84 (dd, 1H, J=9.8Hz, 16.0Hz), 3.08(dd, 1H, J=8.6Hz, 16.0 Hz), 3.16(dd, 1H, J=2.7Hz, 6.6Hz), 3.37(s, 2H), 3.84-3.88 (m, 1H), 4.02(td, 1H, J=9.2 Hz 2.6Hz), 4.28(d, 2H, J=6.1 Hz), 5.01(br s, 2H), 6.69(d, 1H, J=1.6Hz), 6.75(dd, 1H,J=Hz), 7.8Hz), 6.90(d, 1H, J= 7.8Hz), 7.20-7.23(m, 2H), 8.46-8.48(m, 2H), 8.71(t, 1H, J=6.0Hz). LCMS(EI)437(M−Na+1)$^+$. | $^1$H NMR(400MHz, CDCl$_3$)δ 1.17(s, 9 H), 1.34(d, 3H, J= 6.3Hz), 3.13(dd, 1H, J=18.4 Hz, 9.9Hz), 3.20-3.27(m, 2H), 3.55(s, 2H), 4.18-4.28(m, 2H), 4.40(d, 2H, J=6.2Hz), 5.67(d, 1H, J=5.5Hz), 5.76(d, 1H, J= 5.5Hz), 6.65(dd, 1H, J=7.7 Hz, 1.7Hz), 6.70(d, 1H, J=1.7 6.74(t, 1H, J=6.7Hz), 7.02(d, 1H, J=7.7Hz), 7.11-7.13(m, 2H), 8.46-8.47(m, 2H). LCMS(EI)551(M+1)$^+$. |

TABLE 42

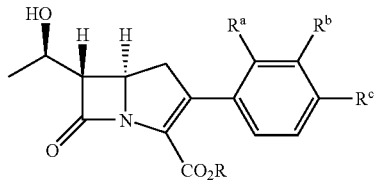

| | Example 71 | Example 72 |
|---|---|---|
| $R^a$ | —H | —H |
| $R^b$ | —Cl | —$NH_2$ |
| $R^c$ | —$NHCOCH_2NH_2$ | —OH |
| R | —H | —Na |
| Physical data | $^1$H NMR(400MHz, $D_2O$)δ1.17 (d, 3H, J=5.6Hz),, 2.98(dd, 1H, J=16.8Hz, 10Hz), 3.30(dd, 1H, J=16.8Hz, 8.4Hz), 3.40-3.42(m, 1H), 4.13-4.23(m, 2H), 7.21-7.23(m, 2H), 7.40(s, 1H), 7.44-7.48(m, 2H) | $^1$H NMR(400MHz, $D_2O$)δ1.15 (d, 3H, J=5.6Hz),, 2.86(dd, 1H, J=17.2Hz, 10Hz), 3.30(dd, 1H, J=17.2Hz, 8.4Hz), 3.30-3.32(m, 1H), 4.07-4.13(m, 2H), 6.58-6.67(m, 2H), 6.78(s, 1H) |

Example 73

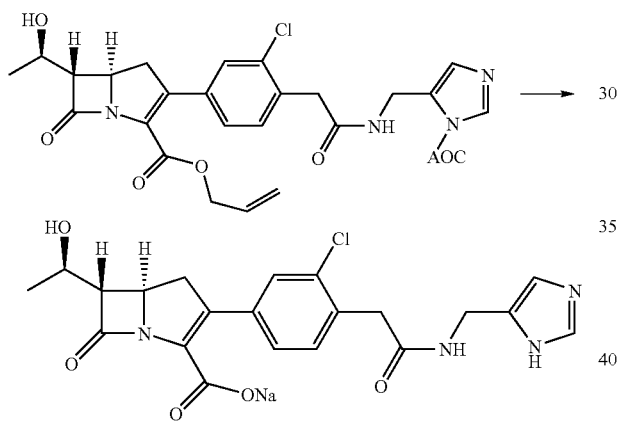

Allyl (5R,6S)-3-(4-{2-[({1-[(allyloxy)carbonyl]-1H-imidazol-5-yl}methyl)amino]-2-oxoethyl}-3-chlorophenyl)-6-[(1R)-1-hydroxyethyl]-7-oxo-1-azabicyclo[3.2.0]hept-2-ene-2-carboxylate (0.11 g) was dissolved under ice cooling in a mixture solution of dichloromethane (5.4 mL) and ion-exchange water (10.8 mL), and thereto were added dichlorobistriphenylphosphine palladium (6.7 mg, 0.005 mmol) and tri-n-butyltin hydride (0.52 mL, 1.9 mmol). The mixture was allowed to stand after vigorously stirring for 10 minutes. Thereto was added ice-cooled ion-exchanged water (10.8 mL), and the aqueous layer was separated and extracted with ion-exchanged water (5 mL×twice). The aqueous solution separated and extracted was ice cooled, and thereto was added sodium hydrogencarbonate (16 mg, 0.19 mmol), followed by stirring for 10 minutes. The solvent of the mixture was removed under ice cooling in vacuo over a period of 2 hours, purified with C18 reverse column chromatography (Wakosil C18 reverse, mobile phase; ion-exchange water/THF=100: 0~100:3) and lyophilized to give sodium (5R,6S)-3-(3-chloro-4-{2-[(1H-imidazol-5-ylmethyl)amino]-2-oxoethyl}phenyl)-6-[(1R)-1-hydroxyethyl]-7-oxo-1-azacyclo[3.2.0]hept-2-ene-2-carboxylate (38 mg, yield 43%).

$^1$H NMR (400 MHz, $D_2O$) δ 1.15 (d, 3H, J=6.0 Hz), 2.96 (dd, 1H, J=16.8 Hz, 10.0 Hz), 3.29 (dd, 1H, J=17.2 Hz, 8.4 Hz), 3.39-3.41 (m, 1H), 3.65 (s, 2H), 4.10-4.28 (m, 4H), 6.91 (s, 1H), 7.18 (s, 1H), 7.18 (d, J=8.8 Hz, 1H), 7.30 (d, J=8.8 Hz, 1H), 7.61 (s, 1H)

Example 74

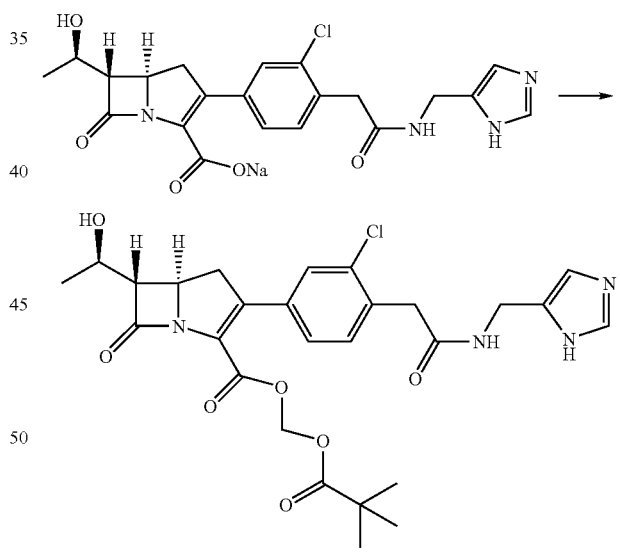

Sodium (5R,6S)-3-(3-chloro-4-{2-[(1H-imidazol-5-ylmethyl)amino]-2-oxoethyl}phenyl)-6-[(1R)-1-hydroxyethyl]-7-oxo-1-azabicyclo[3.2.0]hept-2-ene-2-carboxylate (76 mg) prepared by Example 73 was dissolved in dry DMF (1.5 mL), and thereto were added pivalpyloxymethyl chloride (56 μL) and benzyl diethylammonium chloride (87.6 mg). The mixture was stirred at 35° C. for 2 hours. To the reaction solution were added ethyl acetate, saturated sodium hydrogencarbonate solution and ice, and the mixture was separated by a separatory funnel, and the organic layer was washed with cooled water (twice), and cooled brine, dried over anhydrous sodium sulfate and the solvent was removed in vacuo. The residue was purified with silica gel column chromatography (chloroform:methanol=100:10~100:16) to give [(2,2-dimethylpropanoyl)oxy]methyl (5R,6S)-3-(3-chloro-4-{2-[(1H-imidazol-5-ylmethyl)amino]-2-oxoethyl}phenyl)-6-[(1R)-1-hydroxyethyl]]-7-oxo-1-azabicyclo[3.2.0]hept-2-ene-2-carboxylate (30 mg, yield 49%).

$^1$H NMR (400 MHz, CDCl$_3$) δ 1.13 (s, 9H), 1.38 (d, 3H, J=6.4 Hz), 3.10-3.28 (m, 3H), 3.70 (s, 1H), 4.17-4.51 (m, 4H), 5.66 (d, 1H, J=5.6 Hz), 5.79 (d, 1H, J=5.6 Hz), 6.90 (s, 1H), 7.16 (dd, J=8.0, 2.0 Hz, 1H), 7.24 (s, 1H), 7.35 (d, J=8.4 Hz, 1H), 7.54 (s, 1H)

Test

Oral Absorption Test

A compound of Example 1 of the present invention and a pivaloyloxymethyl ester derivative of the compound 32, carbapenem in which para-hydroxyphenyl group is directly substituted, which is described in the Journal of Medicinal Chemistry, Vol. 30, p 871-880, 1987 (which is one of the prior arts which are most relevant to the present invention) were orally administered to mice or rats. The concentration of the active substance in serum was measured by bioassay, and absolute bioavailability was compared respectively.

Test Compound (Ester Compound) and Active Substance

The compound of Example 1 of the present invention:

[(2,2-dimethylpropanoyl)oxymethyl (5R,6S)-6-[(1R)-1-hydroxyethyl]-3-(4-methoxyphenyl)-7-oxo-1-azabicyclo [3.2.0]hept-2-ene-2-carboxylate

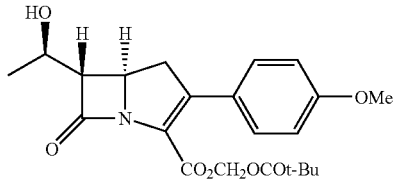

The comparative compound (a pivaloyloxymethyl ester derivative of compound 32 described in the Journal of Medicinal Chemistry, Vol. 30, p 871-880, 1987)):

[(2,2-dimethylpropanoyl)oxymethyl (5R,6S)-6-[(1R)-1-hydroxyethyl]-3-(4-hydroxyphenyl)-7-oxo-1-azabicyclo [3.2.0]hept-2-ene-2-carboxylate

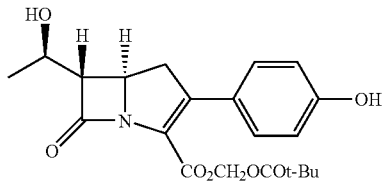

An active substance of the compound of Example 1 of the present invention (sodium carboxylate corresponding to the compound of Example 1):

Sodium (5R,6S)-6-[(1R)-1-hydroxyethyl]-3-(4-methoxyphenyl)-7-oxo-1-azabicyclo [3.2.0]hept-2-ene-2-carboxylate

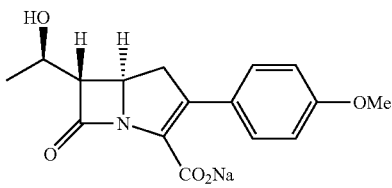

An active substance of the comparative compound (sodium carboxylate corresponding to the compound 32 described in the Journal of Medicinal Chemistry, Vol. 30, p 871-880, 1987):

Sodium (5R,6S)-6-[(1R)-1-hydroxyethyl]-3-(4-hydroxyphenyl)-7-oxo-1-azabicyclo [3.2.0]hept-2-ene-2-carboxylate

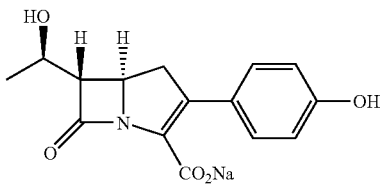

(2) Oral Absorption Test in Mice

The test sample was homogonously suspended in a mixture of DMSO (5%) and methylcellulose (0.5%). Male mice (ICR, 4 weeks old) were fed only with glucose (40%)-casamino acid (5%) solution for 20 hours, and imipenem cilastatin (2 mg) was hypodermally administered 5 minutes before administration of the test sample. To thus treated mice was orally administered the test sample (10 mg value/kg (calculated into active substance). After administration of the test sample, at 5, 15, 30, and 60 minutes, the blood was collected from the mice (n=3), respectively. Serum was obtained by centrifugation of the collected blood. The concentration of the active substance in the serum was measured by bioassay using Bacillus subtilis ATCC 6633 as an indicator. On the other hand, the active substance (10 mg value/kg) was dissolved in physiological saline containing 5mM MOPS and administered in a tail vein of mice, and the blood was collected as well and the serum was subjected to bioassay.

(3) Oral Absorption in Rats

The test sample was prepared in the same manner as in the oral absorption test in mice. Male rats (SD, 7 weeks old) were fed only with sterilized water for 20 hours, and imipenam cilastatin (2 mg) was hypodermally administered 5 minutes before administration of the test sample. To thus treated rats were orally administered the test sample (10 mg value/kg (calculated into active substance)). After administration of the test sample, at 5, 15, 30, and 60 minutes, the blood was collected from the rats (n=3), respectively. The concentration of the active substance in the serum was measured by bioassay in the same manner as in the oral absorption in mice. On the other hand, the active substance (10 mg value/kg) was dissolved in physiological saline containing 5 mM MOPS and administered in a tail vein of rats, and the blood was collected as well and the serum was subjected to bioassay.

(4) Calculation of Bioavailability

In regard to the test sample, the value of the concentration of the active substance in serum was plotted to the hours after administration, and calculated the concentration of the active substance-area under hours curve (AUC) or calculated reducing area under hours curve (AUC) from the concentration of the active substance. On the other hand, AUC when the active substance was intravenously administered was calculated as mentioned above.

BA (%)=(AUC in Oral Administration/AUC in Intravenous Administration) ×100

The absolute availability (BA) was calculated based on the above formula.

In the above tests, the comparative compound did not show oral absorbability in the oral absorption test in rats. On the other hand, the compound of Example 1 of the present invention showed bioavailability more than 30% in both oral absorption tests in rats and mice and the maximum serum concentration (Cmax) was high.

INDUSTRIAL APPLICABILITY

By the present invention, it becomes possible to provide a β-lactam antibiotic with a high oral absorbability showing an excellent antibacterial activity over a broad range of Gram-positive and Gram-negative bacteria, in particular, penicillin-resistant *Streptococcus pneumoniae* (PRSP) which has been isolated at an elevated frequency in recent years and thus causes a serious clinical problem, and *Haemophilus influenzae* which has acquired resistance against the existing β-lactam antibiotics over a wide scope due to penicillin-binding protein (PBP) mutations such as β-lactamase non-producing ampicillin-registant (BLNAR) *Haemophilus influenzae*.

The invention claimed is:

1. A carbapenem compound represented by the following formula [1],

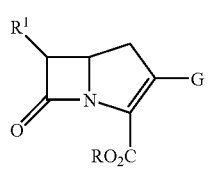

wherein $R^1$ is $C_1$-$C_3$ alkyl substituted by hydroxy, R is hydrogen atom, $C_1$-$C_6$ alkyl, $C_2$-$C_{12}$ alkoxyalkyl, phthalidyl, 2-(4-morpholinyl)ethyl, (2-oxo-1,3-dioxol-4-yl)methyl, (5-methyl-2-oxo-1,3-dioxol-4-yl)methyl, (5-t-butyl-2-oxo-1,3-dioxol-4-yl)methyl,(5-phenyl-2-oxo-1,3-dioxol-4-yl)methyl, or a group of the formula [4]:

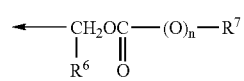

wherein $R^6$ is hydrogen atom or $C_1$-$C_6$ alkyl, $R^7$ is $C_1$-$C_{10}$ alkyl or $C_3$-$C_{10}$ cycloalky, and n is an integer of 0 or 1, and G is a group represented by the formula G3:

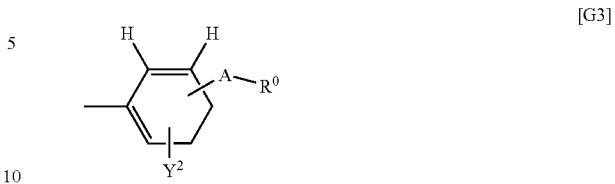

wherein A is —$(CH_2)_s$—$NR^a$—$(CH_2)_t$-(in which, s and t are independently an integer of 0, and $R^a$ is hydrogen atom), $R^0$ is hydrogen atom, and $Y^2$ is $C_1$-$C_4$ alkyl, or a pharmaceutically acceptable salt thereof.

2. The carbapenem compound claimed in claim 1 or a pharmaceutically acceptable salt thereof wherein R is a group of the formula [4]:

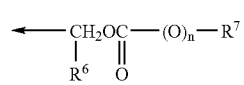

wherein $R^6$ is hydrogen atom or $C_1$-$C_6$ alkyl, $R^7$ is $C_1$-C10 alkyl or $C_3$-$C_{10}$ cycloalky, and n is an integer of 0 or 1.

3. The carbapenem compound claimed in claim 1 or a pharmaceutically acceptable salt thereof wherein $R^1$ is 1-hydroxyethyl.

4. The carbapenem compound claimed in claim 1 or a pharmaceutically acceptable salt thereof wherein R is pivaloyloxymethyl, acetyloxymethyl, acetyloxy-1-ethyl, isopropyloxycarbonyloxy-1-ethyl or cyclohexyloxycarbonyloxy-1-ethyl.

5. The carbapenem compound claimed in claim 1 or a pharmaceutically acceptable salt thereof wherein R is pivaloyloxymethyl.

6. The carbapenem compound claimed in claim 1 or a pharmaceutically acceptable salt thereof wherein R is phthalidyl or (5-methyl-2-oxo-1,3-dioxol-4-yl)methyl.

7. The carbapenem compound claimed in claim 1 or a pharmaceutically acceptable salt thereof wherein R is hydrogen atom.

8. A medicament containing a carbapenem compound claimed in claim 1 or a pharmaceutically acceptable salt thereof as an active ingredient.

9. An antibacterial agent containing a carbapenem compound claimed in claim 1 or a pharmaceutically acceptable salt thereof as an active ingredient.

10. An oral medicament containing a carbapenem compound claimed in claim 1 or a pharmaceutically acceptable salt thereof as an active ingredient.

11. An oral antibacterial agent containing a carbapenem compound claimed in claim 1 or a pharmaceutically acceptable salt thereof as an active ingredient.

12. The carbapenem compound claimed in claim 1 or a pharmaceutically acceptable salt thereof wherein $Y^2$ is methyl.

13. The carbapenem compound claimed in claim 1 or a pharmaceutically acceptable salt thereof wherein $R^1$ is 1-hydroxyethyl, R is hydrogen atom, pivaloyloxymethyl or (5-methyl-2-oxo-1,3-dioxol-4-yl)methyl, A is —NH—, $R^0$ is hydrogen atom and $Y^2$ is methyl.

14. The carbapenem compound claimed in claim 1 or a pharmaceutically acceptable salt thereof wherein $R^1$ is 1-hydroxyethyl, R is hydrogen atom, pivaloyloxymethyl or (5-methyl-2-oxo-1,3-dioxol-4-yl)methyl, A is —NH—, $R^0$ is hydrogen atom and $Y^2$ is methyl, and said -A-$R^0$— is bound to the benzene ring at meta position and said $Y^2$ is bound to the benzene ring at para position against the position where 7-oxo-1-azabicyclo[3.2.0]hept-2-ene is bound to the benzene ring.

15. The carbapenem compound claimed in claim 1 or a pharmaceutically acceptable salt thereof represented by the following formula

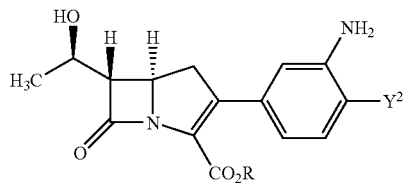

wherein R and $Y^2$ are the same as defined in claim 1.

* * * * *